(12) United States Patent
Borysov

(10) Patent No.: US 12,297,295 B2
(45) Date of Patent: May 13, 2025

(54) PEPTIDE FOR TREATING CANCER

(71) Applicant: Saint Leo University, Saint Leo, FL (US)

(72) Inventor: Sergiy I. Borysov, Tampa, FL (US)

(73) Assignee: Saint Leo University, Saint Leo, FL (US)

( * ) Notice: Subject to any disclaimer, the term of this patent is extended or adjusted under 35 U.S.C. 154(b) by 1027 days.

(21) Appl. No.: 17/215,845

(22) Filed: Mar. 29, 2021

(65) Prior Publication Data

US 2021/0230227 A1 Jul. 29, 2021

Related U.S. Application Data

(63) Continuation-in-part of application No. 17/035,314, filed on Sep. 28, 2020, now Pat. No. 11,597,757.

(60) Provisional application No. 63/029,126, filed on May 22, 2020, provisional application No. 62/907,154, filed on Sep. 27, 2019.

(51) Int. Cl.
 *A61K 38/00* (2006.01)
 *A61K 45/06* (2006.01)
 *A61K 47/64* (2017.01)
 *C07K 7/08* (2006.01)

(52) U.S. Cl.
 CPC ........... *C07K 7/08* (2013.01); *A61K 45/06* (2013.01); *A61K 47/64* (2017.08); *A61K 38/00* (2013.01)

(58) Field of Classification Search
 CPC .......... C07K 7/08; A61K 45/06; A61K 47/64; A61K 38/00
 See application file for complete search history.

(56) References Cited

U.S. PATENT DOCUMENTS

| 6,210,939 B1 * | 4/2001 | Gregory | C07K 14/4746 435/363 |
|---|---|---|---|
| 7,384,735 B1 | 6/2008 | Dryja | |
| 10,919,940 B2 | 2/2021 | Borysov | |
| 2004/0180058 A1 | 9/2004 | Shneider | |
| 2006/0134691 A1 | 6/2006 | Auer et al. | |
| 2019/0359654 A1 | 11/2019 | Borysov | |
| 2021/0095005 A1 | 4/2021 | Borysov | |

FOREIGN PATENT DOCUMENTS

| WO | 98/37091 | 8/1998 |
| WO | 9958135 | 11/1999 |
| WO | 2021041953 | 3/2021 |

OTHER PUBLICATIONS

Yeon-Soo. Frontiers in Molecular Biosciences, Mar. 2018, vol. 5, Article 26.*
Backer et al. Methods in Molecular Biology, vol. 494: Peptide-Based Drug Design (2008).*
International Search Report and Written Opinion, PCT/US2020/053128 (Mar. 16, 2021).
Hosta-Rigau et al., Multifunctionalized Gold Nanoparticles with Peptides Targeted to Gastrin-Releasing Peptide Receptor of a Tumor Cell Line, Bioconjugate Chemistry, vol. 21, No. 6, pp. 1070-1078 (May 18, 2010).
Borysov et al., The N Terminus of the Retinoblastoma Protein Inhibits DNA Replication via a Bipartite Mechanism Disrupted in Partially Penetrant Reinoblastomas, Molecular & Cellular Biology, vol. 36, No. 5, pp. 832-845 (Mar. 2016).
U.S. Appl. No. 17/176,983, entitled Cyclic Peptide for Treating Cancer, filed Feb. 16, 2021.
International Search Report and Written Opinion, PCT/US2022/022363, Aug. 18, 2022.
International Application No. PCT/US2022/022363, Mar. 29, 2022.
Ceballos et al., Cys-Cys and Cys-Lys Stapling of Unprotected Peptides Enabled by Hypervalent Iodine Reagents; Angew Chem. Int. Ed. Engl., Apr. 2021, vol. 60(16), p. 9022-9031., epub Mar. 8, 2021.
Tam et al., Chemical Synthesis of Circular Proteins, J. Biol. Chem. 2012, vol. 287(32), pp. 27020-27025.
Liu et al., Enhancing protein stability with extended disulfide bonds, Proc. Natl. Acad. Sci. USA, 2016, vol. 113(21), pp. 5910-5915.
Gilles et al., Amino-Acid Sequences of the Active-Site Sulfhydryl Peptide and Other Thiol Peptides from teh Cysteine Proteinase a-Clostripain, Eur. J. Biochem., 1983, vol. 130(3), pp. 473-479.
Okumura et al., A chemical method for investigating disulfide-coupled peptide and protein folding, FEBS J. 2012, vol. 279(13), pp. 2283-2295.
Office Action, CA 3,154,764, Aug. 7, 2024.
Retinoblastoma Susceptibility Protein, UNIPROT: Q6DUFO, Aug. 16, 2004.

* cited by examiner

*Primary Examiner* — Jeanette M Lieb
(74) *Attorney, Agent, or Firm* — Akerman LLP; Ryan Harding

(57) ABSTRACT

A peptide is disclosed that has an amino acid sequence selected from SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32, SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; and/or SEQ ID NO: 44. and retro-inversion peptides thereof. The peptides disclosed herein may be used to inhibit helicase activity and treat cancer, such as liver cancer, lung cancer, breast cancer, pancreatic cancer, or brain cancer.

19 Claims, 28 Drawing Sheets

Specification includes a Sequence Listing.

PEPTIDE FOR TREATING CANCER

CROSS-REFERENCE TO RELATED APPLICATIONS

The present application is a continuation-in-part of U.S. patent application Ser. No. 17/035,314, filed Sep. 28, 2020. U.S. patent application Ser. No. 17/035,314 claims priority under 35 U.S.C. § 119(e) to U.S. Provisional Patent Application No. 62/907,154, filed on Sep. 27, 2019, and U.S. Provisional Patent Application No. 63/029,126, filed May 22, 2020. U.S. patent application Ser. No. 17/035,314 and U.S. Provisional Patent Application Nos. 62/907,154 and 63/029,126 are hereby incorporated herein in their entireties.

REFERENCE TO SEQUENCE LISTING

A sequence listing entitled "11990_2_2_ST25.txt" is an ASCII text file and is incorporated herein by reference in its entirety. The text file was created on Apr. 8, 2021 and is 28000 bytes in size.

FIELD OF TECHNOLOGY

The present disclosure generally relates to a peptide for treating cancer. More particularly, a portion of retinoblastoma (Rb) tumor suppressor protein inhibits CMG helicase activity and can inhibit growth of cancer cells.

BACKGROUND

Cancer involves uninhibited dividing of cells and spreading of those cells throughout the body. Normal cells in the body divide in a process that involves several stages and a host of proteins and signaling molecules. When proteins involved in the cell division process become impaired, cancer can result. For example, cells can express tumor suppressor proteins that prevent uncontrolled DNA replication and cell division.

The retinoblastoma (Rb) tumor suppressor protein inhibits helicase activity, thereby exhibiting a growth repressive function. Helicases are enzymes that separate double-stranded DNA into replicable single strands. Exon deletions in the N-terminal domain of Rb (RbN) can be found in patients with hereditary retinoblastomas. Mutations or deletions in the Rb tumor suppressor gene occurs in other cancer types, such as osteosarcoma, and breast and small cell lung cancers. Also, malfunctioning regulatory components of the Rb pathway is a hallmark of human cancers.

Until recently, the mechanism by which RbN suppresses DNA and helicase activity were unknown. It was discovered that the exon 7 domain of RbN is required to inhibit CMG helicase activity. However, it was unknown whether smaller portions of the RbN protein could inhibit helicase and the growth of cancer cells. Down-regulation of the CMG helicase's activity specifically kills cancer cultured cells, while sparing normal non-cancerous cells (Bryant V L et al. Mol. Cancer Res. 2015, 13(9), p. 1296-305; Ge X Q et al. Genes Dev. 2007, 21(24), p. 3331-41; Zimmerman K M et al. Mol. Cancer Res. 2013, 11(4), p. 370-80; Ibarra A et al. Proc. Natl. Acad. Sci., 2008, 105(26), p. 8956-61).

SUMMARY

In an aspect, a peptide comprising or consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44 or retro-inversion peptides thereof is described. In embodiments, if the peptide includes an amino acid sequence flanking an N-terminus, C-terminus, or both of the selected amino acid sequence, at least one of the flanking sequences is an altered flanking sequence.

In one example, the amino acid sequence is SEQ ID NO: 22, SEQ ID NO: 23, SEQ ID NO: 24, SEQ ID NO: 25, SEQ ID NO: 26, SEQ ID NO: 27, or SEQ ID NO: 28.

In one example, the peptide consists of the amino acid sequence of SEQ ID NO: 22, SEQ ID NO: 23, SEQ ID NO: 24, SEQ ID NO: 25, SEQ ID NO: 26, SEQ ID NO: 27, or SEQ ID NO: 28.

In one example, the amino acid sequence is SEQ ID NO: 29, SEQ ID NO: 30, SEQ ID NO: 31, SEQ ID NO: 32, or SEQ ID NO: 33.

In one example, the peptide consists of the amino acid sequence of SEQ ID NO: 29, SEQ ID NO: 30, SEQ ID NO: 31, SEQ ID NO: 32, or SEQ ID NO: 33.

In one example, the amino acid sequence is SEQ ID NO: 34, SEQ ID NO: 35.

In one example, the peptide consists of the amino acid sequence of SEQ ID NO: 34, or SEQ ID NO: 35.

In one example, the amino acid sequence is SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

In one example, the peptide consists of the amino acid sequence of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

In one example, the amino acid sequence further comprises a sulfhydryl group at a N or C terminus of the amino acid sequence.

In one example, the peptide is labeled with a detectable label, contained in a composition including a pharmaceutically acceptable carrier, or conjugated to a cytotoxic molecule, a radioactive molecule, a hydrophilic group, or a hydrophobic group.

In one aspect, a peptide comprising or consisting of an amino acid sequence selected from SEQ ID NO: 34 or SEQ ID NO: 35 or retro-inversion peptides thereof is described.

In one example, the amino acid sequence further comprises a sulfhydryl group at a N or C terminus of the amino acid sequence.

In one example, the peptide is labeled with a detectable label, contained in a composition including a pharmaceutically acceptable carrier, or conjugated to a cytotoxic molecule, a radioactive molecule, a hydrophilic group, or a hydrophobic group.

In another aspect, a method of inhibiting CMG helicase function comprises contacting a cell with a helicase-inhibiting amount of a peptide comprising or consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44 or retro-inversion peptides thereof. If the peptide includes an amino acid sequence flanking an N-terminus, C-terminus, or both of the selected amino acid sequence, at least one of the flanking sequences may be an altered flanking sequence.

In one example, the amino acid sequence further comprises a sulfhydryl group at a N or C terminus of the amino acid sequence.

In one example, the peptide is labeled with a detectable label, contained in a composition including a pharmaceutically acceptable carrier, or conjugated to a cytotoxic molecule, a radioactive molecule, a hydrophilic group, or a hydrophobic group.

In still another aspect, a method of inhibiting CMG helicase function comprises contacting a cell with a helicase-inhibiting amount of a peptide comprising or consisting of an amino acid sequence selected from SEQ ID NO: 34 or SEQ ID NO: 35 or retro-inversion peptides thereof.

In one example, the amino acid sequence further comprises a sulfhydryl group at a N or C terminus of the amino acid sequence.

In one example, the peptide is labeled with a detectable label, contained in a composition including a pharmaceutically acceptable carrier, or conjugated to a cytotoxic molecule, a radioactive molecule, a hydrophilic group, or a hydrophobic group.

In yet another aspect, a method of treating cancer comprises administering to a subject having the cancer with a therapeutically effective amount of a peptide comprising or consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44 or retro-inversion peptides thereof. If the peptide includes an amino acid sequence flanking an N-terminus, C-terminus, or both of the selected amino acid sequence, at least one of the flanking sequences may be an altered flanking sequence. The cancer maybe a carcinoma or sarcoma.

In one example, the amino acid sequence is SEQ ID NO: 29, SEQ ID NO: 30, SEQ ID NO: 31, SEQ ID NO: 32, SEQ ID NO: 33, SEQ ID NO: 34, or SEQ ID NO: 35.

In one example, the peptide consists of the amino acid sequence of SEQ ID NO: 29, SEQ ID NO: 30, SEQ ID NO: 31, SEQ ID NO: 32, SEQ ID NO: 33, SEQ ID NO: 34, or SEQ ID NO: 35.

In one example, the amino acid sequence is SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

In one example, the peptide consists of the amino acid sequence of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

In one example, the carcinoma is selected from liver cancer, lung cancer, breast cancer, pancreatic cancer, prostate cancer, or colorectal cancer, and wherein the sarcoma selected from an osteosarcoma, fibrosarcoma, or glioma.

In one example, the peptide is administered via a route selected from the group consisting of oral administration, nasal administration, administration by inhalation, rectal administration, intraperitoneal injection, intravascular injection, subcutaneous injection, transcutaneous administration, and intramuscular injection.

In one example, the amino acid sequence further comprises a sulfhydryl group at a N or C terminus of the amino acid sequence.

In one example, the peptide is labeled with a detectable label, contained in a composition including a pharmaceutically acceptable carrier, or conjugated to a cytotoxic molecule, a radioactive molecule, a hydrophilic group, or a hydrophobic group.

In one example, the method may also include administering a chemotherapeutic agent.

In still yet another aspect, a method of treating cancer comprises administering to a subject having the cancer with a therapeutically effective amount of a peptide comprising or consisting of an amino acid sequence selected from SEQ ID NO: 34 or SEQ ID NO: 35 or retro-inversion peptides thereof. The cancer may be a carcinoma or sarcoma.

In one example, the carcinoma is selected from liver cancer, lung cancer, breast cancer, pancreatic cancer, prostate cancer, or colorectal cancer, and wherein the sarcoma selected from an osteosarcoma, fibrosarcoma, or glioma.

In one example, the peptide is administered via a route selected from the group consisting of oral administration, nasal administration, administration by inhalation, rectal administration, intraperitoneal injection, intravascular injection, subcutaneous injection, transcutaneous administration, and intramuscular injection.

In one example, the amino acid sequence further comprises a sulfhydryl group at a N or C terminus of the amino acid sequence.

In one example, the peptide is labeled with a detectable label, contained in a composition including a pharmaceutically acceptable carrier, or conjugated to a cytotoxic molecule, a radioactive molecule, a hydrophilic group, or a hydrophobic group.

In one example, the method may also include administering a chemotherapeutic agent.

The foregoing outlines the features and technical advantages of the present disclosure in order that the detailed description that follows may be better understood. Additional features and advantages of the disclosure will be described hereafter that form the subject of the claims of this application. Those skilled in the art should appreciate that the conception and the specific embodiments disclosed may be readily used as a basis for modifying or designing other embodiments for carrying out the same purposes of the present disclosure. Those skilled in the art that should appreciate such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which.

DESCRIPTION

Figure 1:
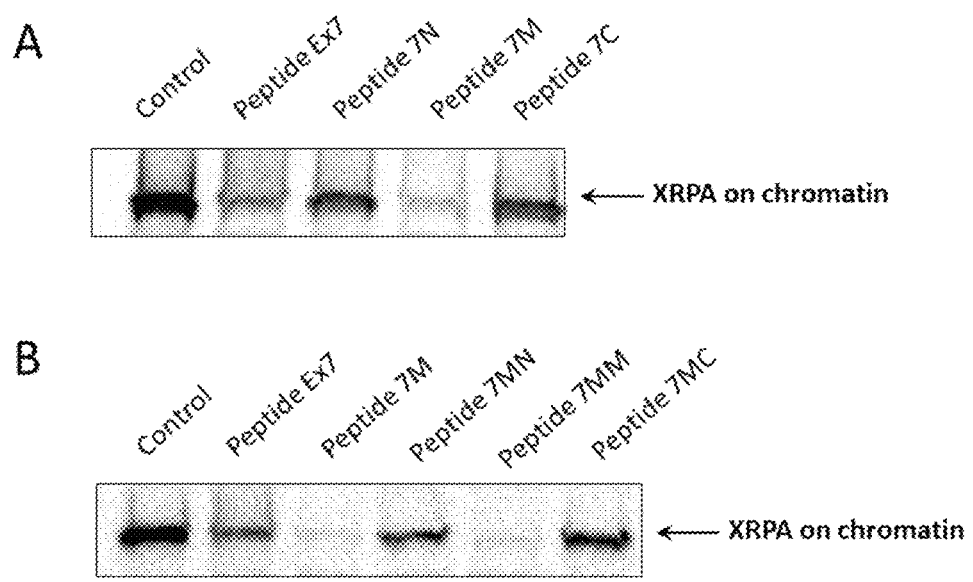
FIG. 1 is an image of a Western blot of chromatin isolated from *Xenopus* egg extracts treated with various peptides in vitro.

Various embodiments are described below. The relationship and functioning of the various elements of the embodiments may better be understood by reference to the following detailed description. The embodiments, however, are not limited to those illustrated in the drawings and described herein. It should be understood that in certain instances details may have been omitted that are not necessary for an understanding of embodiments disclosed herein, such as— for example—conventional peptide synthesis and purification.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

This disclosure describes inventive concepts with reference to specific examples. However, the intent is to cover all modifications, equivalents, and alternatives of the inventive concepts that are consistent with this disclosure.

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein, when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight component X and 5 parts by weight component Y, X and Y are present at a weight ratio of 2:5 and are present in such ratio regardless of whether additional components are contained in the compound.

As used herein, the terms "optional" or "optionally" means that the subsequently described peptide modification and/or derivatization, disclosed event and/or circumstance, or disclosed step in a disclosed method can or cannot occur, and that the description includes instances where said modification and/or derivatization, said event and/or circumstance, and/or said disclosed step in a disclosed method occurs and instances where it does not. In an aspect, a disclosed method can optionally comprise one or more additional steps, such as, for example, repeating an administering step or altering an administering step. In an aspect, a disclosed peptide can optionally comprise one or more modifications and/or derivatizations.

As used herein, the term "subject" refers to the target of administration, e.g., a human being. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote age or sex, and thus, adult and child subjects, as well as fetuses, whether male or female, are intended to be covered. In an aspect, a subject can be a human patient. In an aspect, a subject can have cancer, be suspected of having cancer, or be at risk of developing cancer.

As used herein, the term "diagnosed" means having been subjected to a physical examination by a person of skill, for example, a physician, and found to have a condition (such as, for example, a cancer) that can be diagnosed or treated by one or more of the disclosed compositions, a pharmaceutical preparation comprising one or more disclosed compositions to a subject, and/or disclosed methods. For example, "diagnosed with cancer" means having been subjected to a physical examination by a person of skill, for example, a physician, and found to have a condition that can be treated by one or more of the disclosed compositions, a pharmaceutical preparation comprising one or more disclosed compositions to a subject, and/or disclosed methods. For example, "suspected of having cancer" can mean having been subjected to a physical examination by a person of skill, for example, a physician, and found to have a condition that can likely be treated by one or more of the disclosed compositions, a pharmaceutical preparation comprising one or more disclosed compositions to a subject, and/or disclosed methods.

The words "treat" or "treating" or "treatment" refer to therapeutic or medical treatment wherein the object is to slow down (lessen), ameliorate, and/or diminish an undesired physiological change, disease, pathological condition, or disorder (for example, a cancer) in a subject. As used herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Treatment may not necessarily result in the complete eradication of a cancer but may reduce or minimize complications and side effects of a cancer and/or the progression of a cancer. The success or otherwise of treatment may be monitored by physical examination of the subject as well as cytopathological, DNA, and/or mRNA detection techniques. The words "treat" or "treating" or "treatment" include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the undesired physiological change, disease, pathological condition, or disorder from occurring in a subject that can be predisposed to the disease but has not yet been diagnosed as having it; (ii)

inhibiting the physiological change, disease, pathological condition, or disorder, i.e., arresting its development; or (iii) relieving the physiological change, disease, pathological condition, or disorder, i.e., causing regression of the disease. For example, in an aspect, treating an infection can reduce the severity of an established infection in a subject by 1%-100% as compared to a control (such as, for example, a subject not having cancer). In an aspect, treating can refer to a 1%, 2%, 3%, 4%, 5%, 6%, 7%, 8%, 9%, 10%, 20%, 30%, 40%, 50%, 60%, 70%, 80%, 90%, or 100% reduction in the severity of an established cancer. For example, treating an infection can reduce one or more symptoms of an infection in a subject by 1%-100% as compared to a control (such as, for example, a subject not having cancer or the pre-cancer subject). In an aspect, treating can refer to 1%, 2%, 3%, 4%, 5%, 6%, 7%, 8%, 9%, 10%, 20%, 30%, 40%, 50%, 60%, 70%, 80%, 90%, 100% reduction of one or more symptoms of an established cancer. It is understood that treatment does not necessarily refer to a cure or complete ablation or eradication of a cancer. However, in an aspect, treatment can refer to a cure or complete ablation or eradication of a cancer.

A "patient" refers to a subject afflicted with a cancer. In an aspect, a patient can refer to a subject that has been diagnosed with or is suspected of having a cancer. In an aspect, a patient can refer to a subject that has been diagnosed with or is suspected of having a cancer and is seeking treatment or receiving treatment for the cancer.

As used herein, the term "prevent" or "preventing" or "prevention" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed. In an aspect, preventing a cancer (e.g., an carcinoma or sarcoma) is intended. The words "prevent" and "preventing" and "prevention" also refer to prophylactic or preventative measures for protecting or precluding a subject (e.g., an individual) not having a given infection related complication from progressing to that complication. Individuals in which prevention is required include those who have a cancer or genetic markers for a cancer.

As used herein, the terms "administering" and "administration" refer to any method of providing one or more of the disclosed compositions and/or a pharmaceutical preparation comprising one or more disclosed compositions to a subject to a subject. Such methods are well known to those skilled in the art and include, but are not limited to, the following: oral administration, transdermal administration, administration by inhalation, nasal administration, topical administration, intravaginal administration, ophthalmic administration, intraaural administration, otic administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent.

As used herein, "modifying the method" can comprise modifying or changing one or more features or aspects of one or more steps of a disclosed method. For example, in an aspect, a method can be altered by changing the amount of one or more disclosed peptides, one or more disclosed compositions, and/or one or more disclosed pharmaceutical preparations comprising one or more disclosed peptides and/or one or more disclosed compositions administered to a subject, or by changing the frequency of administration of one or more disclosed peptides, one or more disclosed compositions, and/or one or more disclosed pharmaceutical preparations comprising one or more disclosed peptides and/or one or more disclosed compositions, or by changing the duration of time one or more disclosed peptides, one or more disclosed compositions, and/or one or more disclosed pharmaceutical preparations comprising one or more disclosed peptides and/or one or more disclosed compositions are administered to a subject.

As used herein, "concurrently" means (1) simultaneously in time, or (2) at different times during a common treatment schedule.

As used herein, "effective amount" and "amount effective" can refer to an amount that is sufficient to achieve the desired result such as, for example, the treatment and/or prevention of a cancer (e.g., a carcinoma or sarcoma) or a suspected cancer. As used herein, the terms "effective amount" and "amount effective" can refer to an amount that is sufficient to achieve the desired an effect on an undesired condition (e.g., a cancer). For example, a "therapeutically effective amount" refers to an amount that is sufficient to achieve the desired therapeutic result or to have an effect on undesired symptoms but is generally insufficient to cause adverse side effects. In an aspect, "therapeutically effective amount" means an amount of one or more disclosed peptides, one or more disclosed compositions, and/or one or more disclosed pharmaceutical preparations comprising one or more disclosed peptides and/or one or more disclosed compositions that (i) treats the particular disease, condition, or disorder (e.g., a cancer like carcinoma or sarcoma), (ii) attenuates, ameliorates, or eliminates one or more symptoms of the particular disease, condition, or disorder (e.g., cancer), or (iii) delays the onset of one or more symptoms of the particular disease, condition, or disorder described herein (e.g., a cancer). The specific therapeutically effective dose level for any particular patient will depend upon a variety of factors including the disorder being treated and the severity of the disorder; the specific disclosed peptides, disclosed compositions, and/or disclosed pharmaceutical preparations comprising one or more disclosed peptides and/or one or more disclosed compositions, or methods employed; the age, body weight, general health, sex and diet of the patient; the time of administration; the route of administration; the rate of excretion of the one or more disclosed peptides, one or more disclosed compositions, and/or one or more disclosed pharmaceutical preparations comprising one or more disclosed peptides and/or one or more disclosed compositions employed; the duration of the treatment; drugs used in combination or coincidental with the one or more disclosed peptides, one or more disclosed compositions, and/or one or more disclosed pharmaceutical preparations comprising one or more disclosed peptides and/or one or more disclosed compositions employed, and other like factors well known in the medical arts. For example, it is well within the skill of the art to start doses of one or more disclosed peptides, one or more disclosed compositions, and/or one or more disclosed pharmaceutical preparations comprising one or more disclosed peptides and/or one or more disclosed compositions at levels lower than those required to achieve the desired therapeutic effect and to gradually increase the dosage until the desired effect is achieved. If desired, then the effective daily dose can be divided into multiple doses for purposes of administration. Consequently, a single dose of one or more disclosed peptides, one or more disclosed compositions, and/or one or more disclosed pharmaceutical preparations comprising one or more disclosed peptides and/or one or more disclosed compositions, or methods can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition, such as, for example, a cancer (e.g., a carcinoma or as sarcoma).

The term "contacting" as used herein refers to bringing one or more of the disclosed peptides, disclosed compositions, and/or disclosed pharmaceutical preparation comprising one or more disclosed peptides or compositions together with a target area or intended target area in such a manner that the one or more of the disclosed peptides, compositions, and/or a pharmaceutical preparation comprising one or more disclosed peptides or compositions can exert an effect on the intended target or targeted area either directly or indirectly. A target area or intended target area can be one or more of a subject's organs (e.g., lungs, heart, liver, kidney, etc.). In an aspect, a target area or intended target area can be any cell or any organ infected by a cancer (such as, e.g., a carcinoma or sarcoma).

As used herein, "determining" can refer to measuring or ascertaining the presence and severity of a cancer, such as, for example, a carcinoma or sarcoma). Methods and techniques used to determining the presence and/or severity of a cancer are typically known to the medical arts. For example, the art is familiar with the ways to identify and/or diagnose the presence, severity, or both of a cancer such as a carcinoma or sarcoma.

In various aspects, one or more disclosed peptides, one or more disclosed compositions, and/or one or more disclosed pharmaceutical preparations comprising one or more disclosed peptides and/or one or more disclosed compositions can be administered therapeutically; that is, administered to treat an existing disease or condition (e.g., cancer such as a carcinoma or sarcoma). In an aspect, one or more disclosed peptides, one or more disclosed compositions, and/or one or more disclosed pharmaceutical preparations comprising one or more disclosed peptides and/or one or more disclosed compositions can be administered prophylactically; that is, administered for prevention of a disease or condition (e.g., cancer such as carcinoma or sarcoma). In an aspect, the skilled person can determine an efficacious dose, an efficacious schedule, and an efficacious route of administration for one or more disclosed peptides, one or more disclosed compositions, and/or one or more disclosed pharmaceutical preparations comprising one or more disclosed peptides and/or one or more disclosed compositions to treat or prevent a cancer or metastasis. In an aspect, the skilled person can also alter, change, or modify an aspect of an administering step to improve efficacy of one or more disclosed peptides, one or more disclosed compositions, and/or one or more disclosed pharmaceutical preparations comprising one or more disclosed peptides and/or one or more disclosed compositions.

As used herein, the term "biologically active agent" or "biologic active agent" or "bioactive agent" means an agent that is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include anti-viral agents, vaccines, hormones, antibodies (including active antibody fragments sFv, Fv, and Fab fragments), aptamers, peptide mimetics, functional nucleic acids, therapeutic proteins, peptides, or nucleic acids. Other bioactive agents include prodrugs, which are agents that are not biologically active when administered but, upon administration to a subject are converted to bioactive agents through metabolism or some other mechanism. Additionally, any of the compositions of the invention can contain combinations of two or more bioactive agents. It is understood that a biologically active agent can be used in connection with administration to various subjects, for example, to humans (i.e., medical administration) or to animals (i.e., veterinary administration). As used herein, the recitation of a biologically active agent inherently encompasses the pharmaceutically acceptable salts thereof.

Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a radiosensitizer, the combination of a radiosensitizer and a chemotherapeutic, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, carbonic anhydrase inhibitors, prostaglandin analogs, a combination of an alpha agonist and a beta blocker, a combination of a carbonic anhydrase inhibitor and a beta blocker, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, or a vaccine. In a further aspect, the pharmaceutically active agent can be coumarin, albumin, bromolidine, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, timol hemihydrate, levobunolol hydrochloride, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists (i.e., alpha adrenergic receptor agonist) such as clonidine, brimonidine tartrate, and apraclonidine hydrochloride; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; prostaglandin analogs such as latanoprost, travoprost, and bimatoprost; cholinergics (i.e., acetylcholine receptor agonists) such as pilocarpine hydrochloride and carbachol; glutamate receptor agonists such as the N-methyl D-aspartate receptor agonist memantine; anti-Vascular endothelial growth factor (VEGF) aptamers such as pegaptanib; anti-VEGF antibodies (including but not limited to anti-VEGF-A antibodies) such as ranibizumab and bevacizumab; carbonic anhydrase inhibitors such as methazolamide, brinzolamide, dorzolamide hydrochloride, and acetazolamide; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and diisopyramide phosphate; antiparkinsonian agents, such as dopamine, L-Dopa/Carbidopa, selegiline, dihydroergocryptine, pergolide, lisuride, apomorphine, and bromocriptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides. It is understood that a pharmaceutically active agent can be used in connection with administration to various subjects, for example, to humans (i.e., medical administration) or to animals (i.e., veterinary administration). As used herein, the recitation of a pharmaceutically active agent inherently encompasses the pharmaceutically acceptable salts thereof.

The term "immunostimulant" is used herein to describe a substance which evokes, increases, and/or prolongs an immune response to an antigen. Immunomodulatory agents modulate the immune system, and, as used herein, immunostimulants are also referred to as immunomodulatory agents, where it is understood that the desired modulation is to stimulate the immune system. There are two main categories of immunostimulants, specific and non-specific. Specific immunostimulants provide antigenic specificity in immune response, such as vaccines or any antigen, and non-specific immunostimulants act irrespective of antigenic specificity to augment immune response of other antigen or stimulate components of the immune system without antigenic specificity, such as adjuvants and non-specific immunostimulators. Immunostimulants can include, but are not limited to, levamisole, thalidomide, erythema nodosum leprosum, BCG, cytokines such as interleukins or interferons, including recombinant cytokines and interleukin 2 (aldeslukin), 3D-MPL, QS21, CpG ODN 7909, miltefosine, anti-PD-1 or PD-1 targeting drugs, and acid (DCA, a macrophage stimulator), imiquimod and resiquimod (which activate immune cells through the toll-like receptor 7), chlorooxygen compounds such as tetrachlorodecaoxide (TCDO), agonistic CD40 antibodies, soluble CD40L, 4-1BB:4-1BBL agonists, OX40 agonists, TLR agonists, moieties that deplete regulatory T cells, arabinitol-ceramide, glycerol-ceramide, 6-deoxy and 6-sulfono-myo-insitolceramide, iNKT agonists, and TLR agonists. As used herein, the recitation of an immunostimulant inherently encompasses the pharmaceutically acceptable salts thereof.

As used herein, immune-based products include, but are not limited to, toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103. As used herein, the recitation of an immune-based product inherently encompasses the pharmaceutically acceptable salts thereof.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. In an aspect, a pharmaceutical carrier employed can be a solid, liquid, or gas. In an aspect, examples of solid carriers can include lactose, terra alba, sucrose, talc, gelatin, agar, pectin, acacia, magnesium stearate, and stearic acid. In an aspect, examples of liquid carriers can include sugar syrup, peanut oil, olive oil, and water. In an aspect, examples of gaseous carriers can include carbon dioxide and nitrogen. In preparing a disclosed composition for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Sequence similarity" indicates the percentage of amino acids that either are identical or that represent conservative amino acid substitutions. "Sequence identity" between two amino acid sequences indicates the percentage of amino acids that are identical between the sequences. The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order so to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N, and TFASTA in Wisconsin Genetics Software Package, Genetics Computer Group, 575 Science Drive, Madison, Wis.). The percentage identity is calculated by determining the number of identical positions between the two sequences being compared, dividing this number by the number of positions compared and multiplying the result obtained by 100 to obtain the percentage identity between these two sequences.

In an aspect, the peptide may comprise or consist of a selected amino acid sequence. For example, the peptide may include an N-terminus flanking sequence extending from the N-terminus of the selected sequence and/or a C-terminus flanking sequence extending from the C-terminus of the selected amino acid sequence.

In an aspect, when the peptide includes one or more flanking sequences that flank a selected sequence, at least one flanking sequence may be altered relative to the corresponding native Rb sequence (SEQ ID NO: 45) as determined from the registration of the selected sequence with the native Rb peptide sequence. For example, if SEQ ID NO: 29 is selected, this amino acid sequence registers from amino acid position 211 to amino acid position 226 of the native Rb peptide sequence. If the peptide further includes a 10 amino acid flanking sequence that flanks the N-terminus of SEQ ID NO: 29, the 10 amino acid N-terminus flanking sequence corresponds to amino acids extending from amino acid position 210 to amino acid position 201. If the 10 amino acid flanking sequence is an altered flanking sequence, the flanking sequence is altered with respect to the corresponding amino acids of the native Rb peptide sequence from amino acid position 201 to amino acid position 210.

An "altered flanking sequence" is an amino acid sequence having between 95% and 0% sequence identity with corresponding amino acids flanking the sequence of the native Rb peptide sequence as registered by the selected amino acid sequence, i.e., registration of the selected amino acid sequence with the native Rb peptide sequence. For example, an altered flanking sequence may have 90%, 85%, 80%, 75%, 70%, 65%, 60%, 55%, 50%, 45%, 40%, 35%, 30%, 25%, 20%, 15%, 10%, 5%, or 0% sequence identity with that of the corresponding amino acid sequence of the native Rb peptide. For example, an altered flanking sequence may have less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% sequence identity with that of the corresponding amino acid sequence of the native Rb peptide. The altered identity of altered flanking sequences also excludes conservative substitutions such that conservative substitutions are considered as having an amino acid identity of the amino acid conservatively substituted.

In an aspect, the altered identity of an altered flanking sequences may further exclude one or more substitutions and/or deletions giving rise to one or more amino acid frame shifts with respect to registration with the native Rb peptide sequence. For example, the altered identity of an altered flanking sequence may exclude between 1 and 3, between 1 and 5, between 1 and 10, or between 1 and 15 nonconsecutive single or double amino acid deletions or substitutions such that such substitutions or deletions are accounted for when determining sequence identity with corresponding amino acids with respect to the native Rb sequence. For instance, the flanking sequence may be re-registered, offsetting the sequence to account for the deletion or substitution. In another example, the altered identity of an altered flanking sequence may exclude 1 or more deletions of 3 or more consecutive amino acids, such as less than 5, less than 10, less than 15, less than 25, less than 45, less than 60, less than 75, less than 100, less than 150, less than 200, less than 250, less than 300, or less than 500 consecutive amino acids.

In an aspect, a disclosed peptide having one or more altered flanking sequences retains most or all of the anti-CMG helicase activity and/or anti-cancer activity of the selected amino acid sequence alone. In an aspect, a disclosed peptide having one or more altered flanking sequences may retain 100%, 95% or greater, 90% or greater, 85% or greater, 80% or greater, 75% or greater, 70% or greater, 65% or greater, 60% or greater, 55% or greater, 50% or greater, 45% or greater, 40% or greater, 35% or greater, 30% or greater, 25% or greater, 20% or greater, 15% or greater, 10% or greater, or 5% or greater of the anti-CMG helicase activity and/or anti-cancer activity of a peptide consisting of the selected amino acid sequence. In an aspect, a disclosed peptide having one or more altered flanking sequences may retain 95%, 90%, 85%, 80%, 75%, 70%, 65%, 60%, 55%, 50%, 45%, 40%, 35%, 30%, 25%, 20%, 15%, 10%, or 5% of the anti-CMG helicase activity and/or anti-cancer activity of a peptide consisting of the selected amino acid sequence. In an aspect, a disclosed peptide having one or more altered flanking sequences may retain between 90% and 100%, between 80% and 90%, between 70% and 80%, between 60% and 70%, between 50% and 60%, between 40% and 50%, between 30% and 40%, between 20% and 30%, between 10%-20%, and 0%-10% of the anti-CMG helicase activity and/or anti-cancer activity of a peptide consisting of the selected amino acid sequence.

In some embodiments, a disclosed peptide having one or more altered flanking sequences may exhibit more anti-CMG helicase activity and/or anti-cancer activity than a peptide consisting of the selected amino acid sequence. For example, a disclosed peptide having one or more altered flanking sequences may demonstrate 10%, 20%, 30%, 40%, 50%, 60%, 70%, 80%, 90%, 100%, 200%, 300%, 400%, 500%, 600%, 700%, 800%, 900%, or 1000%, or more of the anti-CMG helicase activity and/or anti-cancer activity of a peptide consisting of the selected amino acid sequence. For example, a disclosed peptide having one or more altered flanking sequences may demonstrate 10%-20%, 20%-30%, 30%-40%, 40%-50%, 50%-60%, 60%-70%, 70%-80%, 80%-90%, 90%-100%, 100%-200%, 200%-300%, 300%-400%, 400%-500%, 500%-600%, 600%-700%, 700%-800%, 800%-900%, or 900%-1000%, or more of the anti-CMG helicase activity and/or anti-cancer activity of a peptide consisting of the selected amino acid sequence.

In an aspect, the altered flanking sequence may also be modified and/or derivative.

In an aspect, an altered flanking sequence may consists of 1, 2, 3, 4, less than 5, less than 10, less than 15, less than 25, less than 50, less than 75, less than 100, less than 150, less than 200, less than 250, less than 300, less than 350, less than 400, or less than 500 amino acids. In one example, the number of amino acids in an altered flanking sequence is as above and the altered flanking sequence has 80% or less than 80% sequence identity with respect to the native Rb peptide sequence.

In an aspect, a disclosed peptide includes a selected sequence having one or more altered flanking sequences. In one example, the altered flanking sequence includes amino acids that collectively have greater positive or negative charge compared to the corresponding flanking sequence of the native Rb peptide flanking the selected sequence. In one example, the altered flanking sequence includes amino acids that are collectively more acidic compared to the corresponding flanking sequence of the native Rb peptide flanking the selected sequence. In one example, the altered flanking sequence includes amino acids that are collectively more amphipathic compared to the corresponding flanking sequence of the native Rb peptide flanking the selected sequence. In one example, the altered flanking sequence includes amino acids that are collectively more polar, neutral, acidic, basic, hydrophilic, or hydrophobic compared to the corresponding flanking sequence of the native Rb peptide flanking the selected sequence. In one example, the altered flanking sequence includes amino acids providing greater solubility in biological media, water, or 0.9% NaCl.

In one embodiment, a disclosed peptide may be conjugated, fused, coupled, attached, encapsulated, or otherwise associated with a delivery component. For example, a delivery component may enhance solubility, increase cell permeability to the peptide, aid translocation of the peptide across cellular membranes. The delivery component may be configured to deliver the peptide to a target cell type, receptor, or cell surface. In various embodiments, the delivery component may include a nanoparticle, such as a diamond nanoparticle, gold nanoparticle, or liposome. For example, the peptide may be fused to and/or encapsulated within a nanoparticle. Additionally or alternatively, the delivery component may include an antibody or antibody fragment.

In some embodiments, a peptide is disclosed that has an amino acid sequence selected from SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 18, SEQ ID NO: 19, SEQ ID NO: 20, and SEQ ID NO: 21, where $X_1$, $X_{11}$, $X_{13}$, $X_{15}$, $X_{16}$, and $X_{17}$ may be independently absent, glycine, alanine, leucine, isoleucine, or valine; $X_2$ may be absent, alanine, or serine; $X_3$, $X_5$, and $X_6$ may be independently absent, tyrosine, or phenylalanine; $X_4$ and $X_{14}$ may be independently absent, aspartic acid, or asparagine; $X_7$ and $X_{10}$ may be independently glycine, alanine, leucine, isoleucine, or valine; $X_8$ may be methionine, isoleucine, or norleucine; $X_9$ is cysteine, alanine, or valine; $X_{12}$ may be absent, glutamine, or glutamic acid, and $X_{18}$ may be absent, lysine, or arginine.

In some embodiments, the amino acid sequence comprises Ile-Ser-Phe-Gln-Leu-Met-Leu-Cys-Val-Leu-Asp-Tyr-Phe (SEQ ID NO: 1). In some embodiments, the amino acid sequence consists of SEQ ID NO: 1.

In some embodiments, the amino acid sequence comprises Gln-Leu-Met-Leu-Cys-Val-Leu (SEQ ID NO: 2). In some embodiments, the amino acid sequence consists of SEQ ID NO: 2.

In some embodiments, the amino acid sequence comprises SEQ ID NO: 3. In some embodiments, the amino acid sequence consists of SEQ ID NO: 3.

In some embodiments, the amino acid sequence comprises Asp-Leu-Val-Ile-Ser-Phe-Gln-Leu-Met-Leu-Cys-Val-Leu-Asp-Tyr-Phe-Ile-Lys (SEQ ID NO: 14). In some embodiments, the amino acid sequence consists of SEQ ID NO: 14.

In some embodiments, $X_1$ may be absent. In some embodiments, $X_1$ may be glycine. In some embodiments, $X_1$ may be alanine. In some embodiments, $X_1$ may be leucine. In some embodiments, $X_1$ may be isoleucine. In some embodiments, $X_1$ may be valine.

In some embodiments, $X_2$ may be absent. In some embodiments, $X_2$ may be serine. In some embodiments, $X_2$ may be alanine.

In some embodiments, $X_3$ may be absent. In some embodiments, $X_3$ may be phenylalanine. In some embodiments, $X_3$ may be tyrosine.

In some embodiments, $X_4$ may be absent. In some embodiments, $X_4$ may be asparagine. In some embodiments, $X_4$ may be aspartic acid.

In some embodiments, $X_5$ may be absent. In some embodiments, $X_5$ may be tyrosine. In some embodiments, $X_5$ may be phenylalanine.

In some embodiments, $X_6$ may be absent. In some embodiments, $X_6$ may be phenylalanine. In some embodiments, $X_6$ may be tyrosine.

In some embodiments, $X_7$ may be glycine. In some embodiments, $X_7$ may be alanine. In some embodiments, $X_7$ may be leucine. In some embodiments, $X_7$ may be isoleucine. In some embodiments, $X_7$ may be valine.

In some embodiments, $X_8$ may be methionine. In some embodiments, $X_8$ may be norleucine. In some embodiments, $X_8$ may be isoleucine.

In some embodiments, $X_9$ may be cysteine. In some embodiments, $X_9$ may be alanine. In some embodiments, $X_9$ may be valine.

In some embodiments, $X_{10}$ may be glycine. In some embodiments, $X_{10}$ may be alanine. In some embodiments, $X_{10}$ may be leucine. In some embodiments, $X_{10}$ may be isoleucine. In some embodiments, $X_{10}$ may be valine.

In some embodiments, $X_{11}$ may be absent. In some embodiments, $X_{11}$ may be glycine. In some embodiments, $X_{11}$ may be alanine. In some embodiments, $X_{11}$ may be leucine. In some embodiments, $X_{11}$ may be isoleucine. In some embodiments, $X_{11}$ may be valine.

In some embodiments, $X_{12}$ may be absent. In some embodiments, $X_{12}$ may be glutamine. In some embodiments, $X_{12}$ may be glutamic acid.

In some embodiments, $X_{13}$ may be absent. In some embodiments, $X_{13}$ may be glycine. In some embodiments, $X_{13}$ may be alanine. In some embodiments, $X_{13}$ may be leucine. In some embodiments, $X_{13}$ may be isoleucine. In some embodiments, $X_{13}$ may be valine.

In some embodiments, $X_{14}$ may be absent. In some embodiments, $X_{14}$ may be asparagine. In some embodiments, $X_{14}$ may be aspartic acid.

In some embodiments, $X_{15}$ may be absent. In some embodiments, $X_{15}$ may be glycine. In some embodiments, $X_{15}$ may be alanine. In some embodiments, $X_{15}$ may be leucine. In some embodiments, $X_{15}$ may be isoleucine. In some embodiments, $X_{15}$ may be valine.

In some embodiments, $X_{16}$ may be absent. In some embodiments, $X_{16}$ may be glycine. In some embodiments, $X_{16}$ may be alanine. In some embodiments, $X_{16}$ may be leucine. In some embodiments, $X_{16}$ may be isoleucine. In some embodiments, $X_{16}$ may be valine.

In some embodiments, $X_{17}$ may be absent. In some embodiments, $X_{17}$ may be glycine. In some embodiments, $X_{17}$ may be alanine. In some embodiments, $X_{17}$ may be leucine. In some embodiments, $X_{17}$ may be isoleucine. In some embodiments, $X_{17}$ may be valine.

In some embodiments, $X_{18}$ may be absent. In some embodiments, $X_{18}$ may be lysine. In some embodiments, $X_{18}$ may be arginine.

In some embodiments, the peptide comprises a truncated amino acid sequence of SEQ ID NO: 14 selected from LVISFQLMLCVLDYFIK (SEQ ID NO: 22), VISFQLMLCVLDYFIK (SEQ ID NO: 23), ISFQLMLCVLDYFIK (SEQ ID NO: 24), SFQLMLCVLDYFIK (SEQ ID NO: 25), FQLMLCVLDYFIK (SEQ ID NO: 26), QLMLCVLDYFIK (SEQ ID NO: 27), LMLCVLDYFIK (SEQ ID NO: 28), DLVISFQLMLCVLDYF (SEQ ID NO: 29), DLVISFQLMLCVLDY (SEQ ID NO: 30), DVISFQLMLCVLD (SEQ ID NO: 31), DVISFQLMLCVL (SEQ ID NO: 32), DVISFQLML (SEQ ID NO: 33), or a retro-inversion, functional homologue, or a conservative substituted version thereof. In some embodiments the functional homologue thereof has at least 90% identity. In some embodiments, the functional homologue thereof has at least 95% identity. In one embodiment, a peptide is disclosed that comprises an amino acid sequence of SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or a functional homologue thereof have no more than two substituted amino acids within the respective amino acid sequence.

In some embodiments, the peptide consists of a truncated amino acid sequence of SEQ ID NO: 14 selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or a retro-inversion, functional homologue, or a conservative substituted version thereof. In some embodiments the functional homologue thereof has at least 90% identity. In some embodiments, the functional homologue thereof has at least 95% identity. In one embodiment, a peptide is disclosed that consists of an amino acid sequence of SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or a functional homologue thereof have no more than two substituted amino acids within the respective amino acid sequence.

In some embodiments, the peptide comprises a substituted amino acid sequence of SEQ ID NO: 14 selected from DLVISFALMLCVLDYFIK (SEQ ID NO: 34), DLVISFQGMLCVLDYFIK (SEQ ID NO: 35), or a retro-inversion, functional homologue, or a conservative substituted version thereof. In some embodiments the functional homologue thereof has at least 90% identity. In some embodiments, the functional homologue thereof has at least 95% identity. In one embodiment, a peptide is disclosed that comprises an amino acid sequence of SEQ ID NO: 34 or SEQ ID NO: 35, or a functional homologue thereof have no more than two substituted amino acids within the respective amino acid sequence.

In some embodiments, the peptide consists of a substituted amino acid sequence of SEQ ID NO: 14 selected from SEQ ID NO: 34, SEQ ID NO: 35, or a retro-inversion, functional homologue, or a conservative substituted version thereof. In some embodiments the functional homologue thereof has at least 90% identity. In some embodiments, the functional homologue thereof has at least 95% identity. In one embodiment, a peptide is disclosed that consists of an amino acid sequence of SEQ ID NO: 34 or SEQ ID NO: 35, or a functional homologue thereof have no more than two substituted amino acids within the respective amino acid sequence.

In some embodiments, the peptide comprises a variation of amino acid sequence of SEQ ID NO: 2 selected from QGMLCVL (SEQ ID NO: 36), QLMGCVL (SEQ ID NO: 37), QLMLCVLD (SEQ ID NO: 38), LMLCVL (SEQ ID NO: 39), GMLCVL (SEQ ID NO: 40), LMGCVL (SEQ ID NO: 41), LMLCVLD (SEQ ID NO: 42), GMLCVLD (SEQ ID NO: 43), LMGCVLD (SEQ ID NO: 44), or a retro-inversion, functional homologue, or a conservative substituted version thereof. In some embodiments the functional homologue thereof has at least 90% identity. In some embodiments, the functional homologue thereof has at least 95% identity. In one embodiment, a peptide is disclosed that comprises an amino acid sequence of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a functional homologue thereof have no more than two substituted amino acids within the respective amino acid sequence.

In some embodiments, the peptide consists of a variation of amino acid sequence of SEQ ID NO: 2 selected from SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a retro-inversion, functional homologue, or a conservative substituted version thereof. In some embodiments the functional homologue thereof has at least 90% identity. In some embodiments, the functional homologue thereof has at least 95% identity. In one embodiment, a peptide is disclosed that consists of an amino acid sequence of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a functional homologue thereof have no more than two substituted amino acids within the respective amino acid sequence. The term "peptide" as used herein, refers to a compound made up of a single chain of D- or L-amino acids or a mixture of D- and L-amino acids joined by peptide bonds.

The term "peptide" as used herein is defined as a chain of amino acid residues, usually having a defined sequence. As used herein, "peptide" can be a non-modified peptide or a modified and/or derivatized peptide. In an aspect, a peptide can have one or more modifications and/or derivatizations.

The peptide may comprises a homolog, a variant, or a functional fragment of the sequences described herein above. In another embodiment, the peptide comprises an amino acid sequence that is about 95%, 96%, 97%, 98% or 99% identical to the sequences described herein. The amino acid substitution will typically be a conservation substitution. The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions. For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner. When affecting conservative substitutions the substituting amino acid should have the same or a similar functional group in the side chain as the original amino acid.

The variables $X_1$-$X_{18}$ represent conservative substitutions that are believed to not substantially alter the activity of the peptide. The term "conservative substitution" is used in reference to peptides to reflect amino acid substitutions that do not substantially alter the activity or binding affinity of the molecule. Typically, conservative amino acid substitutions involve substitution one amino acid for another amino acid with similar chemical properties, such as charge or hydrophobicity.

In some embodiments the peptide consists of the amino acid sequence Ile-Ser-Phe-Gln-Leu-Met-Leu (SEQ ID NO: 5) or Leu-Cys-Val-Leu-Asp-Tyr-Phe (SEQ ID NO: 6). In some embodiments the peptide comprises the amino acid sequence shown in SEQ ID NO: 5 or SEQ ID NO: 6 or a functional homologue thereof. In some embodiments the peptide comprises the amino acid sequence shown in SEQ ID NO: 5 or SEQ ID NO: 6 or a functional homologue thereof having at least 90% identity with SEQ ID NO: 5 or SEQ ID NO: 6. In some embodiments, the functional homologue has at least 95% identity with SEQ ID NO: 5 or SEQ ID NO: 6. In one embodiment, a peptide is disclosed that comprises an amino acid sequence of SEQ ID NO: 5 or SEQ ID NO: 6 or a functional homologue thereof have no more than two substituted amino acids within the respective amino acid sequence.

In some embodiments, the amino acid sequence can be the sequence shown in SEQ ID NO: 4. In some embodiments, the peptide consists of the amino acid shown in SEQ ID NO: 4.

In some embodiments, the amino acid sequence can be the sequence shown in SEQ ID NO: 5. In some embodiments, the peptide consists of the amino acid shown in SEQ ID NO: 5.

In some embodiments, the amino acid sequence can be the sequence shown in SEQ ID NO: 7. In some embodiments, the peptide consists of the amino acid shown in SEQ ID NO: 7.

In some embodiments, the amino acid sequence can be the sequence shown in SEQ ID NO: 10. In some embodiments, the peptide consists of the amino acid shown in SEQ ID NO: 10.

In some embodiments, the amino acid sequence can be the sequence shown in SEQ ID NO: 11. In some embodiments, the peptide consists of the amino acid shown in SEQ ID NO: 11.

In some embodiments, the amino acid sequence can be the sequence shown in SEQ ID NO: 12. In some embodiments, the peptide consists of the amino acid shown in SEQ ID NO: 12.

In some embodiments, the amino acid sequence can be the sequence shown in SEQ ID NO: 13. In some embodiments, the peptide consists of the amino acid shown in SEQ ID NO: 13.

In some embodiments, the amino acid sequence can be the sequence shown in SEQ ID NO: 15. In some embodiments, the peptide consists of the amino acid shown in SEQ ID NO: 15.

In some embodiments, the amino acid sequence can be the sequence shown in SEQ ID NO: 16. In some embodiments, the peptide consists of the amino acid shown in SEQ ID NO: 16.

In some embodiments, the amino acid sequence can be the sequence shown in SEQ ID NO: 17. In some embodiments, the peptide consists of the amino acid shown in SEQ ID NO: 17.

In some embodiments, the amino acid sequence can be the sequence shown in SEQ ID NO: 18. In some embodiments, the peptide consists of the amino acid shown in SEQ ID NO: 18.

In some embodiments, the amino acid sequence can be the sequence shown in SEQ ID NO: 19. In some embodiments, the peptide consists of the amino acid shown in SEQ ID NO: 19.

In some embodiments, the amino acid sequence can be the sequence shown in SEQ ID NO: 20. In some embodiments, the peptide consists of the amino acid shown in SEQ ID NO: 20.

In some embodiments, the amino acid sequence can be the sequence shown in SEQ ID NO: 21. In some embodiments, the peptide consists of the amino acid shown in SEQ ID NO: 21.

In some embodiments, the amino acid sequence can be the sequence shown in SEQ ID NO: 22. In some embodiments, the peptide consists of the amino acid shown in SEQ ID NO: 22.

In some embodiments, the amino acid sequence can be the sequence shown in SEQ ID NO: 23. In some embodiments, the peptide consists of the amino acid shown in SEQ ID NO: 23.

In some embodiments, the amino acid sequence can be the sequence shown in SEQ ID NO: 24. In some embodiments, the peptide consists of the amino acid shown in SEQ ID NO: 24.

In some embodiments, the amino acid sequence can be the sequence shown in SEQ ID NO: 25. In some embodiments, the peptide consists of the amino acid shown in SEQ ID NO: 25.

In some embodiments, the amino acid sequence can be the sequence shown in SEQ ID NO: 26. In some embodiments, the peptide consists of the amino acid shown in SEQ ID NO: 26.

In some embodiments, the amino acid sequence can be the sequence shown in SEQ ID NO: 27. In some embodiments, the peptide consists of the amino acid shown in SEQ ID NO: 27.

In some embodiments, the amino acid sequence can be the sequence shown in SEQ ID NO: 28. In some embodiments, the peptide consists of the amino acid shown in SEQ ID NO: 28.

In some embodiments, the amino acid sequence can be the sequence shown in SEQ ID NO: 29. In some embodiments, the peptide consists of the amino acid shown in SEQ ID NO: 29.

In some embodiments, the amino acid sequence can be the sequence shown in SEQ ID NO: 30. In some embodiments, the peptide consists of the amino acid shown in SEQ ID NO: 30.

In some embodiments, the amino acid sequence can be the sequence shown in SEQ ID NO: 31. In some embodiments, the peptide consists of the amino acid shown in SEQ ID NO: 31.

In some embodiments, the amino acid sequence can be the sequence shown in SEQ ID NO: 32. In some embodiments, the peptide consists of the amino acid shown in SEQ ID NO: 32.

In some embodiments, the amino acid sequence can be the sequence shown in SEQ ID NO: 33. In some embodiments, the peptide consists of the amino acid shown in SEQ ID NO: 33.

In some embodiments, the amino acid sequence can be the sequence shown in SEQ ID NO: 34. In some embodiments, the peptide consists of the amino acid shown in SEQ ID NO: 34.

In some embodiments, the amino acid sequence can be the sequence shown in SEQ ID NO: 35. In some embodiments, the peptide consists of the amino acid shown in SEQ ID NO: 35.

In some embodiments, the amino acid sequence can be the sequence shown in SEQ ID NO: 36. In some embodiments, the peptide consists of the amino acid shown in SEQ ID NO: 36.

In some embodiments, the amino acid sequence can be the sequence shown in SEQ ID NO: 37. In some embodiments, the peptide consists of the amino acid shown in SEQ ID NO: 37.

In some embodiments, the amino acid sequence can be the sequence shown in SEQ ID NO: 38. In some embodiments, the peptide consists of the amino acid shown in SEQ ID NO: 38.

In some embodiments, the amino acid sequence can be the sequence shown in SEQ ID NO: 39. In some embodiments, the peptide consists of the amino acid shown in SEQ ID NO: 39.

In some embodiments, the amino acid sequence can be the sequence shown in SEQ ID NO: 40. In some embodiments, the peptide consists of the amino acid shown in SEQ ID NO: 40.

In some embodiments, the amino acid sequence can be the sequence shown in SEQ ID NO: 41. In some embodiments, the peptide consists of the amino acid shown in SEQ ID NO: 41.

In some embodiments, the amino acid sequence can be the sequence shown in SEQ ID NO: 42. In some embodiments, the peptide consists of the amino acid shown in SEQ ID NO: 42.

In some embodiments, the amino acid sequence can be the sequence shown in SEQ ID NO: 43. In some embodiments, the peptide consists of the amino acid shown in SEQ ID NO: 43.

In some embodiments, the amino acid sequence can be the sequence shown in SEQ ID NO: 44. In some embodiments, the peptide consists of the amino acid shown in SEQ ID NO: 44.

In some embodiments, a peptide is disclosed that comprises an amino acid sequence of SEQ ID NO: 1 or a functional homologue thereof having at least 90% identity with SEQ ID NO: 1. In some embodiments, the functional homologue has at least 95% identity with SEQ ID NO: 1. In one embodiment, a peptide is disclosed that comprises an amino acid sequence of SEQ ID NO: 1 or a functional homologue. In one embodiment, a peptide is disclosed that comprises an amino acid sequence of SEQ ID NO: 1 or a functional homologue thereof having no more than two substituted amino acids within the amino acid sequence of SEQ ID NO: 1.

In some embodiments, a peptide consisting of the amino acid sequence of SEQ ID NO: 1 has a molecular weight of about 1591.96.

In some embodiments, a peptide is disclosed that consists of an amino acid sequence of SEQ ID NO: 1 or a functional homologue thereof having at least 90% identity with SEQ ID NO: 1. In some embodiments, the functional homologue has at least 95% identity with SEQ ID NO: 1. In one embodiment, a peptide is disclosed that consists of an amino acid sequence of SEQ ID NO: 1 or a functional homologue. In one embodiment, a peptide is disclosed that consists of an amino acid sequence of SEQ ID NO: 1 or a functional homologue thereof having no more than two substituted amino acids within the amino acid sequence of SEQ ID NO: 1.

In some embodiments, a peptide is disclosed that comprises an amino acid sequence of SEQ ID NO: 2 or a functional homologue thereof having at least 90% identity with SEQ ID NO: 2. In some embodiments, the functional homologue has at least 95% identity with SEQ ID NO: 2. In one embodiment, a peptide is disclosed that comprises an amino acid sequence of SEQ ID NO: 2 or a functional homologue thereof. In one embodiment, a peptide is disclosed that comprises an amino acid sequence of SEQ ID NO: 2 or a functional homologue thereof having no more than two substituted amino acids within the amino acid sequence of SEQ ID NO: 2.

In some embodiments, a peptide is disclosed that consists of an amino acid sequence of SEQ ID NO: 2 or a functional homologue thereof having at least 90% identity with SEQ ID NO: 2. In some embodiments, the functional homologue has at least 95% identity with SEQ ID NO: 2. In one embodiment, a peptide is disclosed that consists of an amino acid sequence of SEQ ID NO: 2 or a functional homologue thereof. In one embodiment, a peptide is disclosed that consists of an amino acid sequence of SEQ ID NO: 2 or a functional homologue thereof having no more than two substituted amino acids within the amino acid sequence of SEQ ID NO: 2.

In some embodiments, a peptide consisting of the amino acid sequence of SEQ ID NO: 2 has a molecular weight of about 819.1.

In some embodiments, a peptide is disclosed that comprises an amino acid sequence of SEQ ID NO: 14 or a functional homologue thereof having at least 90% identity with SEQ ID NO: 14. In some embodiments, the functional homologue has at least 95% identity with SEQ ID NO: 14. In one embodiment, a peptide is disclosed that comprises an amino acid sequence of SEQ ID NO: 14 or a functional homologue thereof. In one embodiment, a peptide is disclosed that comprises an amino acid sequence of SEQ ID NO: 14 or a functional homologue thereof having no more than two substituted amino acids within the amino acid sequence of SEQ ID NO: 14.

In some embodiments, a peptide is disclosed that consists of an amino acid sequence of SEQ ID NO: 14 or a functional homologue thereof having at least 90% identity with SEQ ID NO: 14. In some embodiments, the functional homologue has at least 95% identity with SEQ ID NO: 14. In one embodiment, a peptide is disclosed that consists of an amino acid sequence of SEQ ID NO: 14 or a functional homologue thereof. In one embodiment, a peptide is disclosed that consists of an amino acid sequence of SEQ ID NO: 14 or a functional homologue thereof having no more than two substituted amino acids within the amino acid sequence of SEQ ID NO: 14.

In some embodiments, a peptide consisting of the amino acid sequence of SEQ ID NO: 14 has a molecular weight of about 2160.69.

The sequence similarity between amino acid sequences can be determined using sequence similarity search with the Basic Local Alignment Search Tool (BLAST) program.

The disclosed peptides can be modified or derivatized. In some embodiments, a disclosed peptide can comprise one or more modifications and/or one or more derivatizations. In an aspect, a modification can be optional. In an aspect, a derivatization can be optional. For example, in an aspect, a modification can comprise an N-terminal modification, a C-terminal modification, an internal modification, or a combination thereof. Peptide modifications are known to the skilled person in the art. N-terminal modifications include, but are not limited to, acetylation, addition of biotin, addition of dansyl, addition of 2,4-Dinitrophenyl, addition of fluorescein, addition of 7-methoxycoumarin acetic acid (Mca), and addition of palmitic acid. Internal modifications include, but are not limited, to cyclization (disulfide bonds), cysteine carbamidomethylation (CAM), addition of isotope labeled amino acids, phosphorylation, addition of spacers, PEGylation, and addition of amino hexanoic acid. C-terminal modifications include, but are not limited, to an amide. As used herein, a "derivative" of a peptide is a form of a given peptide that is chemically modified relative to the reference peptide, the modification including, but not limited to, oligomerization or polymerization, modifications of amino acid residues or peptide backbone, cross-linking, cyclization, conjugation, fusion to additional heterologous amino acid sequences, or other modifications that substantially alter the stability, solubility, or other properties of the peptide while substantially retaining anti-CMG helicase activity or anti-cancer activity. Peptide derivatizations are known to the skilled person in the art.

In some embodiments, a disclosed modified and/or derivatized peptide can retain most or all the functionality of the non-modified or non-derivatized peptide. For example, in an aspect, a disclosed peptide having one or more modifications and/or derivatizations can retain most or all the non-modified or non-derivatized peptide's anti-CMG helicase activity and/or anti-cancer activity. In an aspect, a disclosed peptide having one or more modifications and/or derivatizations can retain 100%, 95%, 90%, 85%, 80%, 75%, 70%, 65%, 60%, 55%, 50%, 45%, 40%, 35%, 30%, 25%, 20%, 15%, 10%, or 5% of the non-modified or non-derivatized peptide's anti-anti-CMG helicase activity and/or anti-cancer activity. In an aspect, a disclosed peptide having one or more modifications and/or derivatizations can retain 95%, 90%, 85%, 80%, 75%, 70%, 65%, 60%, 55%, 50%, 45%, 40%, 35%, 30%, 25%, 20%, 15%, 10%, or 5% of the non-modified or non-derivatized peptide's anti-anti-CMG helicase activity and/or anti-cancer activity. In an aspect, a disclosed peptide having one or more modifications and/or derivatizations can retain 90%-100%, or 80%-90%, or 70%-80%, or 60%-70%, or 50%-60%, or 40%-50%, or 30%-40%, or 20%-30%, or 10%-20%, or 0%-10% of the non-modified or non-derivatized peptide's anti-anti-CMG helicase activity and/or anti-cancer activity.

In some embodiments, a disclosed peptide having one or more modifications and/or derivatizations can exhibit more anti-CMG helicase activity and/or anti-cancer activity than the non-modified or non-derivatized peptide. For example, a modified and/or derivatized peptide can demonstrate 10%, 20%, 30%, 40%, 50%, 60%, 70%, 80%, 90%, 100%, 200%, 300%, 400%, 500%, 600%, 700%, 800%, 900%, or 1000%, or more anti-CMG helicase activity and/or anti-cancer activity than the non-modified or non-derivatized peptide. For example, a disclosed modified and/or derivatized peptide can demonstrate 10%-20%, 20%-30%, 30%-40%, 40%-50%, 50%-60%, 60%-70%, 70%-80%, 80%-90%, 90%-100%, 100%-200%, 200%-300%, 300%-400%, 400%-500%, 500%-600%, 600%-700%, 700%-800%, 800%-900%, or 900%-1000%, or more anti-CMG helicase activity and/or anti-cancer activity than the non-modified or non-derivatized peptide.

Also within the scope of this disclosure are functional homologues or multimers of any of the peptides disclosed herein. The peptides may be a circularized dimer or trimer. The characteristic amino acid sequences of the peptides disclosed herein can be flanked by random amino acid sequences or other amino acid sequences to promote cell internalization or nuclear localization.

In some embodiments, the peptide can be labeled with a detectable label. In some embodiments, the peptide can be conjugated to a cytotoxic molecule, a radioactive molecule, amphipathic, hydrophobic, or a hydrophobic group. Such labels may include but are not limited to radioactive label and fluorescent label. Suitable fluorescent labels include, but are not limited to, fluorescein and cyanine dyes.

The peptide can be conjugated to a hydrophobic group at the N or C terminus of the peptide. The hydrophobic group can be a sequence of amino acids having hydrophobic side chains or an aliphatic molecule, such as an aliphatic or aromatic compound. For example, the peptide can be modified to include a $C_5$-$C_{18}$ alkyl carbon chain to confer additional hydrophobicity to the peptide. In one example, a hydrophobic group can be attached to the side chain of any one of the lysine, aspartic acid, glutamine, methionine, or glutamic acid amino acids. The peptide can be conjugated to a hydrophilic group at the N or C terminus of the peptide. The hydrophilic group can be a sequence of amino acids having hydrophilic side chains.

In other embodiments, the peptide further comprises a first cysteine conjugated to an amino acid at an N-terminus or C-terminus. The peptide may comprise a maleimide group, a cycloalkyne group, an alkyne group, an azide group, an NHS ester group, or any other functional group used for bioconjugation.

In some embodiments, the peptides are retro-inversion peptides. A "retro-inversion peptide" refers to a peptide with a reversal of the direction of the peptide bond on at least one position, i.e., a reversal of the amino- and carboxy-termini with respect to the side chain of the amino acid. Thus, a retro-inversion has reversed termini and reversed direction of peptide bonds while approximately maintaining the topology of the side chains as in the native peptide sequence. The retro-inversion peptide can contain L-amino acids or D-amino acids, or a mixture of L-amino acids and D-amino acids, up to all of the amino acids being the D-isomer.

The amino acids sequences disclosed herein are not limited to sequences where the amino acids are joined only by amide bonds. In some embodiments, some or all the amide bonds in the peptide can be replaced with isosteric replacements to create a peptide mimetic compound.

The peptides disclosed herein can be synthesized by any known method, such as for example by solid-phase synthesis or by use of recombinant DNA techniques. The art is familiar with methods of protein and peptide synthesis.

Nucleic acid sequences that encode for the selected peptides disclosed herein may be incorporated in a known manner into appropriate expression vectors (i.e. recombinant expression vectors). After the peptides are isolated from the host cell, the peptides can be circularized.

The peptides can be purified by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography), or by precipitation (immunoprecipitation).

In certain embodiments, a composition is disclosed that comprises a pharmaceutically acceptable carrier and any peptide described herein.

In an aspect, a disclosed composition or a disclosed pharmaceutical preparations comprising one or more disclosed peptides and/or one or more disclosed compositions can include (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition or a disclosed pharmaceutical preparations comprising one or more disclosed peptides and/or one or more disclosed compositions can comprise a pharmaceutically acceptable diluent, carrier, excipient, or stabilizer, or a combination thereof.

In an aspect, a disclosed composition or a disclosed pharmaceutical preparations comprising one or more disclosed peptides and/or one or more disclosed compositions and (i) one or more active agents, (ii) one or more biologically active agents, (iii) one or more pharmaceutically active agents, (iv) one or more immune-based therapeutic agents, (v) one or more clinically approved agents, or (vi) a combination thereof can include a pharmaceutically acceptable diluent, carrier, excipient, or stabilizer, or a combination thereof.

In an aspect, a disclosed composition or a disclosed pharmaceutical preparations comprising one or more disclosed peptides and/or one or more disclosed compositions and (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof can include a pharmaceutically acceptable diluent, carrier, excipient, or stabilizer, or a combination thereof.

While not being bound by any particular theory, it is believed that once the peptide enters the cytosol of a cell, the peptide can diffuse into the nucleus. A pharmaceutically acceptable carrier may assist the peptide in penetrating the cellular membrane to access the cytosol of the cell, although a carrier is not necessarily required for the peptide to pass through the cell membrane.

The compositions disclosed herein can also include diluents and may be prepared in buffered solutions with the proper osmotic environment and a suitable pH.

In other embodiments, a method of inhibiting CMG helicase function is disclosed. The method can include contacting a cell with a helicase-inhibiting amount of any of the peptides described herein. The helicase-inhibiting amount can range from about 1.0 nM to about 100 μM. In some embodiments, the helicase-inhibiting amount can range from about 0.5 μM to about 50 μM, about 1 μM to about 20 μM, or about 1 μM to about 10 μM.

The CMG helicase-inhibiting amount may depend upon whether the peptide is concomitantly delivered with a transfection agent or a delivery system, such as a liposome or polymeric particle.

In some embodiments, a method of treating cancer is disclosed. The method can include administering to a subject having the cancer with a therapeutically effective amount of a peptide comprising or consisting of an amino acid sequence selected from SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and retro-inversion peptides thereof. Where $X_1$, $X_{11}$, $X_{13}$, $X_{15}$, $X_{16}$, and $X_{17}$ may be independently absent, glycine, alanine, leucine, isoleucine, or valine; $X_2$ may be absent, alanine, or serine; $X_3$, $X_5$, and $X_6$ may be independently absent, tyrosine, or phenylalanine; $X_4$ and $X_{14}$ may be independently absent, aspartic acid, or asparagine; $X_7$ and $X_{10}$ may be independently glycine, alanine, leucine, isoleucine, or valine; $X_8$ may be methionine, isoleucine, or norleucine; $X_9$ is cysteine, alanine, or valine; $X_{12}$ may be absent, glutamine, or glutamic acid, and $X_{18}$ may be absent, lysine, or arginine.

In some embodiments, a method of treating cancer is disclosed. The method can include administering to a subject having the cancer with a therapeutically effective amount of a peptide comprising or consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or a retro-inversion, functional homologue, or a conservative substituted version thereof.

In some embodiments, a method of treating cancer is disclosed. The method can include administering to a subject having the cancer with a therapeutically effective amount of a peptide comprising or consisting of an amino acid sequence selected from SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a retro-inversion, functional homologue, or a conservative substituted version thereof.

The cancer may be a carcinoma or epithelial cancer. The cancer may be a carcinoma such as liver cancer, lung cancer, breast cancer, pancreatic cancer, prostate cancer, or colorectal cancer; or a sarcoma such as an osteosarcoma, fibrosarcoma, or glioma. The cancer may be liver cancer, lung cancer, breast cancer, pancreatic cancer, or brain cancer. In some embodiments, the cancer may be liver cancer. In some embodiments, the cancer may be lung cancer. In some embodiments, the cancer may be breast cancer. In some embodiments, the cancer may be pancreatic cancer. In some embodiments, the cancer may be brain cancer. In some embodiments, the cancer may be a glioma. In some embodiments, the cancer may be prostate cancer. In some embodiments, the cancer may be colorectal cancer. In some embodiments, the cancer may be an osteosarcoma. In some embodiments, the cancer may be a fibrosarcoma.

The method may include administering to a subject having a carcinoma or epithelial cancer a therapeutically effective amount of a peptide comprising or consisting of SEQ ID NO: 1, SEQ ID NO: 2, SEQ ID NO: 14 or a combination thereof. In some embodiments, the cancer is selected from the group consisting of glioma, brain, liver, lung, pancreatic, prostate, colorectal, osteosarcoma, fibrosarcoma, and breast cancer.

In some embodiments, a method of inhibiting CMG helicase function can include administering to a subject having the cancer with a therapeutically effective amount of a peptide comprising or consisting of an amino acid sequence selected from SEQ ID NO: 1, SEQ ID NO: 2, SEQ ID NO: 14, or a retro-inversion, functional homologue, or a conservative substituted version thereof, including combinations thereof.

In some embodiments, a method of inhibiting CMG helicase function can include administering to a subject having the cancer with a therapeutically effective amount of a peptide comprising or consisting of an amino acid sequence selected from SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and retro-inversion peptides thereof. Where $X_1$, $X_{11}$, $X_{13}$, $X_{15}$, $X_{16}$, and $X_{17}$ may be independently absent, glycine, alanine, leucine, isoleucine, or valine; $X_2$ may be absent, alanine, or serine; $X_3$, $X_5$, and $X_6$ may be independently absent, tyrosine, or phenylalanine; $X_4$ and $X_{14}$ may be independently absent, aspartic acid, or asparagine; $X_7$ and $X_{10}$ may be independently glycine, alanine, leucine, isoleucine, or valine; $X_8$ may be methionine, isoleucine, or norleucine; $X_9$ is cysteine, alanine, or valine; $X_{12}$ may be absent, glutamine, or glutamic acid, and $X_{18}$ may be absent, lysine, or arginine.

In some embodiments, a method of inhibiting CMG helicase function can include administering to a subject having the cancer with a therapeutically effective amount of a peptide comprising or consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or a retro-inversion, functional homologue, or a conservative substituted version thereof.

In some embodiments, a method of inhibiting CMG helicase function can include administering to a subject having the cancer with a therapeutically effective amount of a peptide comprising or consisting of an amino acid sequence selected from SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a retro-inversion, functional homologue, or a conservative substituted version thereof.

In an aspect, a disclosed method of treating cancer and/or a disclosed method of inhibiting CMG helicase function can comprise administering one or more disclosed peptides, one or more disclosed compositions, and/or one or more disclosed pharmaceutical preparations comprising one or more disclosed peptides and/or one or more disclosed compositions and inhibiting or slowing cell growth in a cancer.

In an aspect a disclosed method of treating cancer and/or a disclosed method of inhibiting CMG helicase function can comprise administering one or more disclosed peptides, one or more disclosed compositions, and/or one or more disclosed pharmaceutical preparations comprising one or more disclosed peptides and/or one or more disclosed compositions and inhibiting or preventing metastasis of a cancer.

In an aspect, a disclosed method of treating cancer and/or a disclosed method of inhibiting CMG helicase function can comprise administering one or more disclosed peptides, one or more disclosed compositions, and/or one or more disclosed pharmaceutical preparations comprising one or more disclosed peptides and/or one or more disclosed compositions and administering (i) one or more active agents, (ii) one or more biologically active agents, (iii) one or more pharmaceutically active agents, (iv) one or more immune-based therapeutic agents, (v) one or more clinically approved agents, or (vi) a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed method of treating cancer and/or a disclosed method of inhibiting CMG helicase function can comprise administering one or more disclosed peptides, one or more disclosed compositions, and/or one or more disclosed pharmaceutical preparations comprising one or more disclosed peptides and/or one or more disclosed compositions and administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a disclosed method of treating cancer and/or a disclosed method of inhibiting CMG helicase function can comprise repeating one or more steps.

In an aspect, a disclosed method of treating cancer and/or a disclosed method of inhibiting CMG helicase function can comprise identifying a subject having been diagnosed with cancer or suspected of having cancer. As known to the art, cancer can be diagnosed and/or confirmed through various tests (such as, e.g., MRI, CT scan, X-ray, biopsy, genetic and protein analysis, biomarkers, etc.).

In an aspect, a disclosed method of treating cancer and/or a disclosed method of inhibiting CMG helicase function can comprise monitoring a subject's response to an administering step, such as for example, the administration of one or more disclosed peptides, one or more disclosed compositions, and/or one or more disclosed pharmaceutical preparations comprising one or more disclosed peptides and/or one or more disclosed compositions and/or the administration of (i) one or more active agents, (ii) one or more biologically active agents, (iii) one or more pharmaceutically active agents, (iv) one or more immune-based therapeutic agents, (v) one or more clinically approved agents, or (vi) a combination thereof.

Methods and techniques to monitor a subject's response to a disclosed administering step can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration or an intensification of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, colostomy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect of a disclosed method of treating cancer and/or a disclosed method of inhibiting CMG helicase function, a monitoring step can be repeated one or more times.

In an aspect, a disclosed method of treating cancer and/or a disclosed method of inhibiting CMG helicase function can comprise modifying or altering one or more steps of a disclosed method. For example, in an aspect, a disclosed method of treating cancer and/or a disclosed method of inhibiting CMG helicase function can comprise modifying or altering an administering step. In an aspect, an administering step can be modified or altered, for example, by changing the route of administration, or changing the dose of a disclosed peptide, a disclosed composition, or a disclosed pharmaceutical preparation comprising a disclosed peptide or composition, or changing the timing of administration, or changing the frequency of the administration, or a combination thereof.

In some embodiments, the amino acid sequence shown in SEQ ID NO: 1 can be administered to the subject having cancer. In some embodiments, the cancer may be a carcinoma such as liver cancer, lung cancer, breast cancer, pancreatic cancer, prostate cancer, or colorectal cancer; or a sarcoma such as an osteosarcoma, fibrosarcoma, or glioma. In one embodiment, the peptide comprises or consists of a functional homologue of the amino acid sequence of SEQ ID NO: 1. In one embodiments, a peptide comprising or consisting of the amino acid sequence of SEQ ID NO: 1 or a functional homologue thereof having at least 90% identity with SEQ ID NO: 1 is administered to the subject having cancer. In one embodiment, the functional homologue has at least 95% identity with SEQ ID NO: 1.

In some embodiments, the amino acid sequence shown in SEQ ID NO: 2 can be administered to the subject having cancer. In some embodiments, the cancer may be a carcinoma such as liver cancer, lung cancer, breast cancer, pancreatic cancer, prostate cancer, or colorectal cancer; or a sarcoma such as an osteosarcoma, fibrosarcoma, or glioma. In one embodiment, the peptide comprises or consists of a functional homologue of the amino acid sequence of SEQ ID NO: 2. In one embodiments, a peptide comprising or consisting of the amino acid sequence of SEQ ID NO: 2 or a functional homologue thereof having at least 90% identity with SEQ ID NO: 2 is administered to the subject having cancer. In one embodiment, the functional homologue has at least 95% identity with SEQ ID NO: 2.

In some embodiments, the amino acid sequence shown in SEQ ID NO: 14 or a functional homologue thereof having at least 90% or at least 95% identity with SEQ ID NO: 14 can be administered to the subject having cancer. In some embodiments, the cancer may be a carcinoma such as liver cancer, lung cancer, breast cancer, pancreatic cancer, prostate cancer, or colorectal cancer; or a sarcoma such as an osteosarcoma, fibrosarcoma, or glioma. In one embodiment, the peptide comprises or consists of a functional homologue of the amino acid sequence of SEQ ID NO: 14. In one embodiments, a peptide comprising or consisting of the amino acid sequence of SEQ ID NO: 14 or a functional homologue thereof having at least 90% identity with SEQ ID NO: 14 is administered to the subject having cancer. In one embodiment, the functional homologue has at least 95% identity with SEQ ID NO: 14.

In some embodiments, a disclosed method of treating cancer and/or a disclosed method of inhibiting CMG helicase function can include administering a chemotherapeutic agent. The chemotherapeutic agent can be administered in combination therapy scenarios.

In an aspect, a disclosed method of treating cancer and/or a disclosed method of inhibiting CMG helicase function can comprise obtaining one or more disclosed peptides, obtaining one or more disclosed compositions, obtaining one or more disclosed pharmaceutical preparations comprising one or more disclosed peptides or disclosed compositions, obtaining one or more disclosed formulations comprising one or more disclosed peptides or disclosed compositions, obtaining one or more active agents, one or more biologically active agents, pharmaceutically active agents, immune-based therapeutic agents, clinically approved agents, or obtaining a combination thereof.

In an aspect, a disclosed method of treating cancer and/or a disclosed method of inhibiting CMG helicase function can comprise preparing one or more disclosed peptides, preparing one or more disclosed compositions, preparing one or more disclosed pharmaceutical preparations comprising one or more disclosed peptides or disclosed compositions, preparing one or more disclosed formulations comprising preparing one or more disclosed peptides or disclosed compositions, preparing one or more active agents, one or more biologically active agents, pharmaceutically active agents, immune-based therapeutic agents, clinically approved agents, or preparing a combination thereof.

In an aspect, a disclosed method of treating cancer and/or a disclosed method of inhibiting CMG helicase function can include administering a disclosed peptide as described herein or as otherwise presently known or known in the future wherein the peptide binds to the Mcm7 protein subunit of the CMG replicative helicase, and thereby prevents activation of helicases or inhibits already active helicases.

In other embodiments, a kit is disclosed. The kit can include a container containing, a peptide comprising an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 18, SEQ ID NO: 19, SEQ ID NO: 20, SEQ ID NO: 21 and retro-inversion peptides thereof. Where $X_1$, $X_{11}$, $X_{13}$, $X_{15}$, $X_{16}$, and $X_{17}$ may be independently absent, glycine, alanine, leucine, isoleucine, or valine; $X_2$ may be absent, alanine, or serine; $X_3$, $X_5$, and $X_6$ may be independently absent, tyrosine, or phenylalanine; $X_4$ and $X_{14}$ may be independently absent, aspartic acid, or asparagine; $X_7$ and $X_{10}$ may be independently glycine, alanine, leucine, isoleucine, or valine; $X_8$ may be methionine, isoleucine, or norleucine; $X_9$ is cysteine, alanine, or valine; $X_{12}$ may be absent, glutamine, or glutamic acid, and $X_{18}$ may be absent, lysine, or arginine. The kit may also include instructional materials teaching the use of the peptide in inhibiting CMG helicase function and/or treatment of cancer.

In some embodiments, a kit is disclosed. The kit can include a container containing, a peptide comprising an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or a retro-inversion, functional homologue, or a conservative substituted version thereof. The kit may also include instructional materials teaching the use of the peptide in inhibiting CMG helicase function and/or treatment of cancer.

In some embodiments, a kit is disclosed. The kit can include a container containing, a peptide comprising an amino acid sequence selected from SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a retro-inversion, functional homologue, or a conservative substituted version thereof. The kit may also include instructional materials teaching the use of the peptide in inhibiting CMG helicase function and/or treatment of cancer.

Disclosed herein is a kit comprising one or more disclosed peptides, one or more disclosed compositions, one or more disclosed pharmaceutical preparations comprising one or more disclosed peptides or disclosed compositions, or combination thereof. In an aspect, a kit can comprise one or more disclosed peptides, preparing one or more disclosed compositions, preparing one or more disclosed pharmaceutical preparations comprising one or more disclosed peptides or disclosed compositions and one or more active agents. In an aspect, a disclosed kit can comprise at least two components constituting the kit. Together, the components constitute a functional unit for a given purpose (such as, for example, treating a subject diagnosed with or suspected of having cancer). Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation. In an aspect, a kit for use in a disclosed method can comprise one or more containers holding a disclosed composition and a label or package insert with instructions for use. In an aspect, a kit can contain one or more additional agents (e.g., active agents, biologically active agents, pharmaceutically active agents, immune-based therapeutic agents, clinically approved agents, or a combination thereof). In an aspect, one or more active agents can treat, inhibit, and/or ameliorate one or more comorbidities in a subject. In an aspect, suitable containers include, for example, bottles, vials, syringes, blister pack, etc. The containers can be formed from a variety of materials such as glass or plastic. The container can hold a disclosed peptide, or a disclosed composition, or a pharmaceutical formulation comprising a disclosed peptide or a disclosed composition and can have a sterile access port (for example the container may be an intravenous solution bag or a vial having a stopper pierceable by a hypodermic injection needle). The label or package insert can indicate that a disclosed composition or a pharmaceutical formulation comprising a disclosed composition can be used for treating, preventing, inhibiting, and/or ameliorating a cancer or complications and/or symptoms associated with a cancer. A kit can comprise additional components necessary for administration such as, for example, other buffers, diluents, filters, needles, and syringes.

In some embodiments, the kit contains a peptide comprising the amino acid sequence of SEQ ID NO: 1 or SEQ ID NO: 2 or a functional homologue thereof having at least 90% or at least 95% identity with SEQ ID NO: 1 or SEQ ID NO: 2.

In some embodiments, the kit contains a peptide comprising the amino acid sequence of SEQ ID NO: 14 or a functional homologue thereof having at least 90% or at least 95% identity with SEQ ID NO: 14.

EXAMPLES

Example 1

The peptide of SEQ ID NO: 1 was synthesized using solid-phase synthesis. The product was purified using HPLC to a purity of about 99%. 250 µM of peptide Ex7 (KGEVLQMEDDLVISFQLMLCVLDYFIKL-SPPMLLKEPYKT) (SEQ ID NO: 8), peptide 7N (circularized—KGEVLQMEDDLV) (SEQ ID NO: 9), peptide 7M (ISFQLMLCVLDYF) (SEQ ID NO: 1), or peptide 7C (IKLSPPMLLKEPYK) (SEQ ID NO: 10) were incubated in S phase arrested *Xenopus* egg extracts. Following a 90 min incubation, chromatin was isolated and probed by Western blotting for RPA protein as a readout for DNA helicase activity. Additionally, peptide 7MN (ISFQLML) (SEQ ID NO: 5), peptide 7MM (QLMLCVL) (SEQ ID NO: 2), and peptide 7MC (LCVLDYF) (SEQ ID NO: 6) were tested.

Example 2

Figure 2:
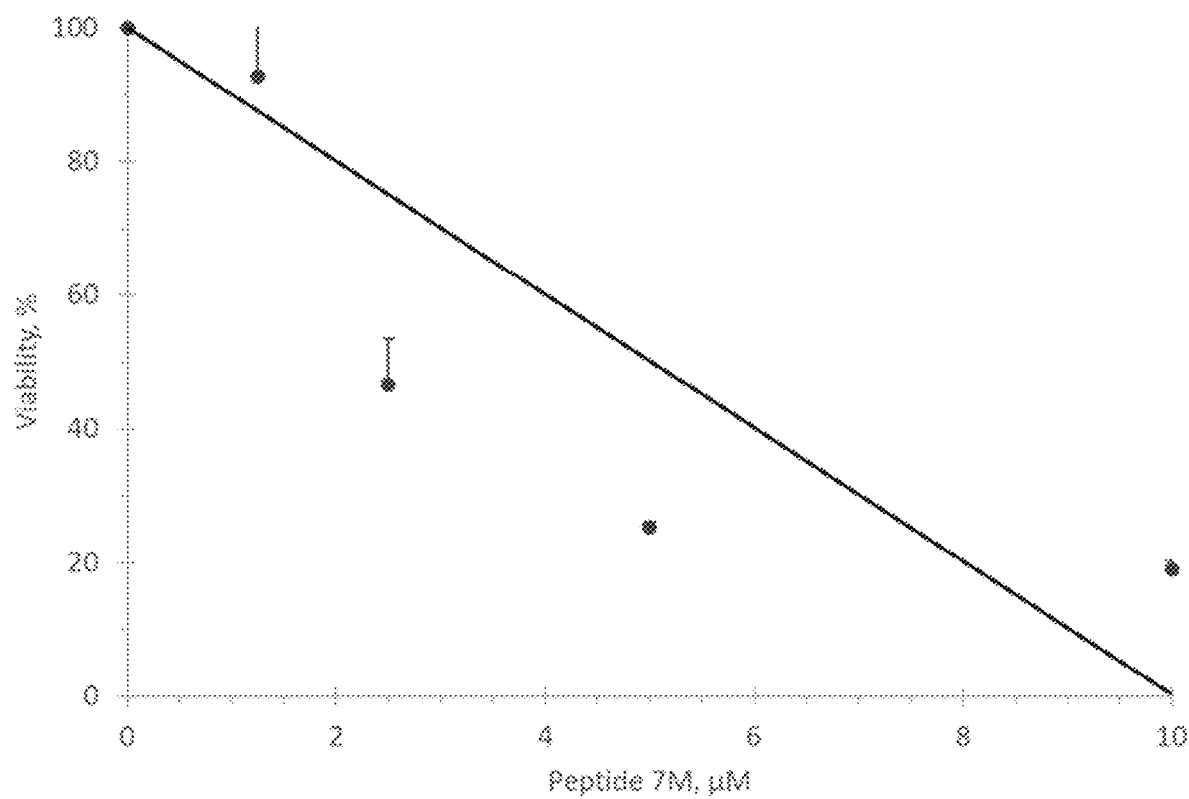
FIG. 2 shows the viability of HepG2 liver cancer cells in the presence of different concentrations of Peptide 7M (SEQ ID NO: 1)
Figure 3:
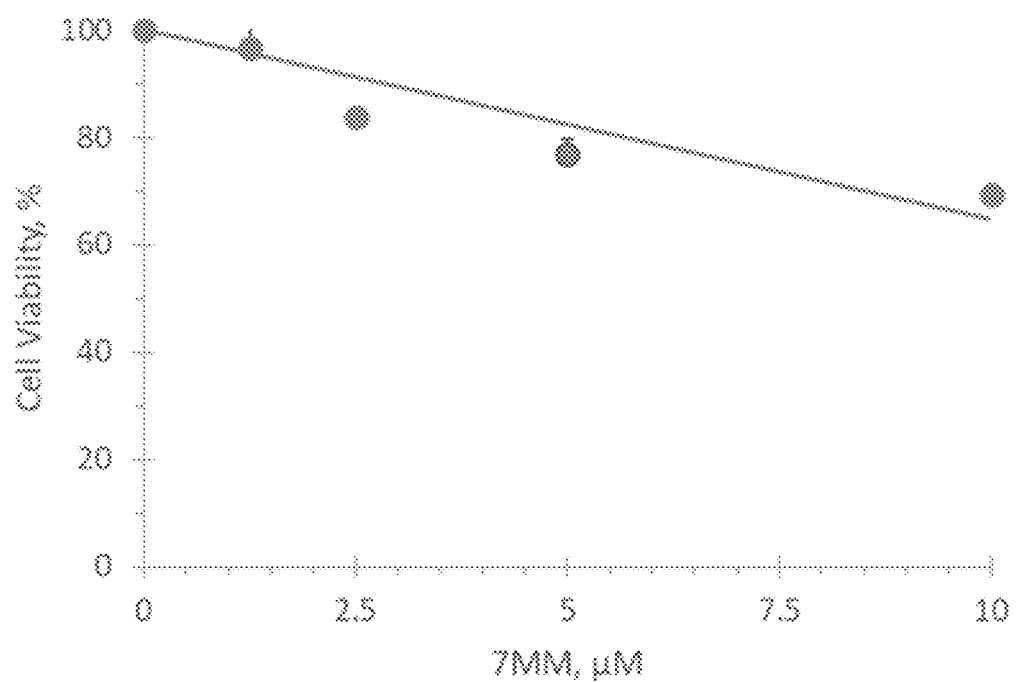
FIG. 3 shows the viability of HepG2 liver cancer cells in the presence of different concentrations of Peptide 7MM (SEQ ID NO: 2)

The effect of Peptides 7M and 7MM on HepG2 liver cancer cells (ATCC #HB-8065) was studied. Pierce Protein Transfection reagent (Thermo Scientific, 89850) was used to deliver peptide to the cultured cells. HepG2 liver cancer cells were transfected with 1.25-10 μM Peptide 7M or Peptide 7MM for 3.5 hrs, incubated in a complete media for a duration of two doubling times (96 hours), and assessed for viability by using a CCK-8 colorimetric assay. FIGS. 2 and 3 show the viability of liver cancer cells as a function of peptide concentration.

Example 3

Figure 4:
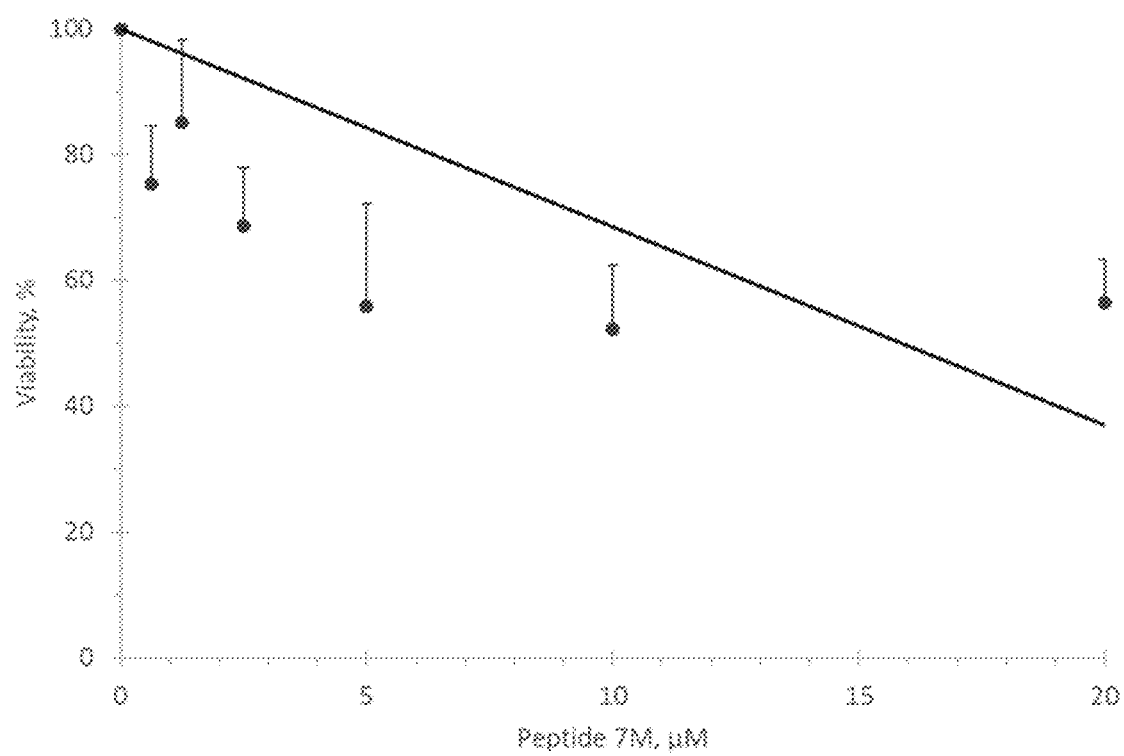
FIG. 4 shows the viability of HLF-a lung cancer cells in the presence of different concentrations of Peptide 7M.
Figure 5:
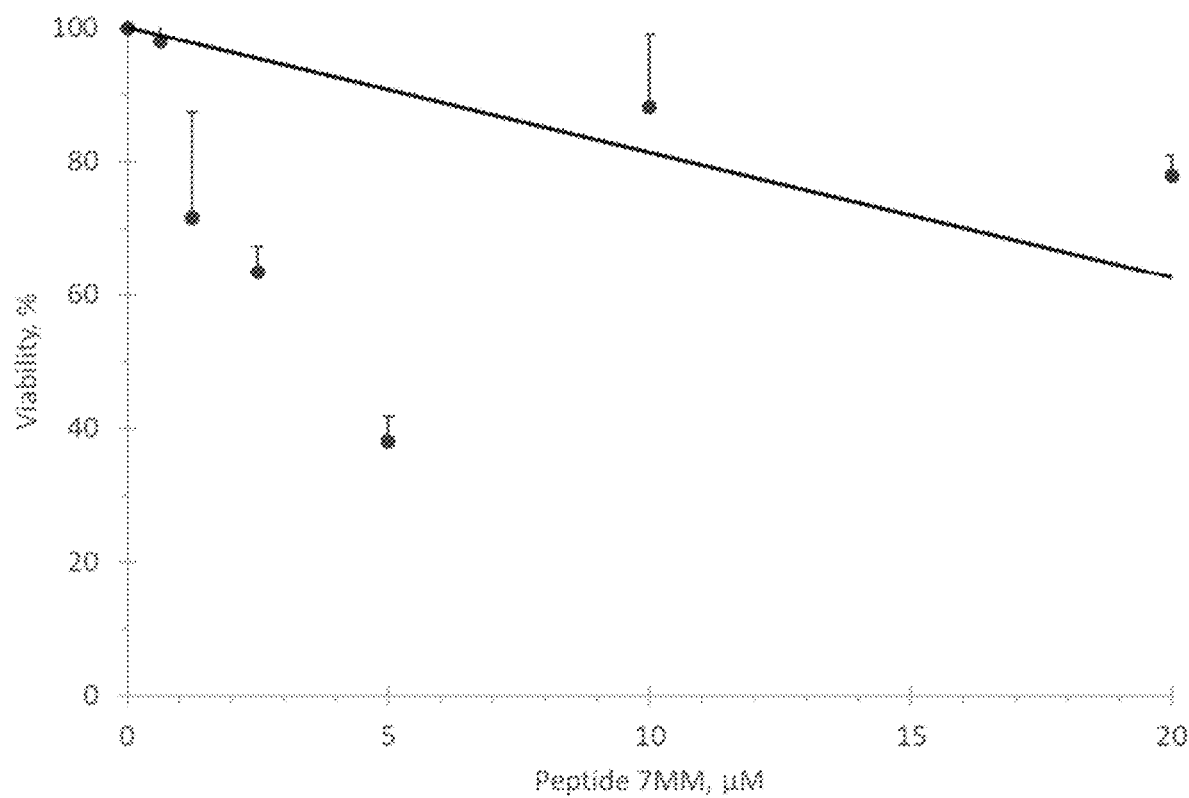
FIG. 5 shows the viability of HLF-a lung cancer cells in the presence of different concentrations of Peptide 7MM.

The effect of Peptides 7M and 7MM on HLF-a lung cancer cells (ATCC #CCL-199) was studied. Pierce Protein Transfection reagent (Thermo Scientific, 89850) was used to deliver peptide to the cultured cells. HLF-a lung cancer cells were transfected with 0.625-20 μM Peptide 7M or Peptide 7MM for 3.5 hrs, incubated in a complete media for a duration of two doubling times (96 hours), and assessed for viability by using a CCK-8 colorimetric assay. FIGS. 4 and 5 show the viability of lung cancer cells as a function of peptide concentration.

Example 4

Figure 6:
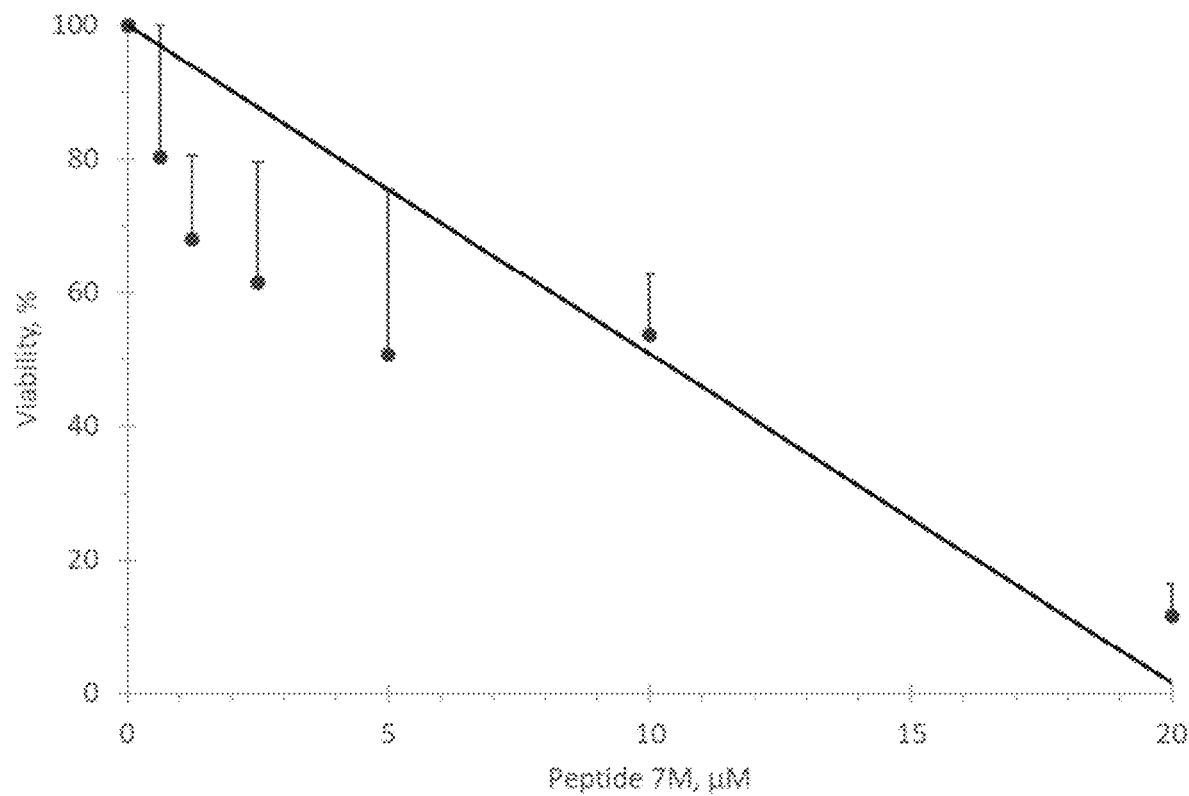
FIG. 6 shows the viability of BT-549 breast cancer cells in the presence of different concentrations of Peptide 7M.
Figure 7:
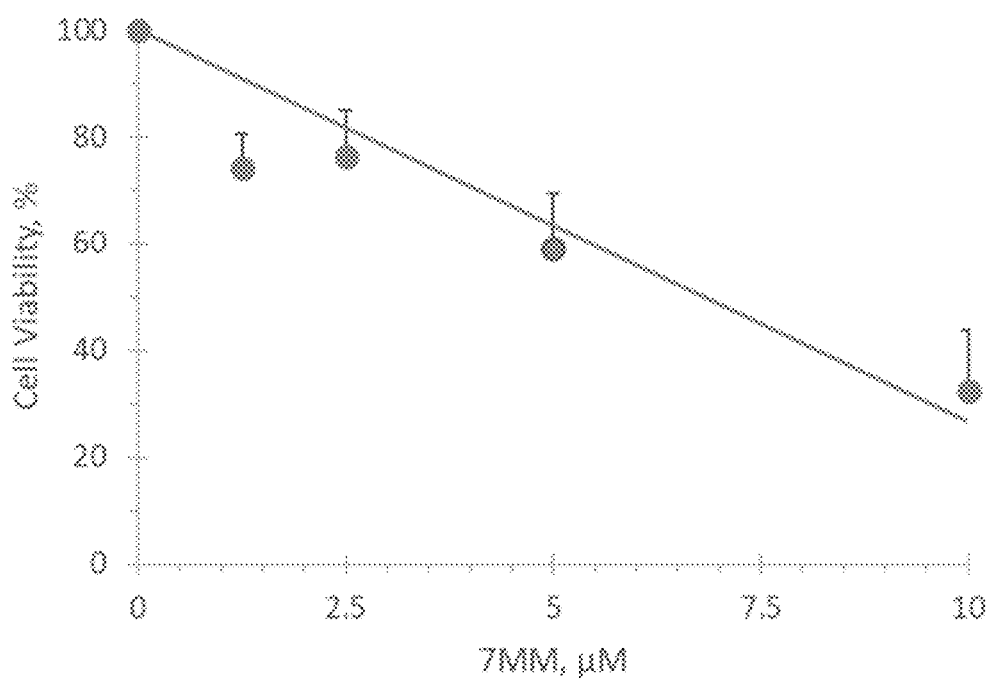
FIG. 7 shows the viability of BT-549 breast cancer cells in the presence of different concentrations of Peptide 7MM.

The effect of Peptides 7M and 7MM on BT-549 breast cancer cells (ATCC #HTB-122) was studied. Pierce Protein Transfection reagent (Thermo Scientific, 89850) was used to deliver peptide to the cultured cells. BT-549 breast cancer cells were transfected with 0.625-20 μM Peptide 7M or 1.25-10 μM Peptide 7MM for 3.5 hrs, incubated in a complete media for a duration of two doubling times (96 hours), and assessed for viability by using a CCK-8 colorimetric assay. FIGS. 6 and 7 show the viability of breast cancer cells as a function of peptide concentration.

Example 5

Figure 8:
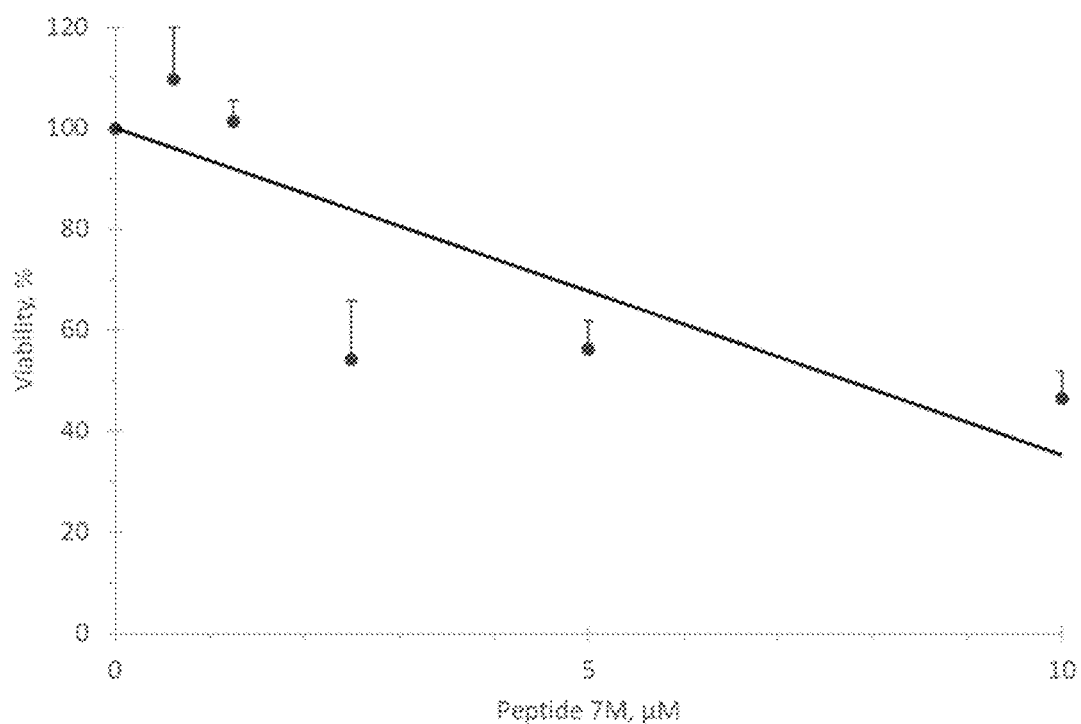
FIG. 8 shows the viability of PANC-1 pancreatic cancer cells in the presence of different concentrations of Peptide 7M.
Figure 9:
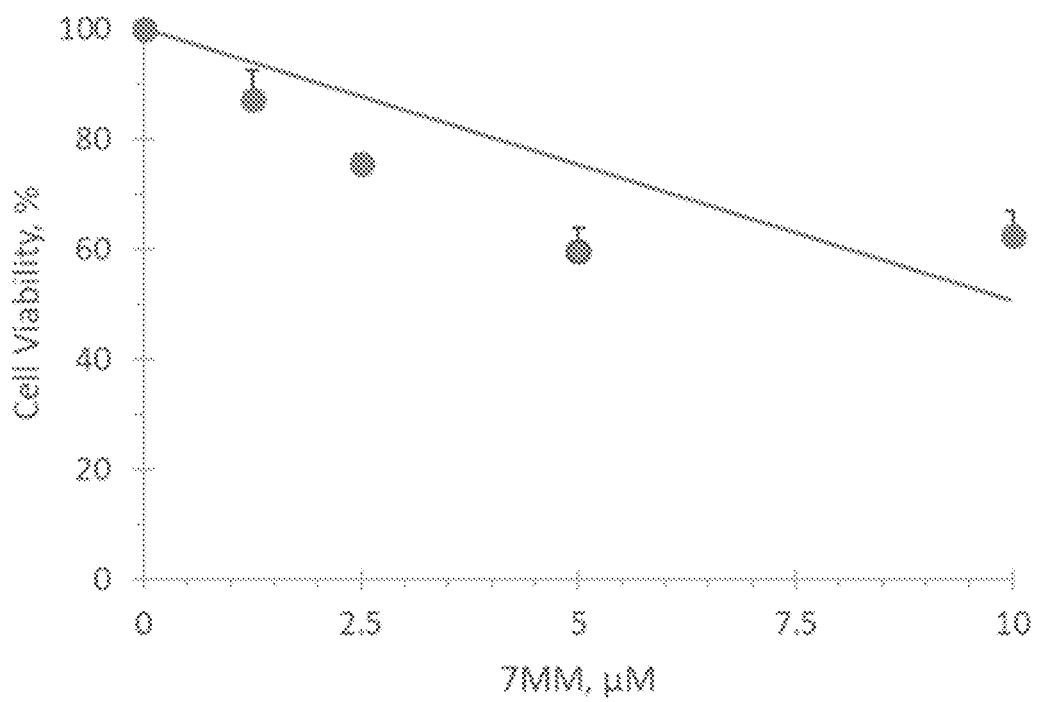
FIG. 9 shows the viability of PANC-1 pancreatic cancer cells in the presence of different concentrations of Peptide 7MM.

The effect of Peptides 7M and 7MM on PANC-1 pancreatic cancer cells (ATCC #CRL-1469) was studied. Pierce Protein Transfection reagent (Thermo Scientific, 89850) was used to deliver peptide to the cultured cells. PANC-1 pancreatic cancer cells were transfected with 0.625-10 μM Peptide 7M or Peptide 7MM for 3.5 hrs, incubated in a complete media for a duration of two doubling times (48 hours), and assessed for viability by using a CCK-8 colorimetric assay. FIGS. 8 and 9 show the viability of pancreatic cancer cells as a function of peptide concentration.

Example 6

Figure 10:
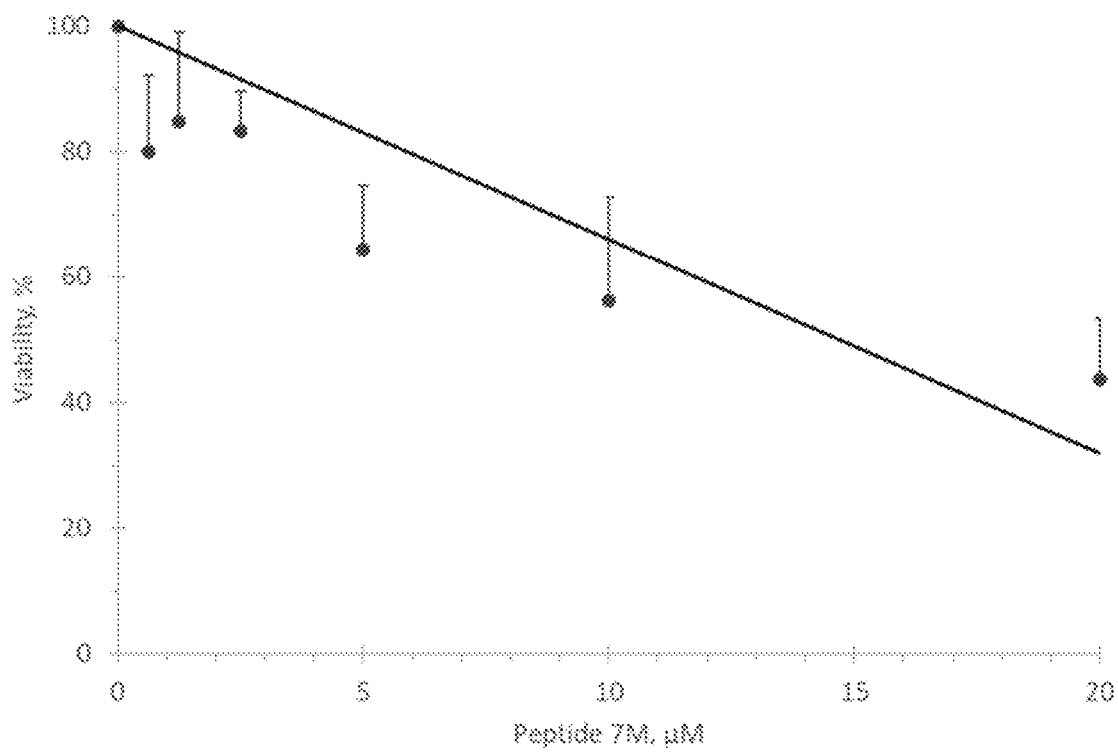
FIG. 10 shows the viability of M059J brain cancer cells in the presence of different concentrations of Peptide 7M.

The effect of Peptide 7M on M059J glioma cancer cells (ATCC #CRL-2366) was studied. Pierce Protein Transfection reagent (Thermo Scientific, 89850) was used to deliver peptide to the cultured cells. PANC-1 pancreatic cancer cells were transfected with 0.625-20 Peptide 7M for 3.5 hrs, incubated in a complete media for a duration of two doubling times (48 hours), and assessed for viability by using a CCK-8 colorimetric assay. FIG. 10 shows the viability of glioma cells as a function of peptide concentration.

Example 7

Figure 11:
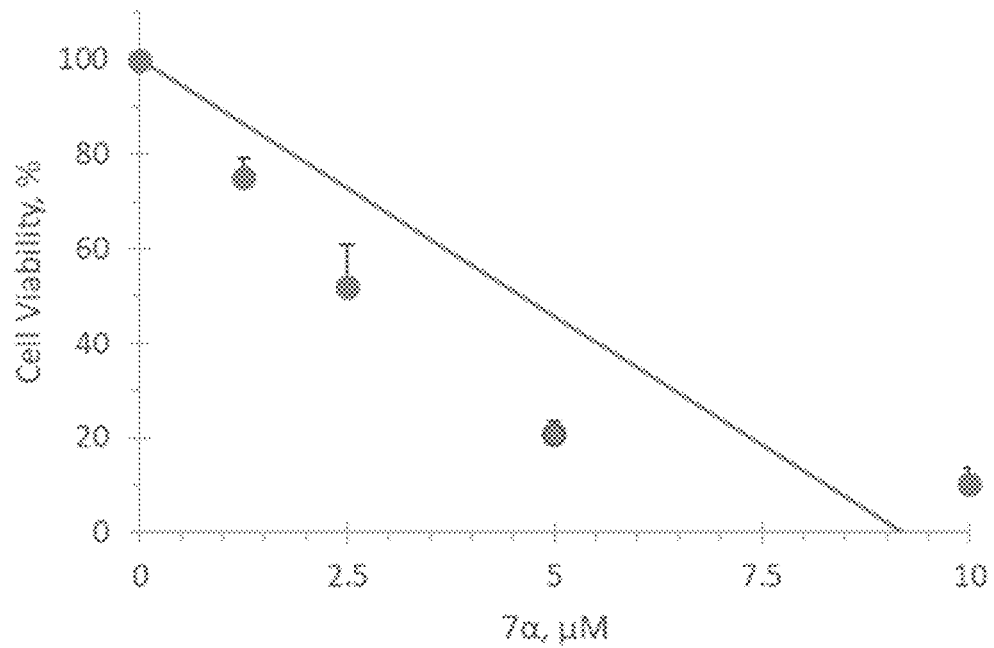
FIG. 11 shows the viability of cultured BT-549 breast cancer cells in the presence of different concentrations of peptide 7α (SEQ ID NO: 14)

The effect of peptide 7α (DLVISFQLMLCVLDYFIK) (SEQ ID NO: 14) on viability of cultured BT-549 breast cancer cells was studied. BT-549 breast cancer cells (ATCC #HTB-122) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 11. shows that peptide 7α decreases viability of cultured BT-549 breast cancer cells.

Example 8

Figure 12:
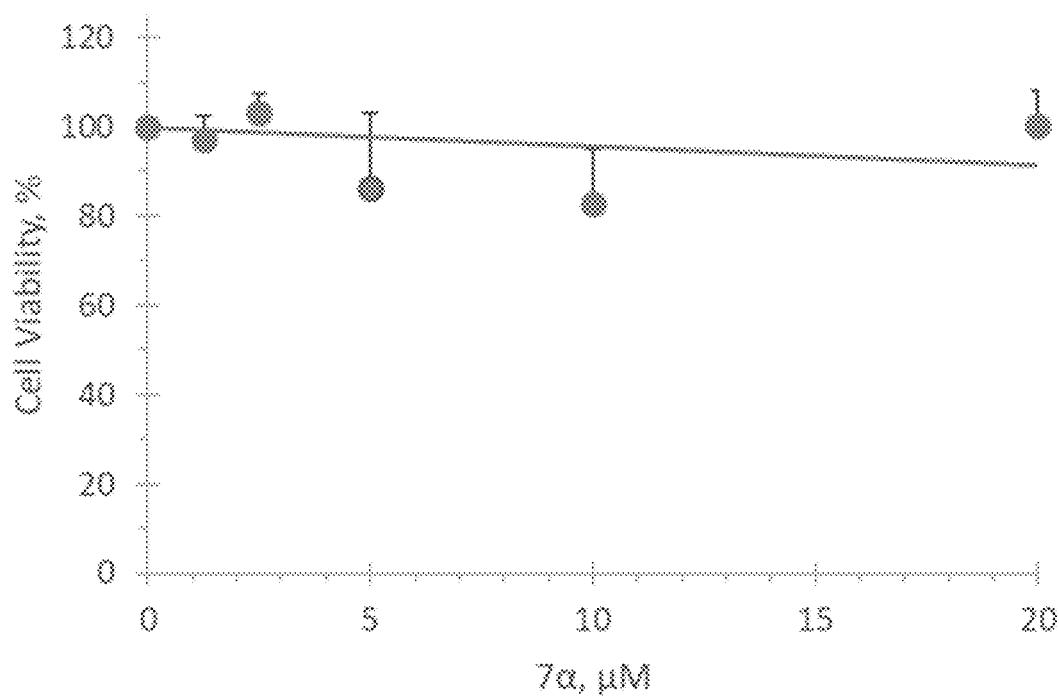
FIG. 12 shows the viability of HMEC primary mammary epithelial normal cells in the presence of different concentrations of peptide 7α.

The effect of peptide 7α on viability of HMEC primary mammary epithelial normal cells was studied. HMEC mammary epithelial cells (ATCC #PCS-600-010) were transfected with 1.25-20 μM peptide 7α for 3.5 hrs, incubated in a complete media for a duration of two doubling times, and assessed for viability by using a CCK-8 colorimetric assay (Dojindo Molecular Technologies, Inc.). FIG. 12 shows that peptide 7α does not affect viability of cultured normal primary mammary epithelial cells.

Example 9

Figure 13:
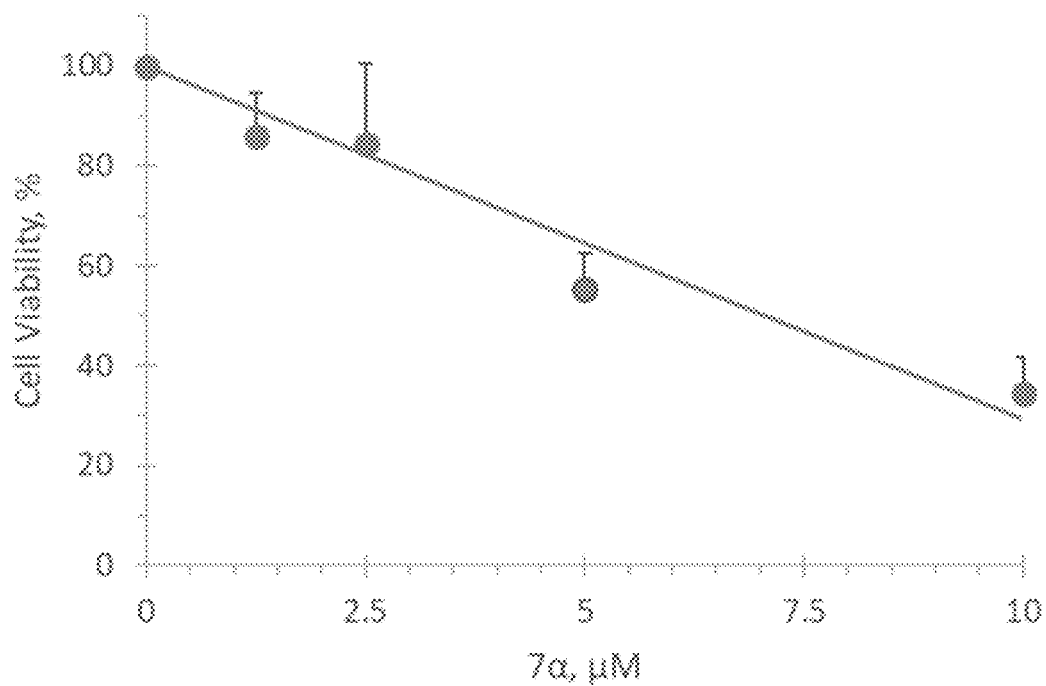
FIG. 13 shows the viability of M059J glioma cancer cells in the presence of different concentrations of peptide 7α.

The effect of peptide 7α on viability of M059J glioma cancer cells was studied. M059J glioma cancer cells (ATCC #CRL-2366) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 13 shows peptide 7α decreases viability of cultured glioma cells.

Example 10

Figure 14:
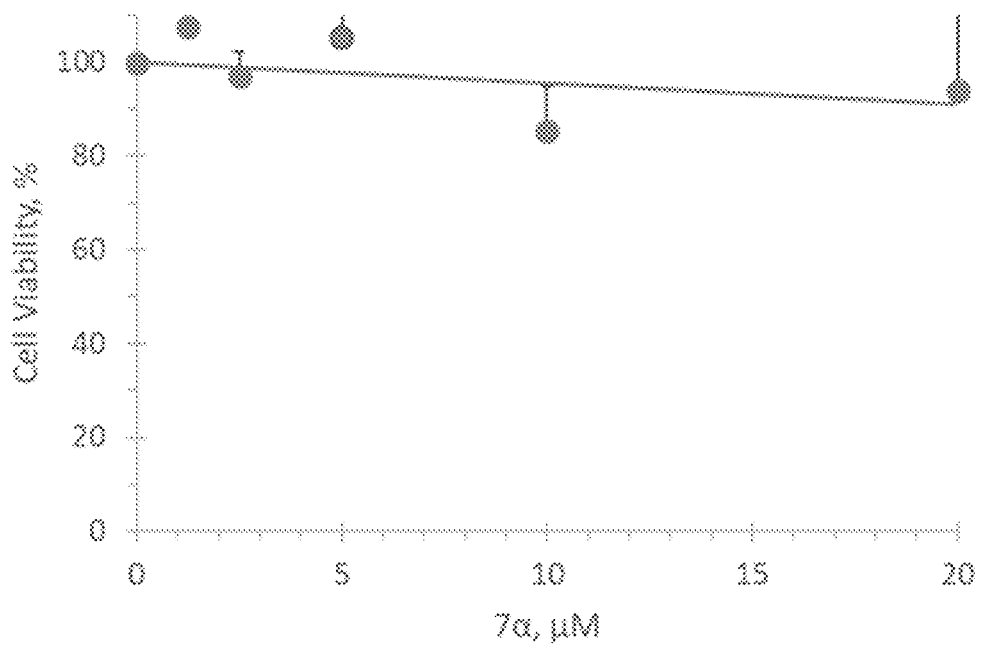
FIG. 14 shows the viability of SCG p13 astroglia brain cells in the presence of different concentrations of peptide 7α.

The effect of peptide 7α on viability of SCG p13 astroglia brain cells was studied. SVG p12 immortalized astroglia cells (ATCC #CRL-8621) were transfected with 1.25-20 μM peptide 7α for 3.5 hrs, incubated in a complete media for a duration of two doubling times, and assessed for viability by using a CCK-8 colorimetric assay (Dojindo Molecular Technologies, Inc.). FIG. 14 shows that peptide 7α does not affect viability of cultured normal brain cells.

Example 11

Figure 15:
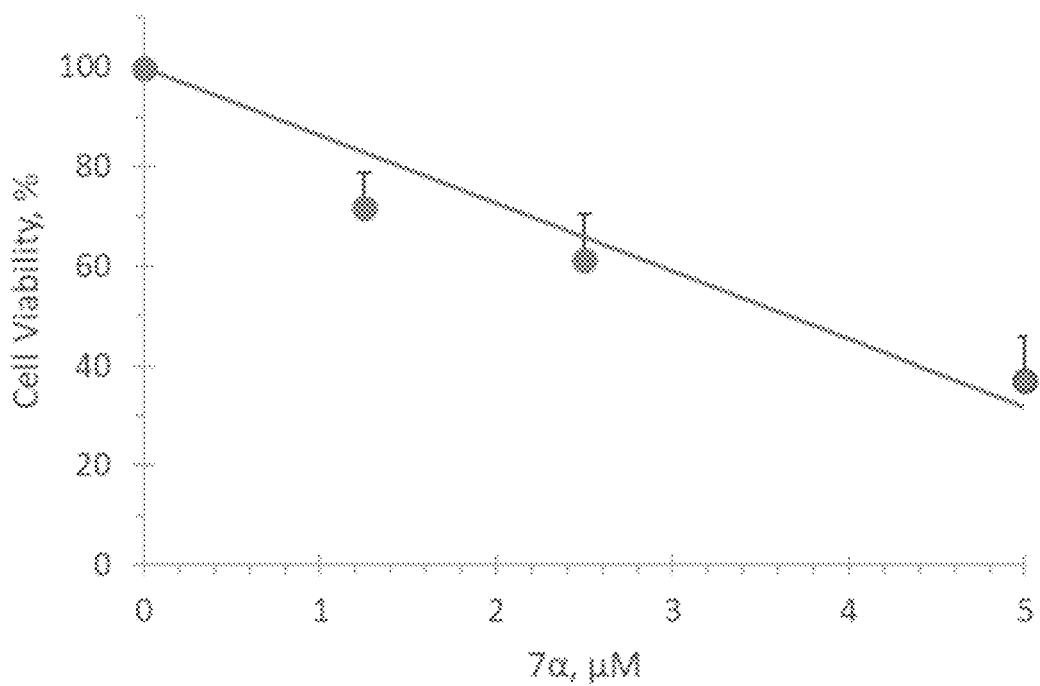
FIG. 15 shows the viability of HepG2 liver cancer cells in the presence of different concentrations of peptide 7α.

The effect of peptide 7α on viability of HepG2 liver cancer cells was studied. HepG2 liver cancer cells (ATCC #HB-8065) were transfected with 1.25-5 μM peptide 7α for 3.5 hrs, incubated in a complete media for a duration of two doubling times, and assessed for viability by using a CCK-8 colorimetric assay (Dojindo Molecular Technologies, Inc.). FIG. 15 shows that peptide 7α decreases viability of cultured liver cancer cells.

Example 12

Figure 16:
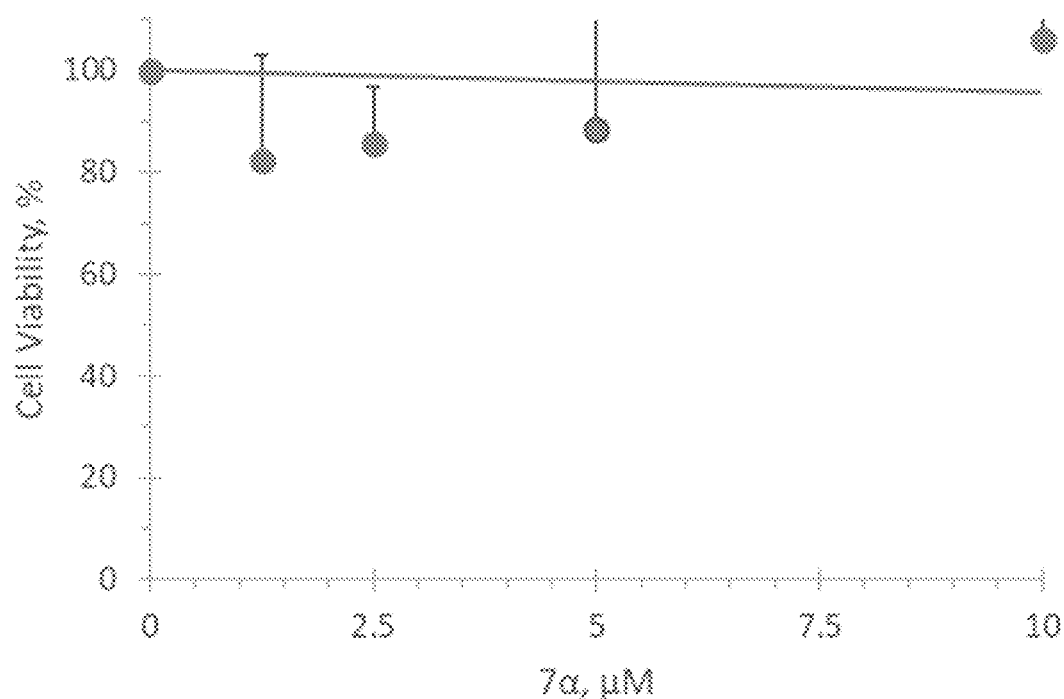
FIG. 16 shows the viability of THLE-3 immortalized normal liver cells in the presence of different concentrations of peptide 7α.

The effect of peptide 7α on viability of THLE-3 immortalized normal liver cells was studied. THLE-3 immortalized liver cells (ATCC #CRL-11233) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 16 shows that peptide 7α does not affect viability of cultured normal liver cells.

Example 13

Figure 17:
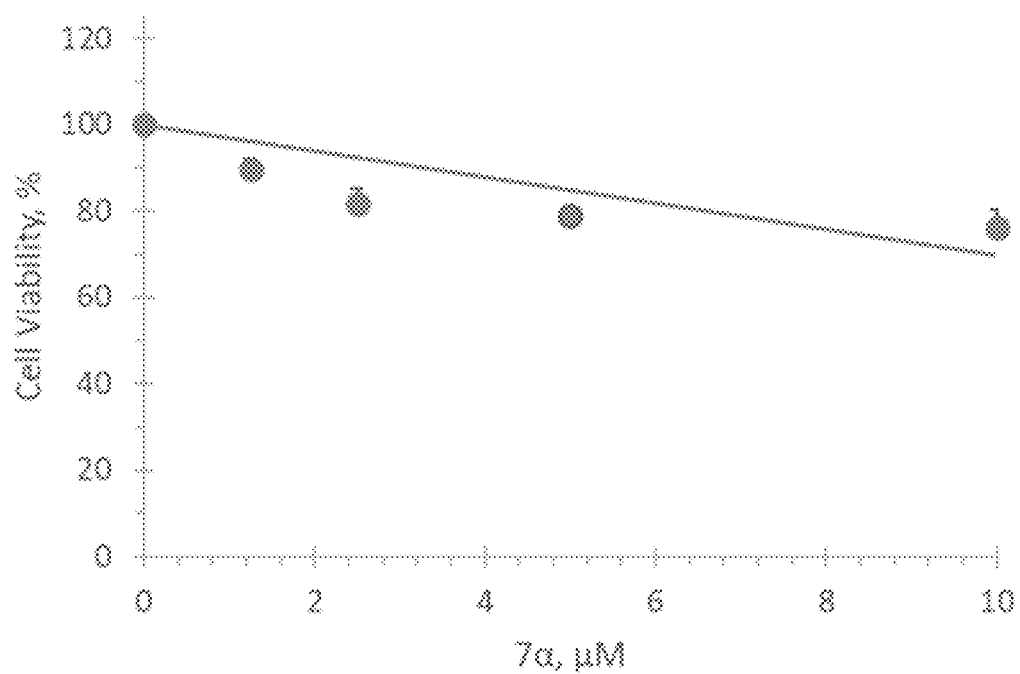
FIG. 17 shows the viability of cultured A549 lung cancer cells in the presence of different concentrations of peptide 7α.

The effect of peptide 7α of viability of A549 lung cancer cells was studied. A549 lung cancer cells (ATCC #CCL-185) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 17 shows that peptide 7α decreases viability of cultured A549 lung cancer cells.

Example 14

Figure 18:
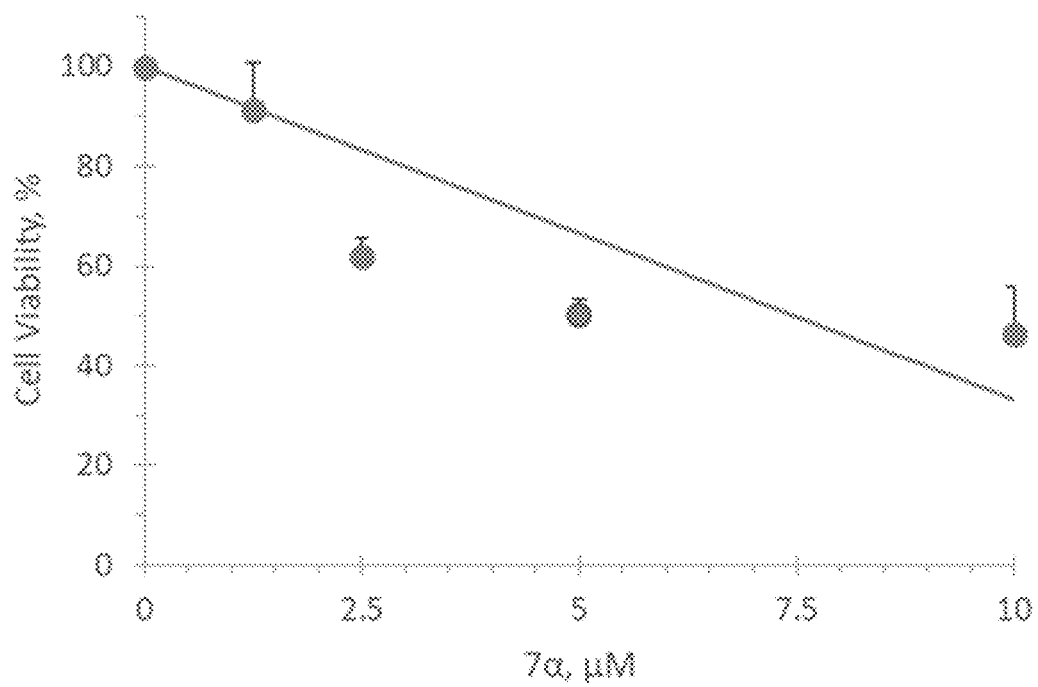
FIG. 18 shows the viability of cultured H596 lung cancer cells in the presence of different concentrations of peptide 7α.

The effect of peptide 7α of viability of H596 lung cancer cells was studied. H596 lung cancer cells (ATCC #HTB-178) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 18 shows that peptide 7α decreases viability of cultured H596 lung cancer cells.

Example 15

Figure 19:
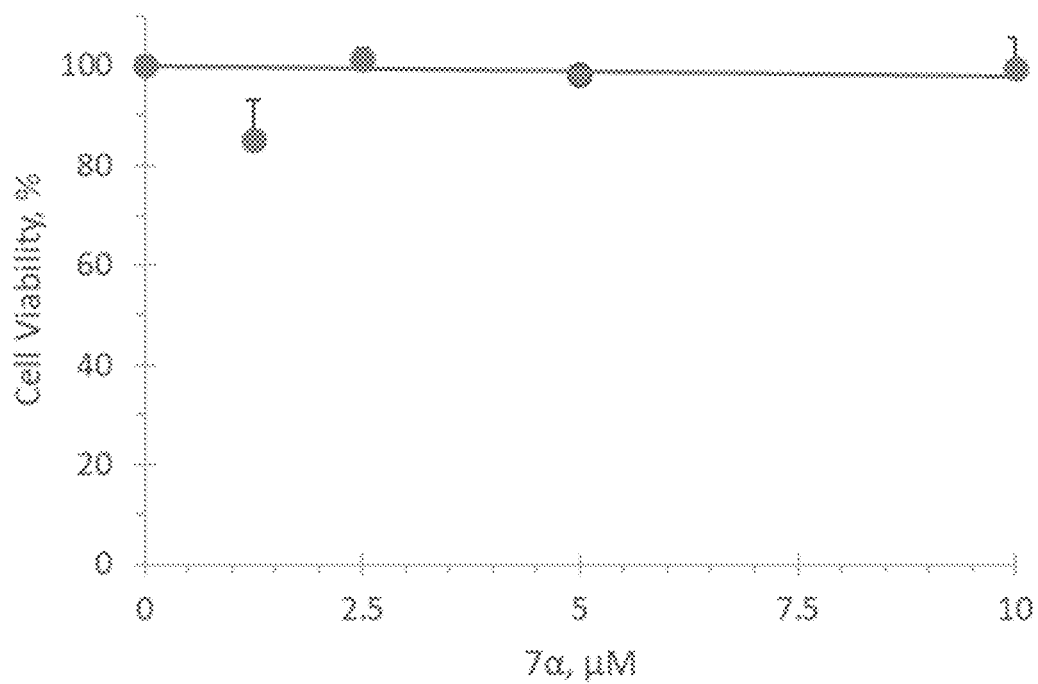
FIG. 19 shows the viability of cultured normal primary lung fibroblasts in the presence of different concentrations of peptide 7α.

The effect of peptide 7α of viability of HLF normal primary lung fibroblasts was studied. HLF normal primary lung fibroblasts (ATCC #PCS-201-013) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 19 shows that peptide 7α does not affect viability of cultured normal primary lung fibroblasts.

Example 16

Figure 20:
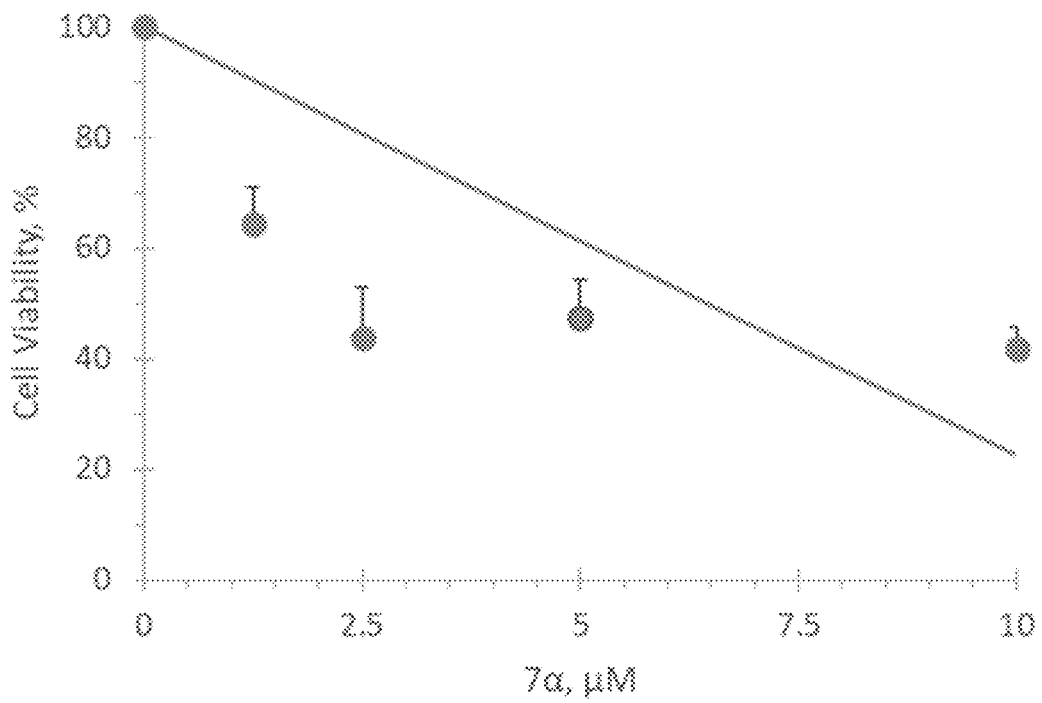
FIG. 20 shows the viability of cultured pancreatic cancer cells in the presence of different concentrations of peptide 7α.

The effect of peptide 7α of viability of pancreatic cancer cells was studied. PANC-1 pancreatic cancer cells (ATCC #CRL-1469) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 20 shows that peptide 7α decreases viability of cultured pancreatic cancer cells.

Example 17

Figure 21:
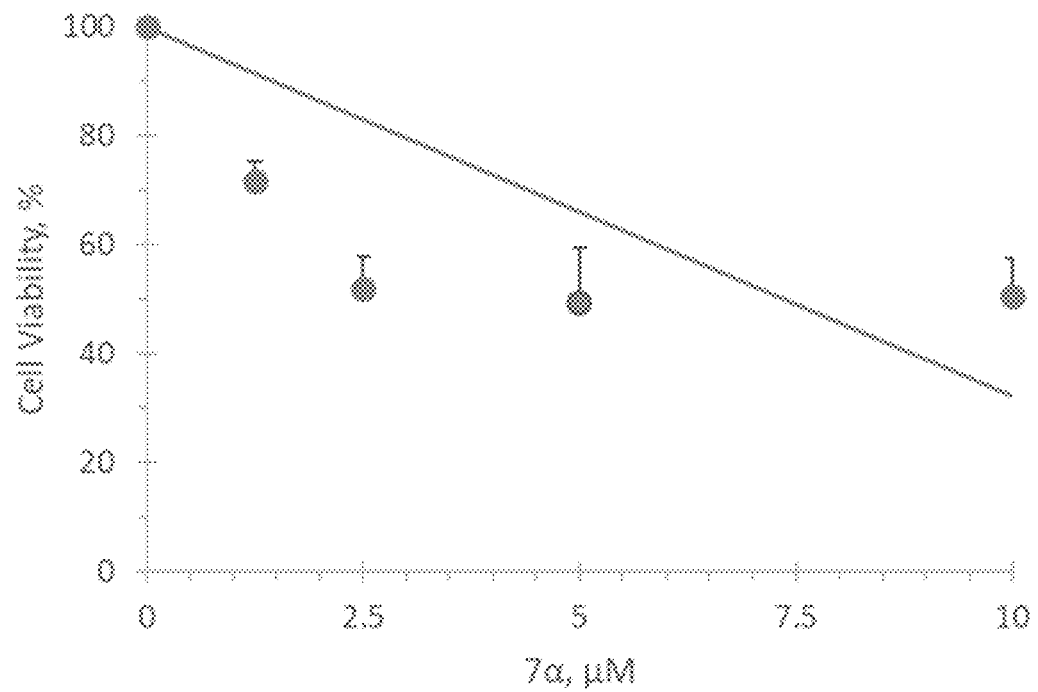
FIG. 21 shows the viability of cultured pancreatic cancer cells in the presence of different concentrations of peptide 7α.

The effect of peptide 7α of viability of pancreatic cancer cells was studied. Hs 766T pancreatic cancer cells (ATCC #HTB-134) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 21 shows that peptide 7α decreases viability of cultured pancreatic cancer cells.

Example 18

Figure 22:
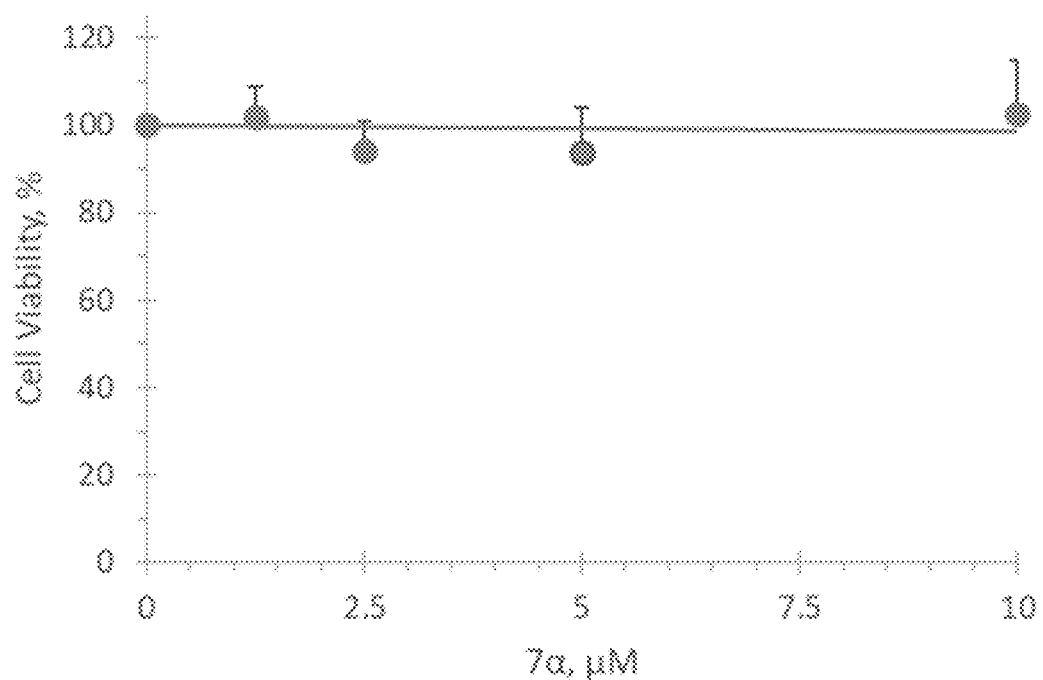
FIG. 22 shows the viability of cultured normal pancreatic cells in the presence of different concentrations of peptide 7α.

The effect of peptide 7α of viability of normal normal pancreatic cells was studied. hTERT-HPNE immortalized normal pancreatic cells (ATCC #CRL-4023) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 22 shows that peptide 7α does not affect viability of cultured normal pancreatic cells.

Example 19

Figure 23:
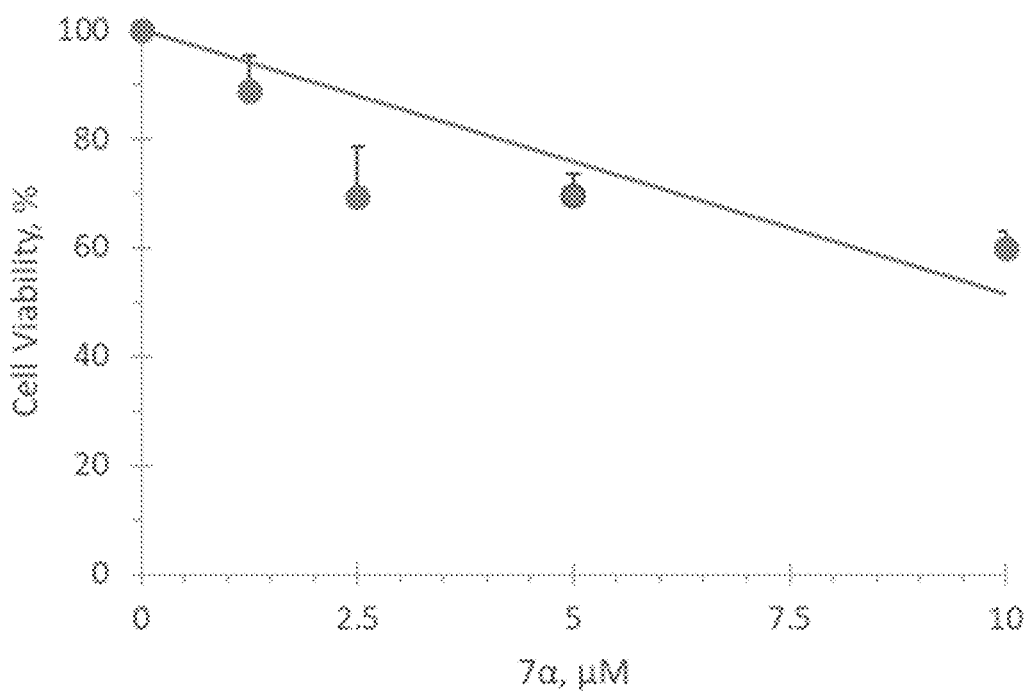
FIG. 23 shows the viability of cultured prostate cancer cells in the presence of different concentrations of peptide 7α.

The effect of peptide 7α of viability of prostate cancer cells was studied. DU145 prostate cancer cells (ATCC #HTB-81) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 23 shows that peptide 7α decreases viability of cultured prostate cancer cells.

Example 20

Figure 24:
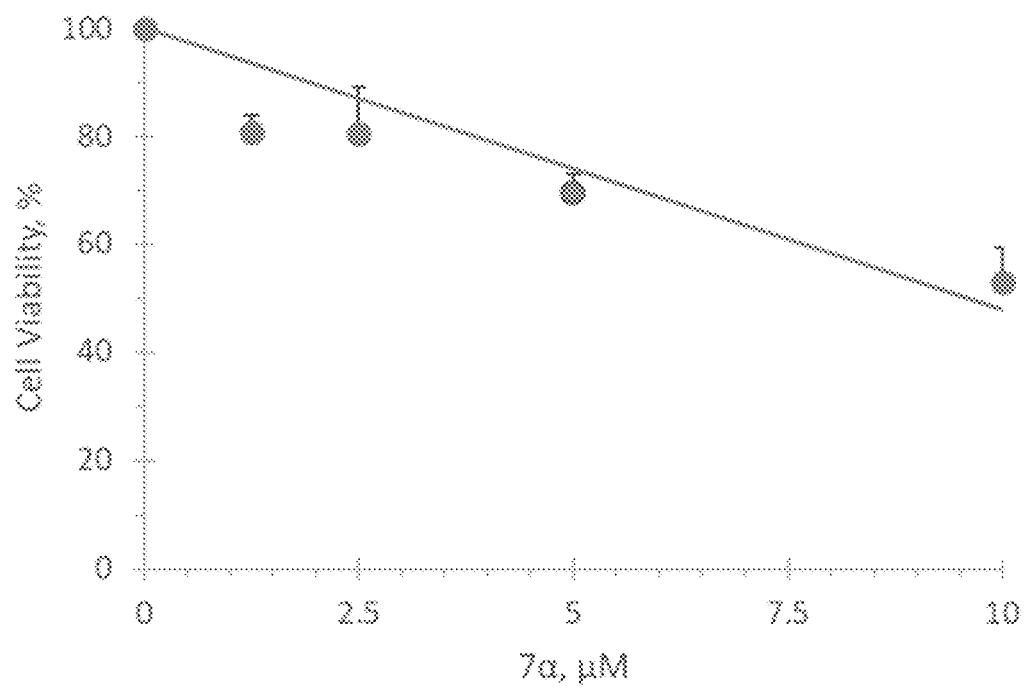
FIG. 24 shows the viability of cultured prostate cancer cells in the presence of different concentrations of peptide 7α.

The effect of peptide 7α of viability of prostate cancer cells was studied. PC3 prostate cancer cells (ATCC #CRL-1435) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 24 shows that peptide 7α decreases viability of cultured prostate cancer cells.

Example 21

Figure 25:
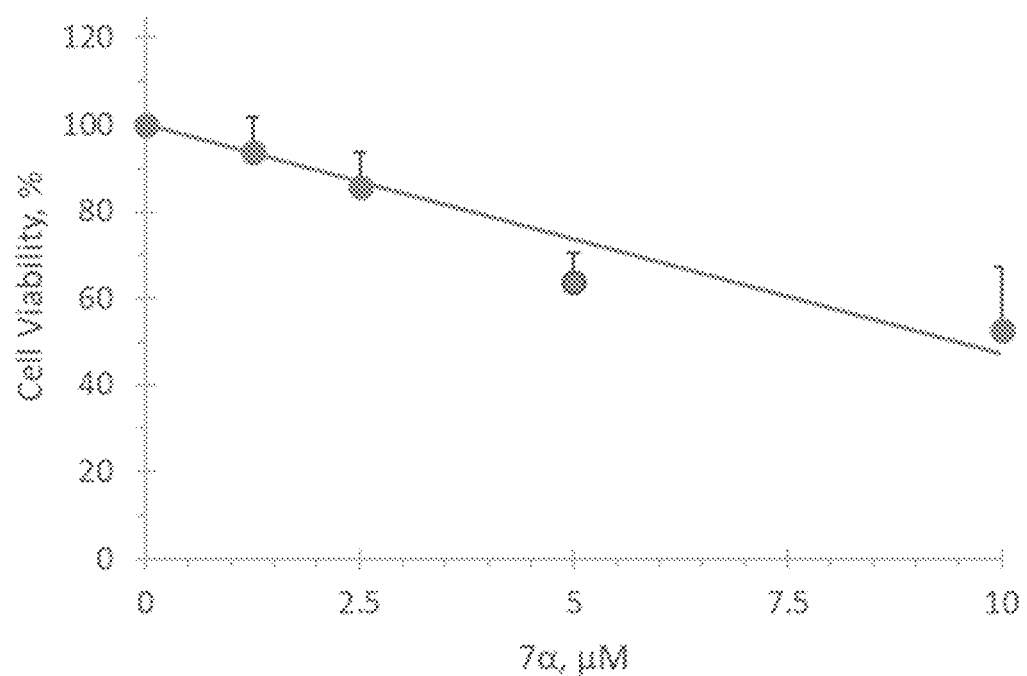
FIG. 25 shows the viability of cultured colorectal cancer cells in the presence of different concentrations of peptide 7α.

The effect of peptide 7α of viability of colorectal cancer cells was studied. HCT-116 colorectal cancer cells (ATCC #CCL-247) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 25 shows that peptide 7α decreases viability of cultured colorectal cancer cells.

Example 22

Figure 26:
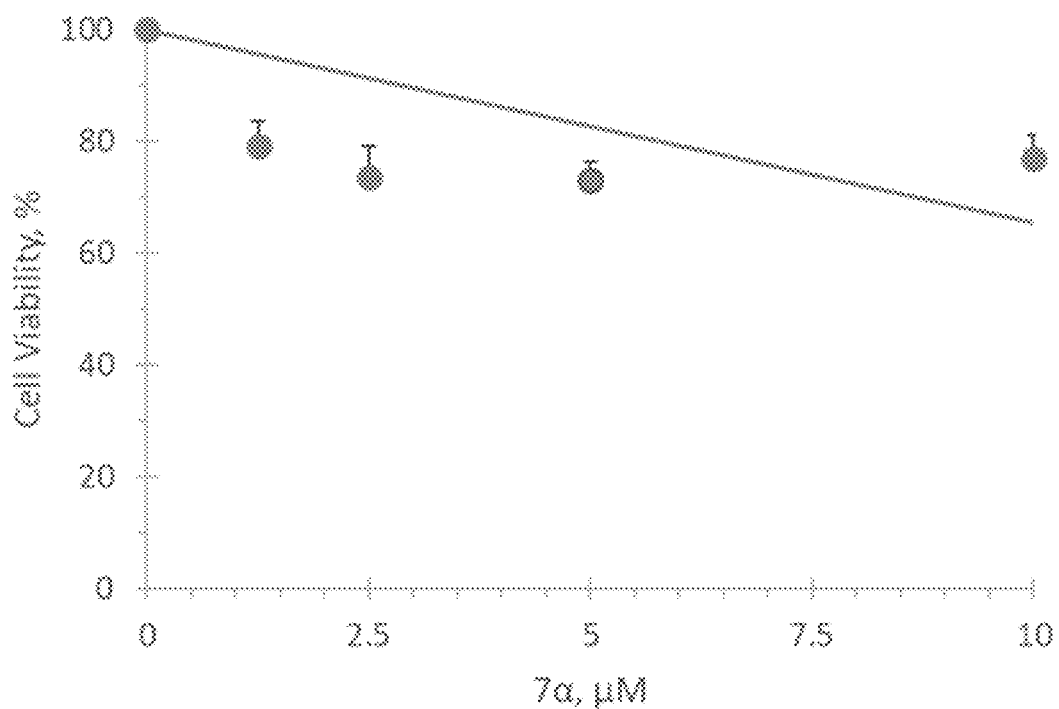
FIG. 26 shows the viability of cultured osteosarcoma cancer cells in the presence of different concentrations of peptide 7α.

The effect of peptide 7α of viability of osteosarcoma cancer cells was studied. U-2OS osteosarcoma cancer cells (ATCC #HTB-96) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 26 shows that peptide 7α decreases viability of cultured osteosarcoma cancer cells.

Example 23

Figure 27:
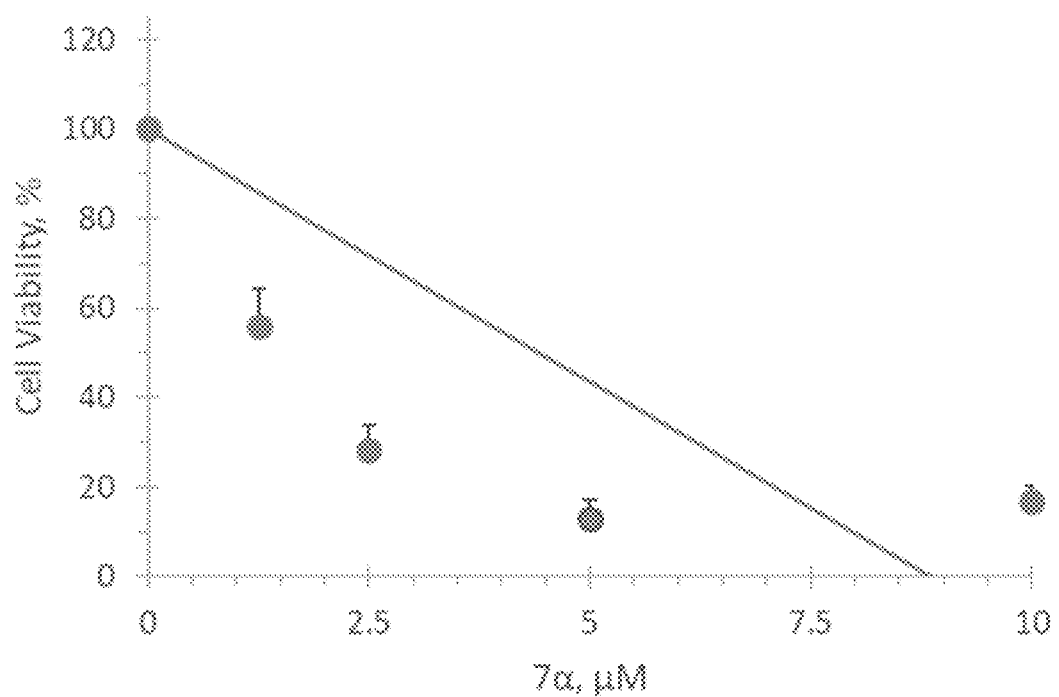
FIG. 27 shows the viability of cultured fibrosarcoma cancer cells in the presence of different concentrations of peptide 7α.

The effect of peptide 7α of viability of fibrosarcoma cancer cells was studied. HT1080 fibrosarcoma cancer cells (ATCC #CCL-121) were transfected with 1.25-10 μM peptide 7α for 3.5 hrs, incubated in a complete media for a duration of two doubling times, and assessed for viability by using a CCK-8 colorimetric assay (Dojindo Molecular Technologies, Inc.). FIG. 27 shows that peptide 7α decreases viability of cultured fibrosarcoma cancer cells.

Example 24

Figure 28:
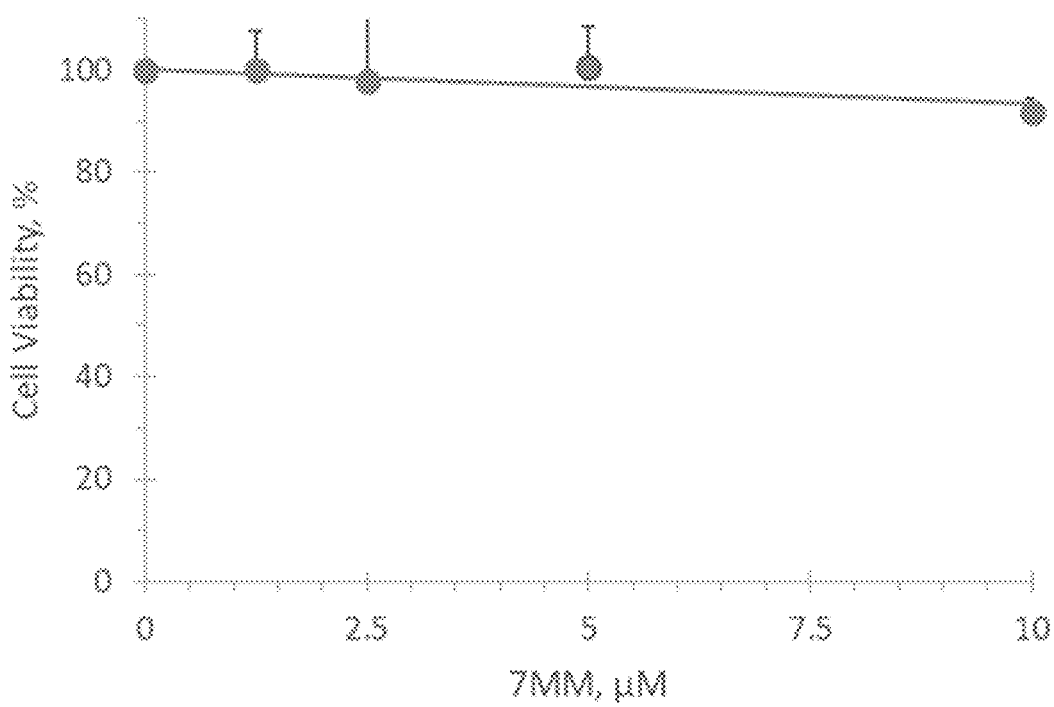
FIG. 28 shows the viability of cultured normal breast cells in the presence of different concentrations of Peptide 7MM.

The effect of peptide 7MM of viability of normal epithelial breast cells was studied. HMEC primary normal epithelial breast cells (ATCC #PCS-600-010) were transfected with 1.25-10 μM peptide 7MM for 3.5 hrs, incubated in a complete media for a duration of two doubling times, and assessed for viability by using a CCK-8 colorimetric assay (Dojindo Molecular Technologies, Inc.). FIG. 28 shows that peptide 7MM does not affect viability of cultured normal breast cells.

Example 25

Figure 29:
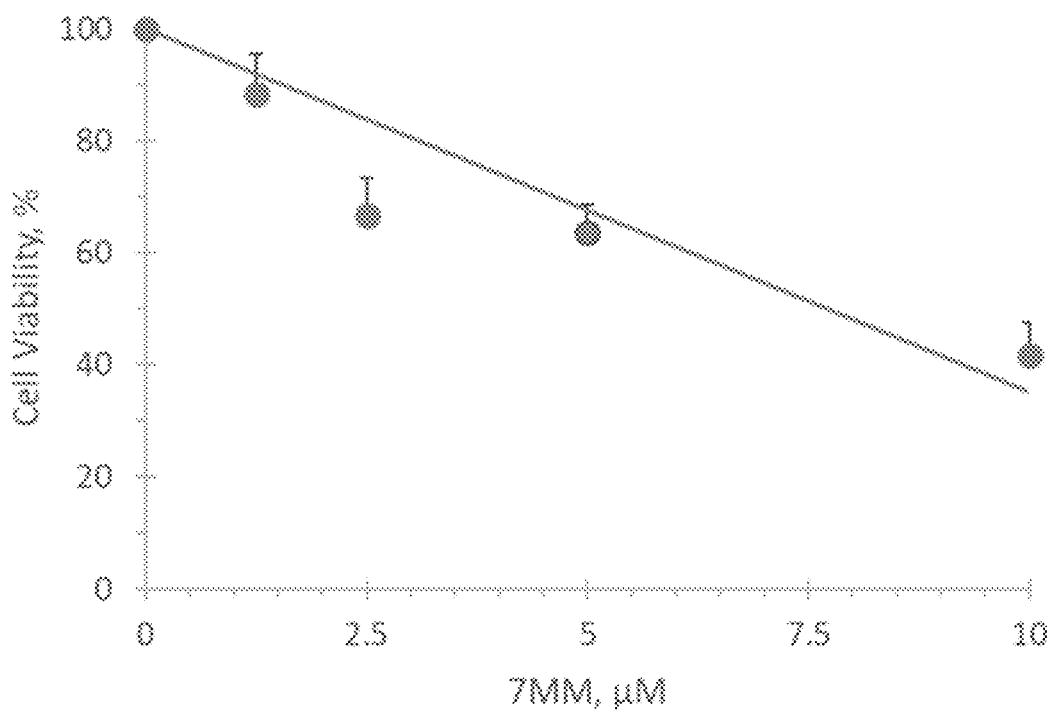
FIG. 29 shows the viability of cultured glioma cells in the presence of different concentrations of Peptide 7MM.

The effect of peptide 7MM of viability of glioma cancer cells was studied. M059J glioma cancer cells (ATCC #CRL-2366) were transfected with 1.25-10 μM peptide 7MM for 3.5 hrs, incubated in a complete media for a duration of two doubling times, and assessed for viability by using a CCK-8 colorimetric assay (Dojindo Molecular Technologies, Inc.). FIG. 29 shows that peptide 7MM decreases viability of cultured glioma cells Example 26

Figure 30:
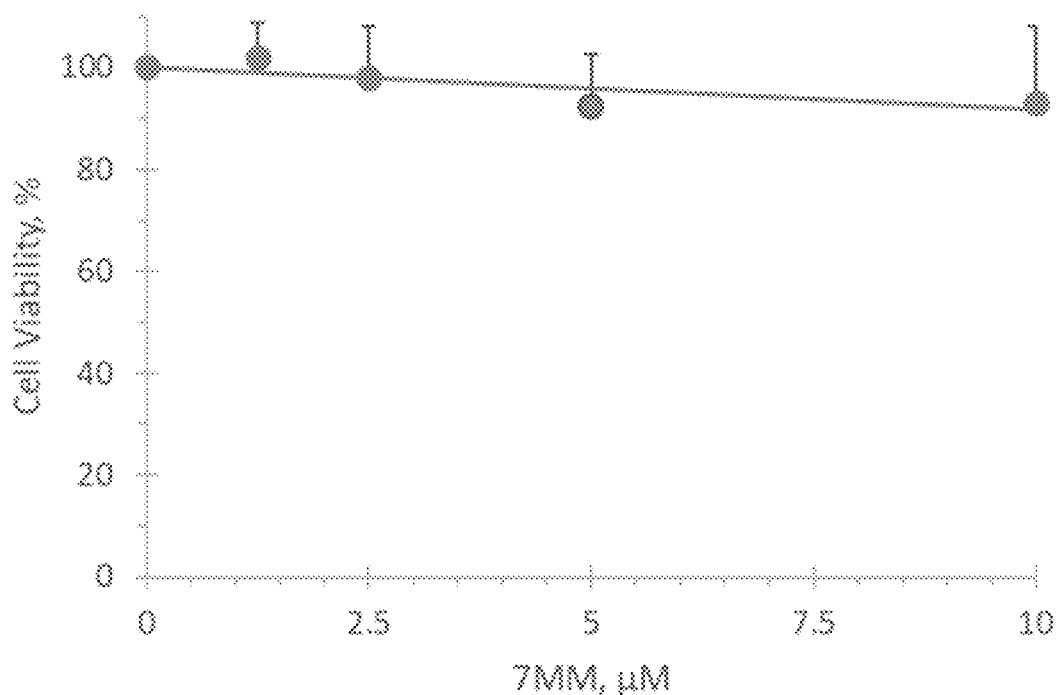
FIG. 30 shows the viability of cultured normal glial cells in the presence of different concentrations of Peptide 7MM.

The effect of peptide 7MM of viability of normal glial cells was studied. SVG p12 normal immortalized glial cells (ATCC #CRL-8621) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 30 shows that peptide 7MM does not affect viability of cultured normal glial cells.

Example 27

Figure 31:
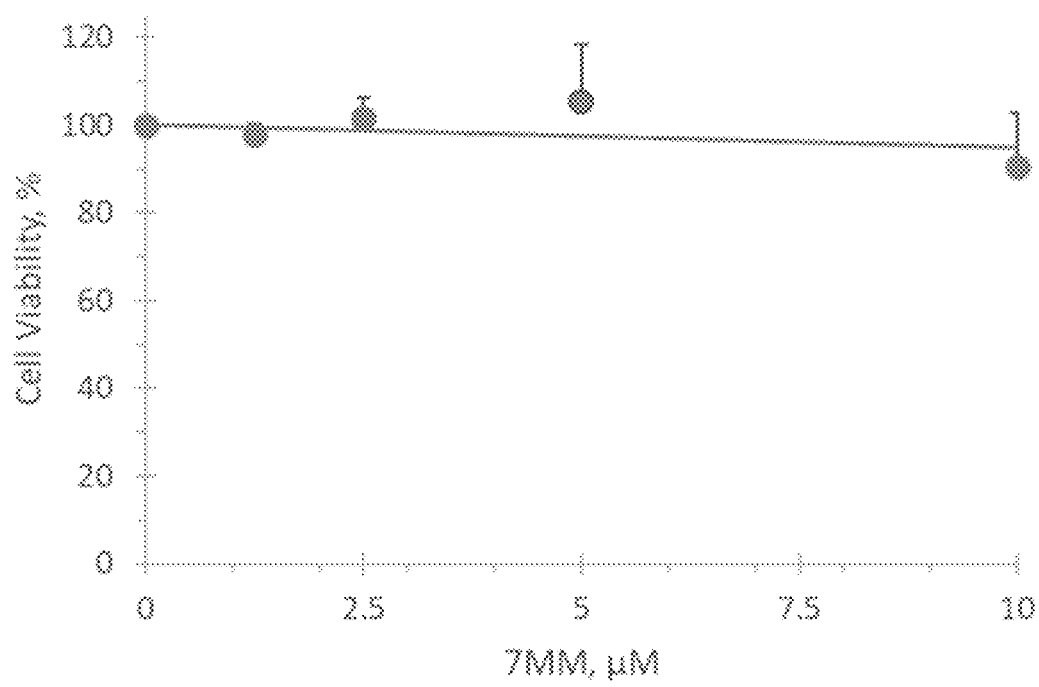
FIG. 31 shows the viability of cultured normal liver cells in the presence of different concentrations of Peptide 7MM.

The effect of peptide 7MM of viability of normal liver cells was studied. THLE-3 normal immortalized liver cells (ATCC #HB-8065) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 31 shows that peptide 7MM does not affect viability of cultured normal liver cells.

Example 28

Figure 32:
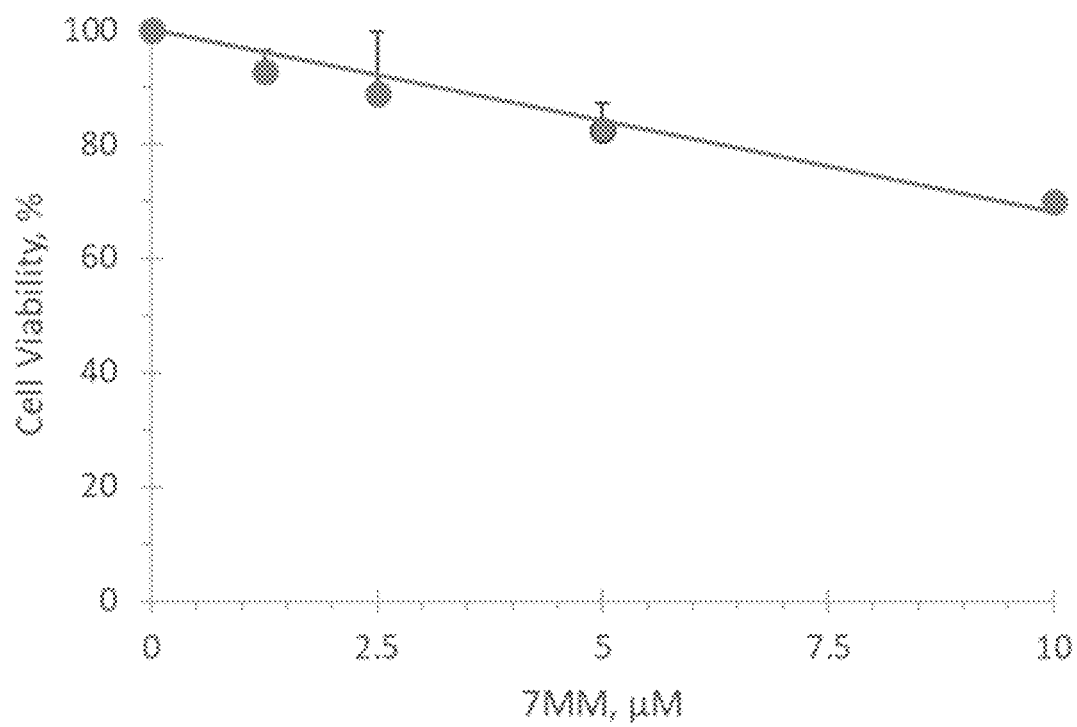
FIG. 32 shows the viability of cultured lung cancer cells in the presence of different concentrations of Peptide 7MM.

The effect of peptide 7MM of viability of lung cancer cells was studied. A549 lung cancer cells (ATCC #CCL-185) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 32 shows that peptide 7MM decreases viability of cultured lung cancer cells.

Example 29

Figure 33:
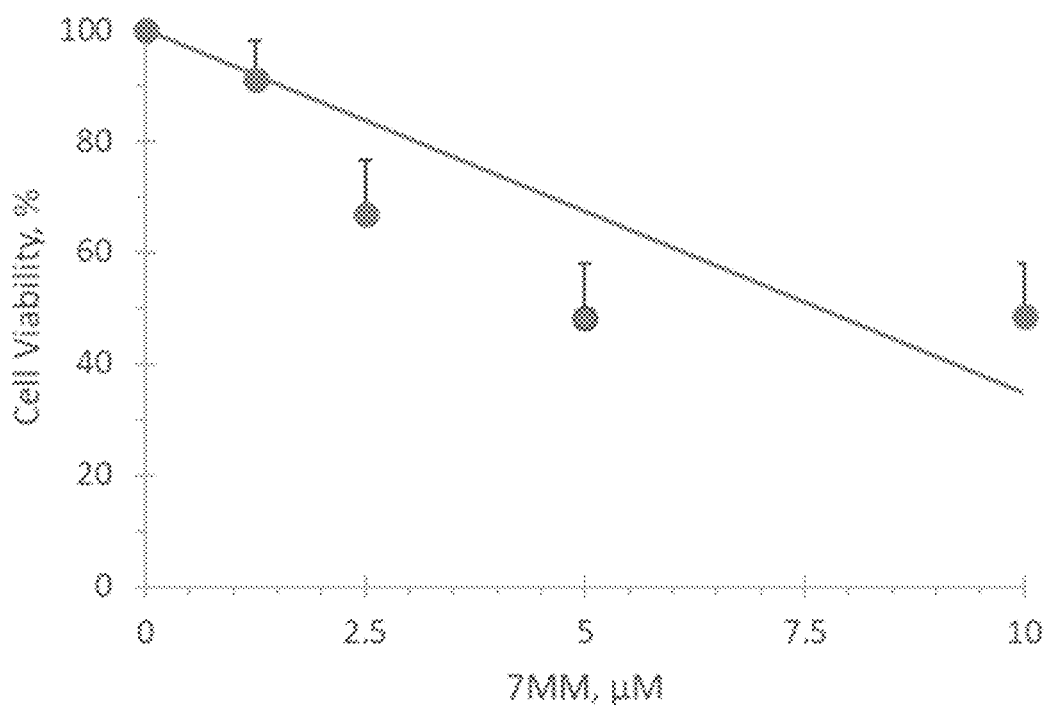
FIG. 33 shows the viability of cultured lung cancer cells in the presence of different concentrations of Peptide 7MM.

The effect of peptide 7MM of viability of lung cancer cells was studied. H596 lung cancer cells (ATCC #HTB-178) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 33 shows that peptide 7MM decreases viability of cultured lung cancer cells.

Example 30

Figure 34:
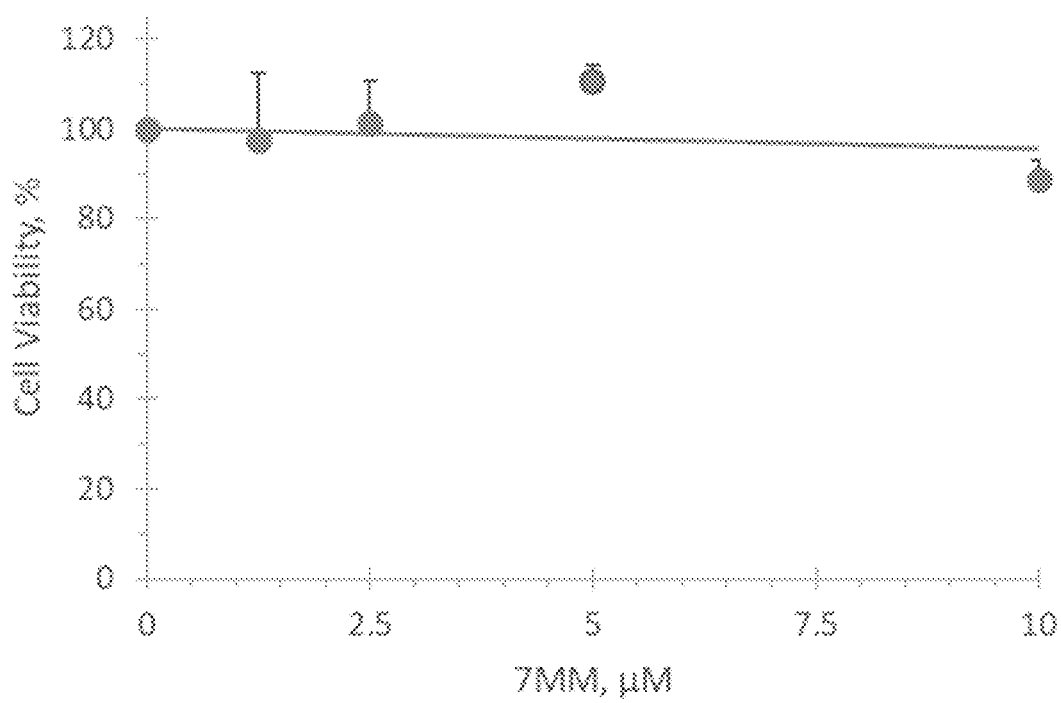
FIG. 34 shows the viability of cultured normal lung cells in the presence of different concentrations of Peptide 7MM.

The effect of peptide 7MM of viability of normal lung cells was studied. HLF normal primary lung fibroblasts (ATCC #PC S-201-013) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 34 shows that peptide 7MM does not affect viability of cultured normal lung cells.

Example 31

Figure 35:
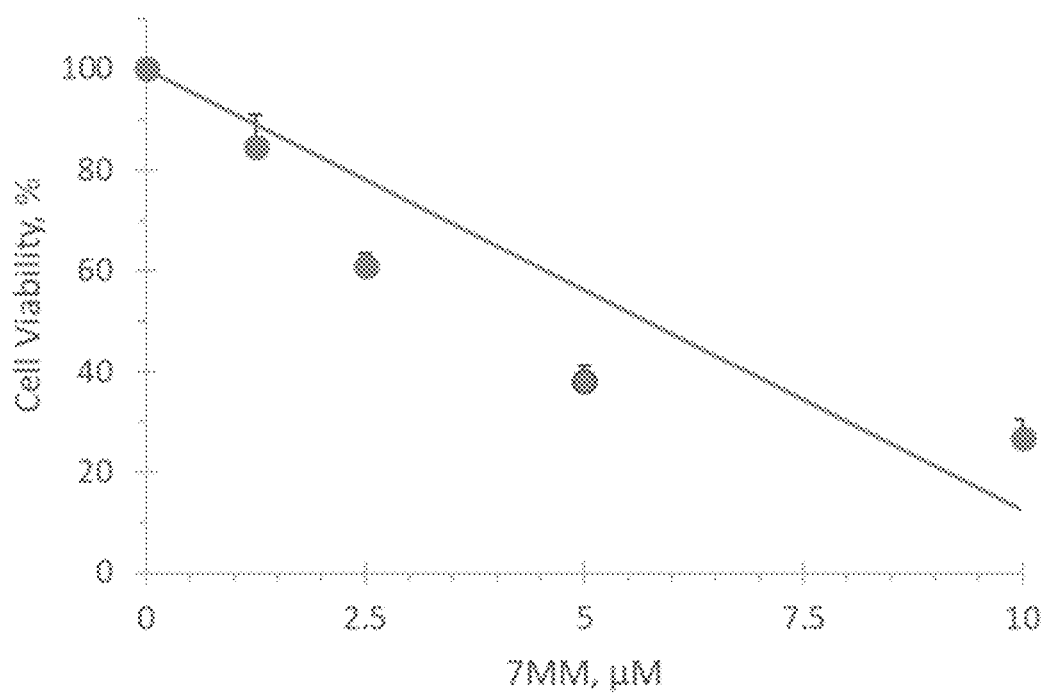
FIG. 35 shows the viability of cultured pancreatic cancer cells in the presence of different concentrations of Peptide 7MM.

The effect of peptide 7MM of viability of pancreatic cancer cells was studied. Hs 766T pancreatic cancer cells (ATCC #HTB-134) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 35 shows that peptide 7MM decreases viability of cultured pancreatic cancer cells.

Example 32

Figure 36:
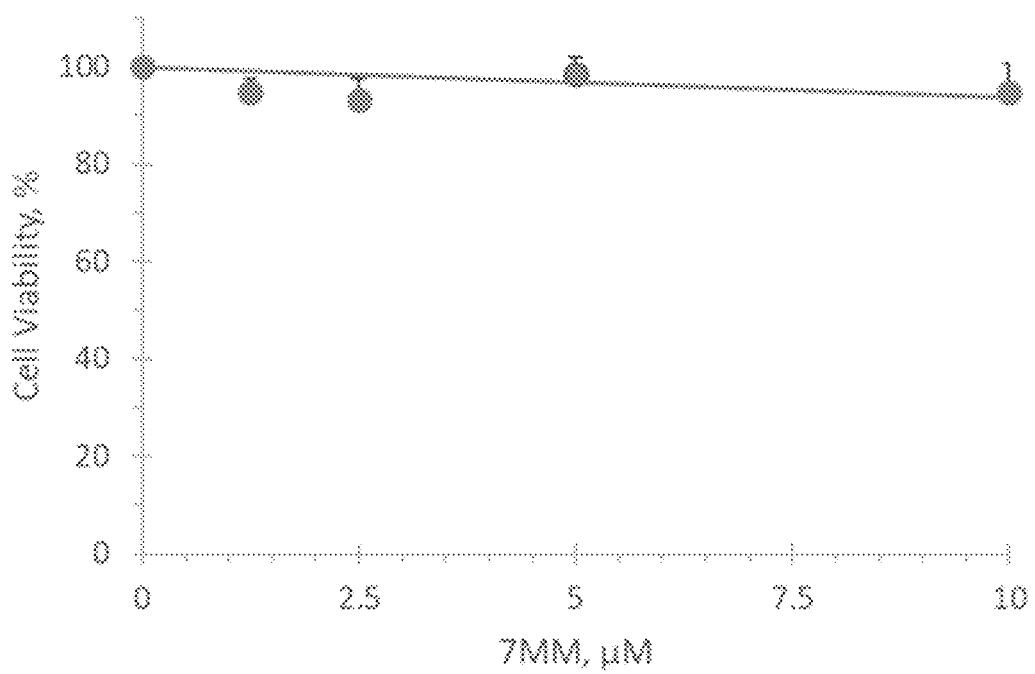
FIG. 36 shows the viability of cultured normal pancreatic cells in the presence of different concentrations of Peptide 7MM.

The effect of peptide 7MM of viability of normal pancreatic cells was studied. hTERT-HPNE normal immortalized pancreatic cells (ATCC #CRL-4023) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 36 shows that peptide 7MM does not affect viability of cultured normal pancreatic cells.

Example 33

Figure 37:
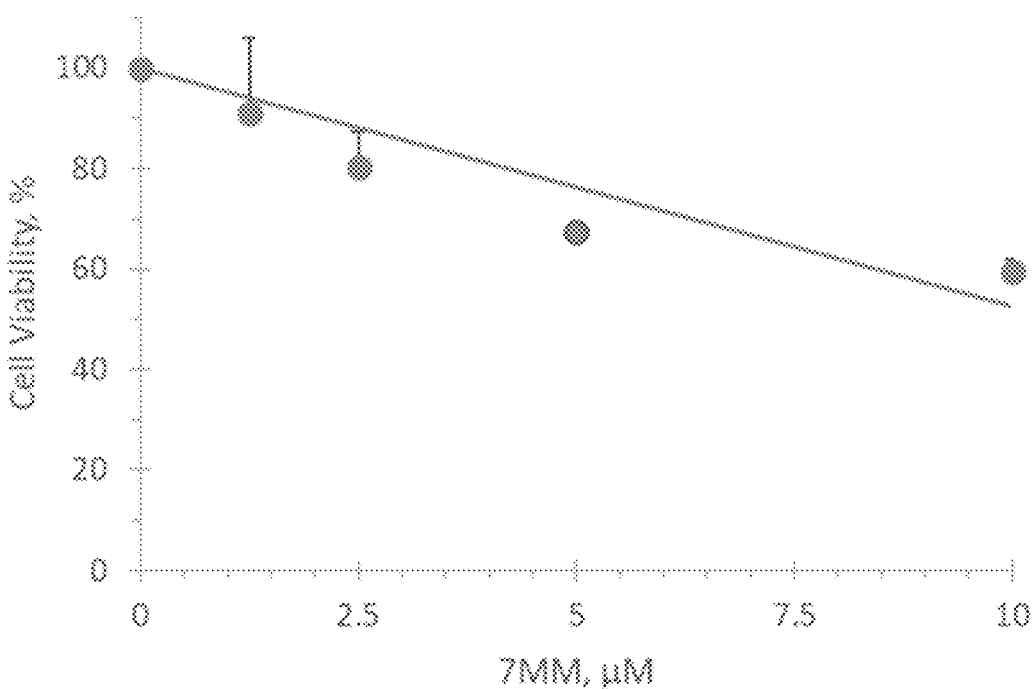
FIG. 37 shows the viability of cultured prostate cancer cells in the presence of different concentrations of Peptide 7MM.

The effect of peptide 7MM of viability of prostate cancer cells was studied. DU145 prostate cancer cells (ATCC #HTB-81) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 37 shows that peptide 7MM decreases viability of cultured prostate cancer cells.

Example 34

Figure 38:
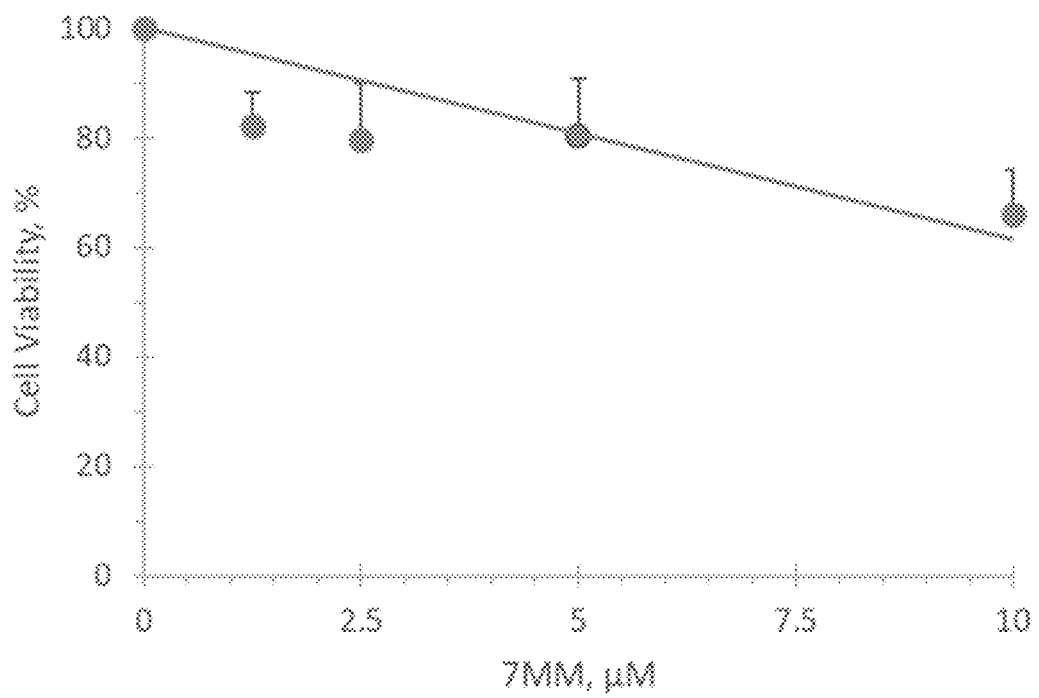
FIG. 38 shows the viability of cultured prostate cancer cells in the presence of different concentrations of Peptide 7MM.

The effect of peptide 7MM of viability of prostate cancer cells was studied. PC3 prostate cancer cells (ATCC #CRL-1435) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 38 shows that peptide 7MM decreases viability of cultured prostate cancer cells.

Example 35

Figure 39:
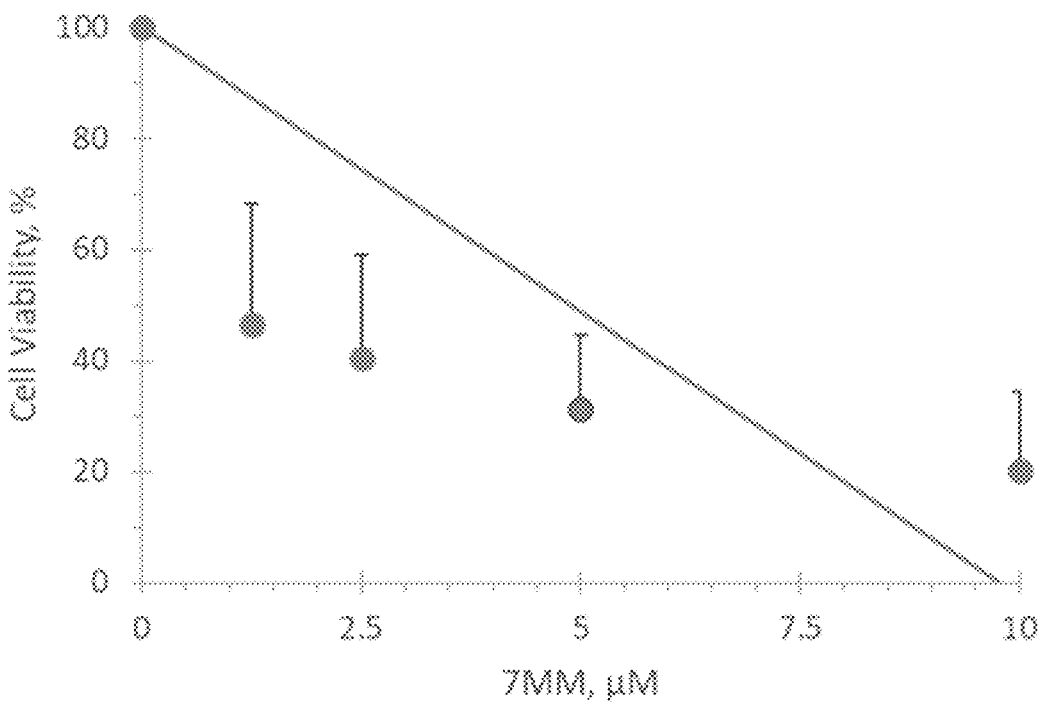
FIG. 39 shows the viability of cultured colorectal cancer cells in the presence of different concentrations of Peptide 7MM.

The effect of peptide 7MM of viability of colorectal cancer cells was studied. HCT-116 colorectal cancer cells (ATCC #CCL-247) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 39 shows that peptide 7MM decreases viability of cultured colorectal cancer cells.

Example 36

Figure 40:
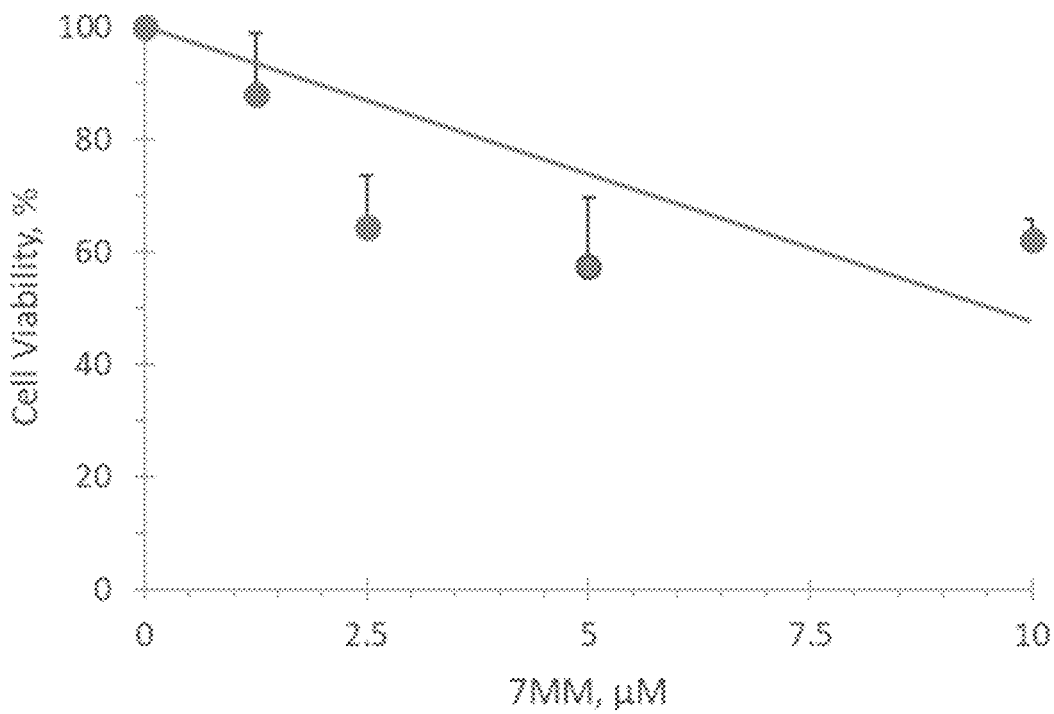
FIG. 40 shows the viability of cultured osteosarcoma cancer cells in the presence of different concentrations of Peptide 7MM.

The effect of peptide 7MM of viability of osteosarcoma cancer cells was studied. U-2 OS osteosarcoma cancer cells (ATCC #HTB-96) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 40 shows that peptide 7MM decreases viability of cultured osteosarcoma cancer cells.

Example 37

Figure 41:
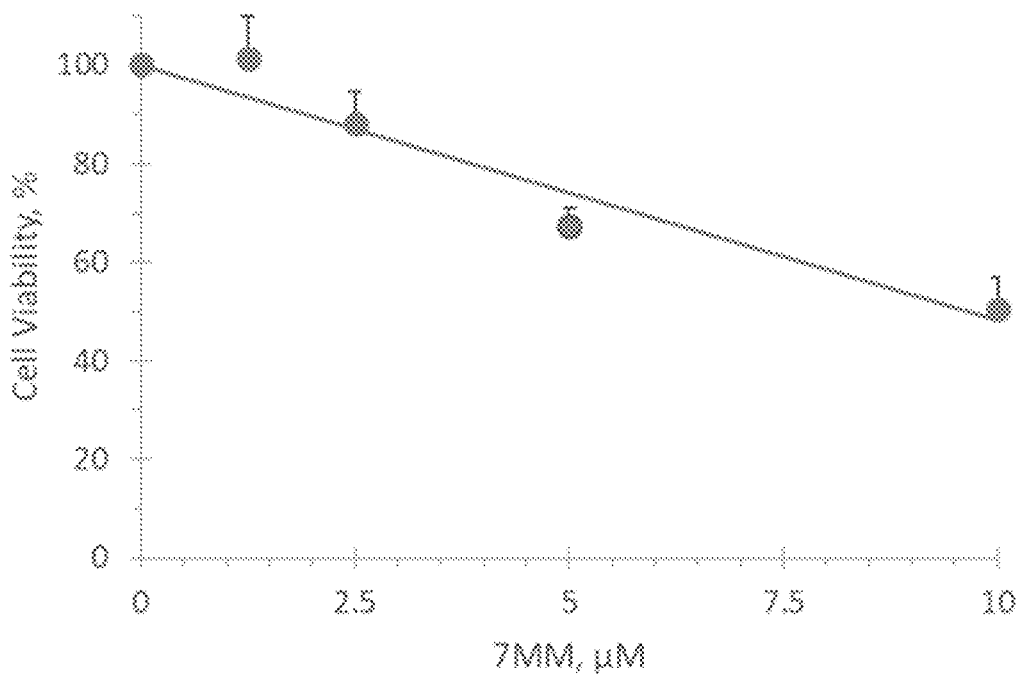
FIG. 41 shows the viability of cultured fibrosarcoma cancer cells in the presence of different concentrations of Peptide 7MM.

The effect of peptide 7MM of viability of fibrosarcoma cancer cells studied. HT1080 fibrosarcoma cancer cells (ATCC #CCL-121) were transfected with 1.25-10 µM peptide 7MM for 3.5 hrs, incubated in a complete media for a duration of two doubling times, and assessed for viability by using a CCK-8 colorimetric assay (Dojindo Molecular Technologies, Inc.). FIG. 41 shows that peptide 7MM decreases viability of cultured fibrosarcoma cancer cells.

Example 38

Table 1 shows concentrations of peptide 7α, 7MM, and 7M at which viabilities of cell lines were reduced to 50%. IC50 values were calculated from obtained equations that describe cell viability as a function of peptide concentration.

TABLE 1

| IC50, μM | | 7α | 7MM | 7M |
|---|---|---|---|---|
| Cell line type | Cell line name | (18aa) | (7aa) | (13aa) |
| Breast | BT-549 | 4.6 | 6.8 | 6.6 |
| Normal breast | HMEC | 115.1 | 77.5 | — |
| Glioma | M059J | 7.1 | 7.7 | 6.8 |
| Normal glial | SVG p12 | 112.9 | 60.4 | 109.4 |
| Liver | HepG2 | 3.7 | 14.2 | 10 |
| Normal liver | THLE-3 | 118.8 | 100.4 | — |
| Lung | A549 | 16.5 | 15.6 | — |
| Lung | H596 | 7.5 | 7.6 | — |
| Normal lung | HLF | 225.3 | 109.7 | — |
| Pacreatic | PANC-1 | 6.4 | 10.1 | 7.4 |
| Pancreatic | Hs766T | 7.4 | 5.7 | — |
| Normal pancreatic | hTERT-HPNE | 366.3 | 79.9 | — |
| Prostate | DU145 | 10.3 | 10.6 | — |
| Prostate | PC3 | 9.6 | 13 | — |
| Colorectal | HCT-116 | 9.5 | 4.9 | — |
| Osteosarcoma | U2OS | 14.5 | 9.6 | — |
| Fibrosarcoma | HT1080 | 4.4 | 9.7 | — |

Example 39

Figure 42:
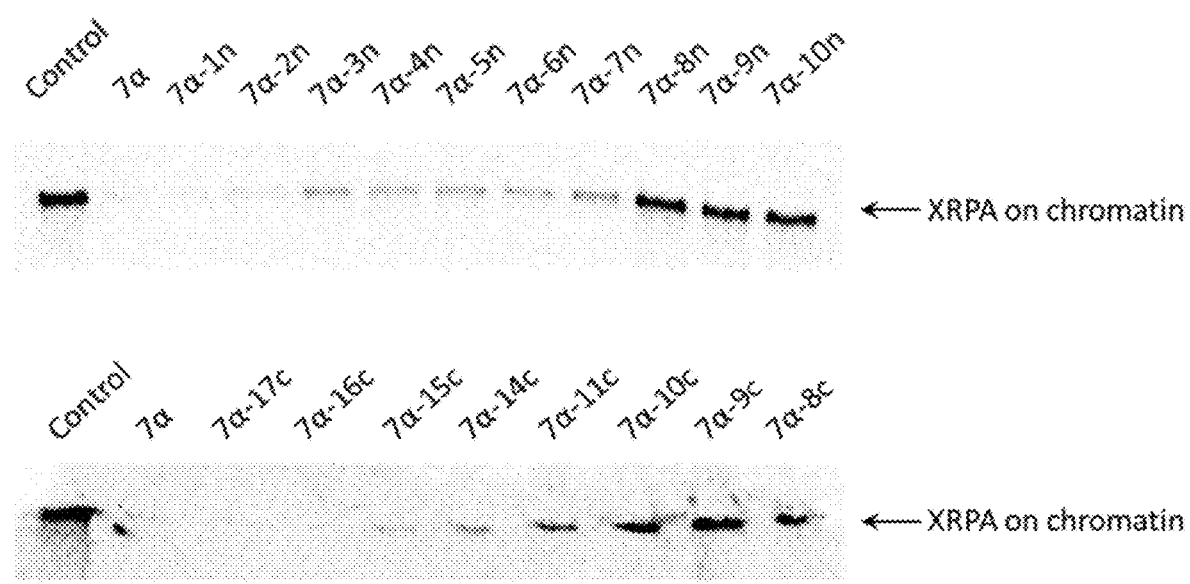
FIG. 42 shows is an image of a Western blot of chromatin isolated from *Xenopus* egg extracts treated with 7a peptide and various 7a truncate peptides (SEQ ID NOs: 22-33) in vitro.

250 μM of each of peptides 7α (DLVISFQLMLCVLDYFIK) (SEQ ID NO: 14), 7α-1n (LVISFQLMLCVLDYFIK) (SEQ ID NO: 22), 7α-2n (VISFQLMLCVLDYFIK) (SEQ ID NO: 23), 7α-3n (ISFQLMLCVLDYFIK) (SEQ ID NO: 24), 7α-4n (SFQLMLCVLDYFIK) (SEQ ID NO: 25), 7α-5n (FQLMLCVLDYFIK) (SEQ ID NO: 26), 7α-6n (QLMLCVLDYFIK) (SEQ ID NO: 27), 7α-7n (LMLCVLDYFIK) (SEQ ID NO: 28), 7α-17c (DLVISFQLMLCVLDYF) (SEQ ID NO: 29), 7α-16c (DLVISFQLMLCVLDY) (SEQ ID NO: 30), 7α-15c (DVISFQLMLCVLD) (SEQ ID NO: 31), 7α-14c (DVISFQLMLCVL) (SEQ ID NO: 32), 7α-11c (DVISFQLML) (SEQ ID NO: 33) was incubated in S phase arrested *Xenopus* egg extracts. Following a 90 min incubation, chromatin was isolated and probed by Western blotting for RPA protein as a readout for DNA helicase activity. FIG. 42 shows that peptides 7α and its truncated versions 7α-1n, 7α-2n, 7α-3n, 7α-4n, 7α-5n, 7α-6n, 7α-7n, 7α-17c, 7α-16c, 7α-15c, 7α-14c, 7α-11c (SEQ ID NOs: 22-33) inhibit CMG helicase in vitro.

Example 40

Figure 43:
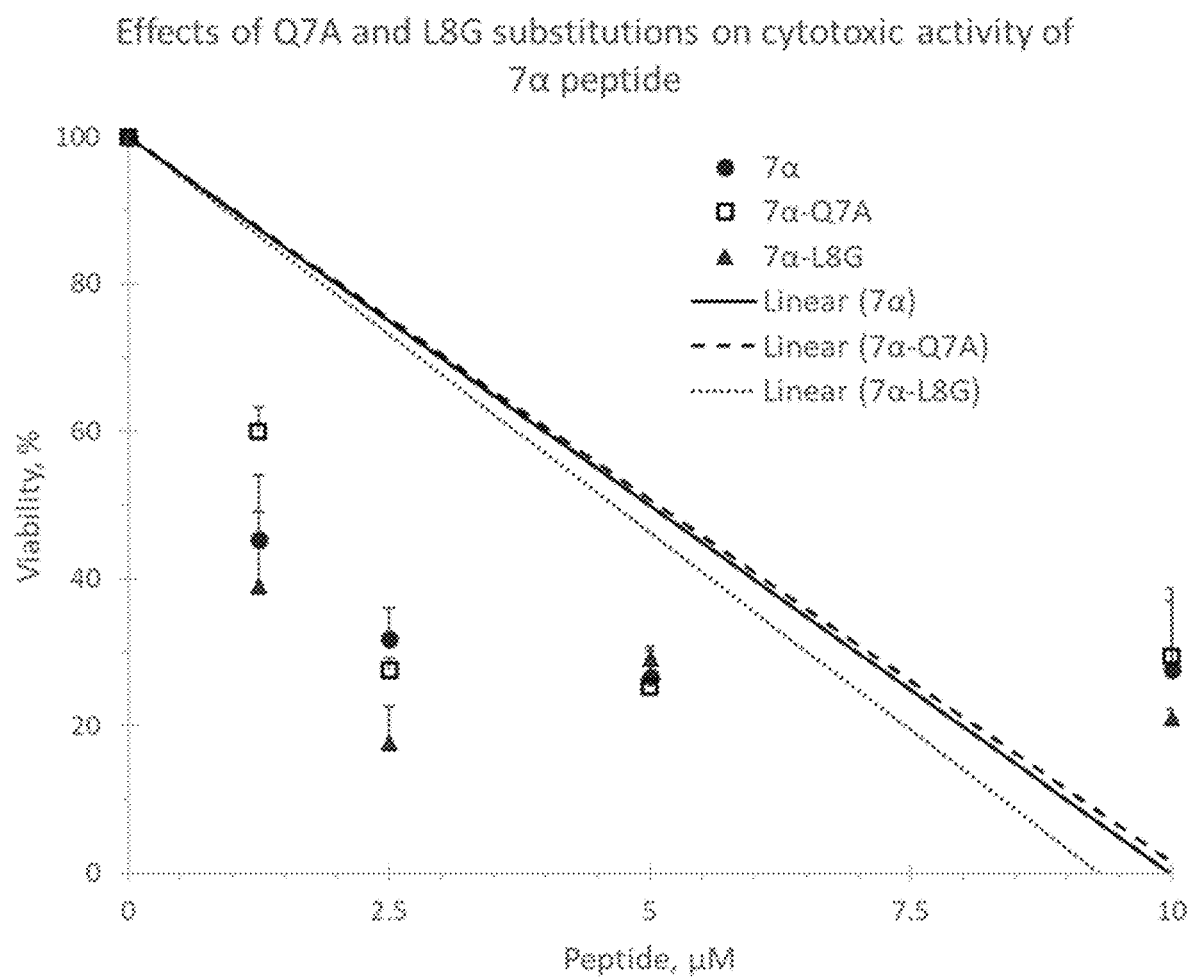
FIG. 43 shows the viability of BT-549 breast cancer cells in the presence of 7a peptide and 7a substituted peptides 7α-Q7A (SEQ ID NO: 34) and 7α-L8G (SEQ ID NO: 35)

BT-549 breast cancer cells (ATCC #HTB-122) were transfected with 1.25-10 of 7 substituted peptides 7α-Q7A (DLVISFALMLCVLDYFIK) (SEQ ID NO: 34) and 7α-L8G (DLVISFQGMLCVLDYFIK) (SEQ ID NO: 35) for 3.5 hrs, incubated in a complete media for a duration of two doubling times, and assessed for viability by using a CCK-8 colorimetric assay (Dojindo Molecular Technologies, Inc.). FIG. 43 shows that 7a substitutions Q7A and L8G inhibit viability of breast cancer cells and do not affect cytotoxicity of peptide 7α.

Example 41

Figure 44:
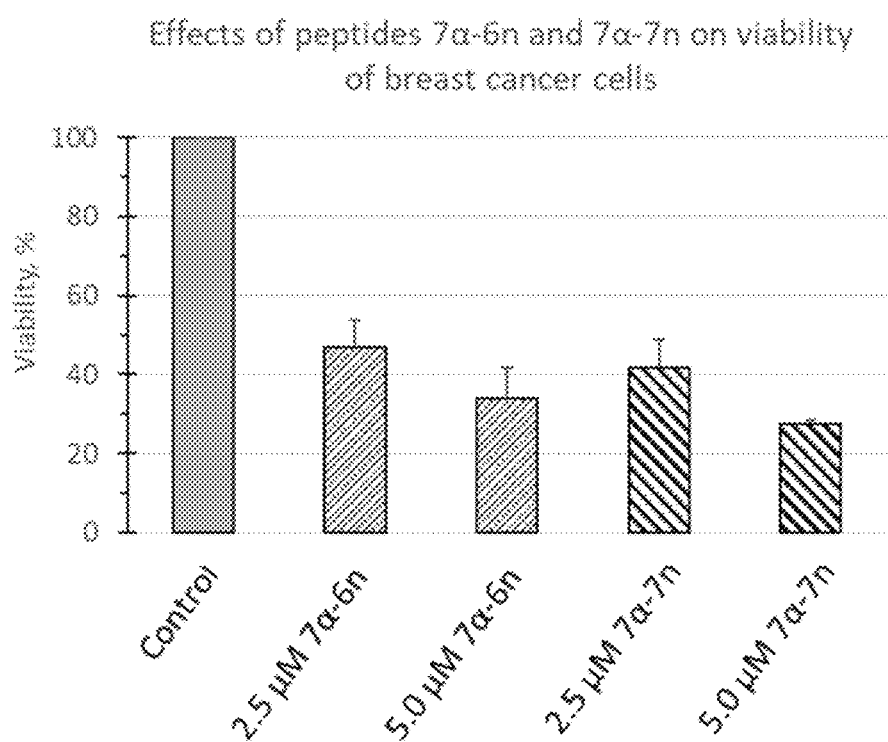
FIG. 44 shows the viability of BT-549 breast cancer cells in the presence of two concentrations of 7a truncate peptides 7α-6n (SEQ ID NO: 27) and 7α-7n (SEQ ID NO: 28)

BT-549 breast cancer cells (ATCC #HTB-122) were transfected with 2.5 and 5.0 μM of peptides 7α-6n (QLMLCVLDYFIK) (SEQ ID NO: 27) and 7α-7n (LMLCVLDYFIK) (SEQ ID NO: 28) for 3.5 hrs, incubated in a complete media for a duration of two doubling times, and assessed for viability by using a CCK-8 colorimetric assay (Dojindo Molecular Technologies, Inc.). FIG. 44 shows 7a truncated peptides 7α-6n and 7α-7n decrease viability of cultured BT-549 breast cancer cells.

Example 42

Figure 45:
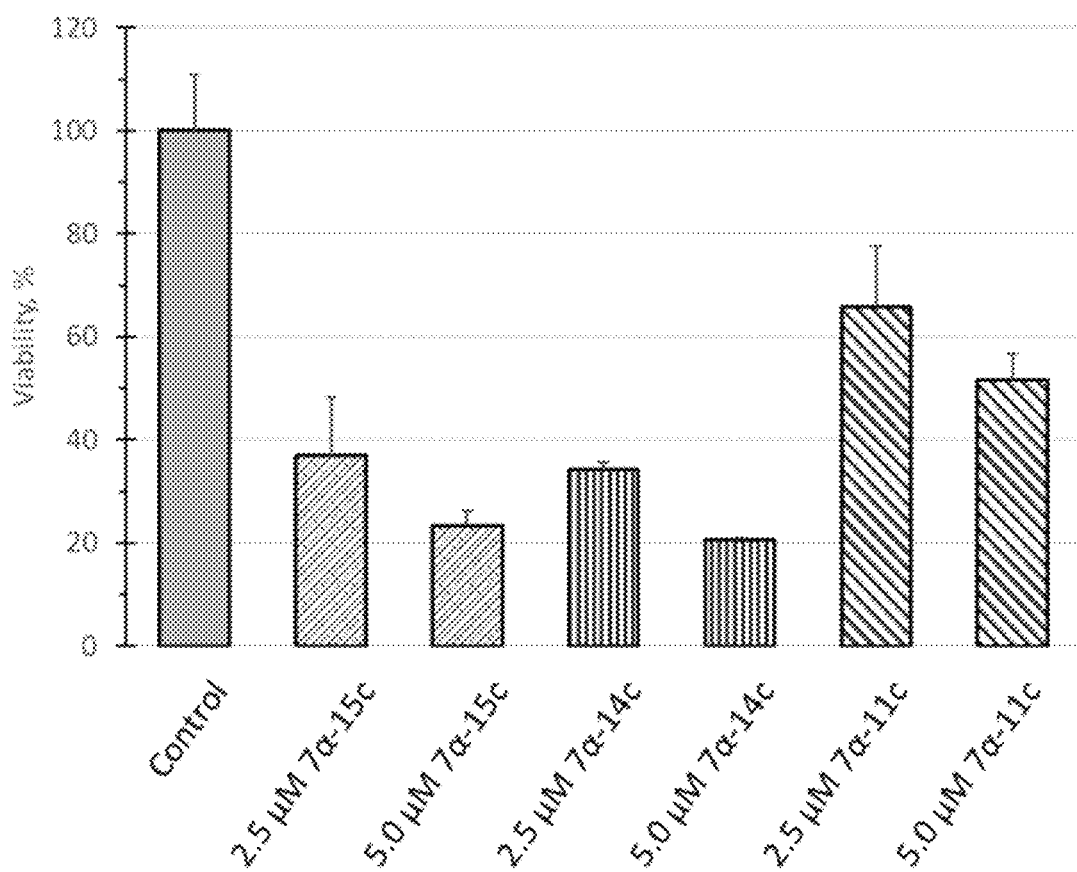
FIG. 45 shows the viability of BT-549 breast cancer cells in the presence of two concentrations of 7a truncate peptides 7α-15c (SEQ ID NO: 31), 7α-14c (SEQ ID NO: 32), and 7α-11c (SEQ ID NO: 33).

BT-549 breast cancer cells (ATCC #HTB-122) were transfected with 2.5 and 5.0 μM of peptides 7α-15c (DLVISFQLMLCVLD) (SEQ ID NO: 31), 7α-14c (DLVISFQLMLCVL) (SEQ ID NO: 32) and 7α-11c (DLVISFQLML) (SEQ ID NO: 33) for 3.5 hrs, incubated in a complete media for a duration of two doubling times, and assessed for viability by using a CCK-8 colorimetric assay (Dojindo Molecular Technologies, Inc.). FIG. 45 shows 7α truncated peptides 7α-15c, 7α-14c, and 7α-11c decrease viability of cultured BT-549 breast cancer cells.

Taking Examples 39, 41, and 42 and generated data of FIGS. 42, 44, and 45, 7α truncates 7α-1n, 7α-2n, 7α-3n, 7α-4n, 7α-5n, 7α-6n, 7α-7n, 7α-17c, 7α-16c, 7α-15c, 7α-14c, 7α-11c (SEQ ID NOs: 22-33) decrease viability of cancer cells. Further, extending from the above and other findings herein, 7MM (SEQ ID NO: 2) peptide variants 7MM-G2 (QGMLCVL) (SEQ ID NO: 36), 7MM-G4 (QLMGCVL) (SEQ ID NO: 37), 7MM-D (QLMLCVLD) (SEQ ID NO: 38), 7MM6 (LMLCVL) (SEQ ID NO: 39), 7MM6-G2 (GMLCVL) (SEQ ID NO: 40), 7MM6-G4 (LMGCVL) (SEQ ID NO: 41), 7MM6-D (LMLCVLD) (SEQ ID NO: 42), 7MM6-G2-D (GMLCVLD) (SEQ ID NO: 43), and 7MM6-G4-D (LMGCVLD) (SEQ ID NO: 44) similarly inhibit CMG helicase and decrease viability of cancer cells.

These results support the idea of targeting CMG helicase for cancer treatment and developing novel anti-cancer therapeutic agents based on peptides disclosed herein.

In various embodiments, a protein comprising or consisting of the amino acid sequence of SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or a retro-inversion, functional homologue, or a conservative substituted version inversion thereof reduces viability of cancer cells according to the method described in the examples wherein the IC50 value is about 20 or less, such as less than about 15, less than about 12, less than about 9, less than about 6, less than about 3, less than 1, between about 20 and about 0, between about 20 and about 5, between about 20 and about 10, between about 20 and about 15, between about 15 and about 0, between about 15 and about 5, between about 15 and about 10, between about 10 and about 0.1, between about 10 and about 5, or between about 5 and about 0.1. In some embodiments, the viability of associated noncancer cells is associated with an IC50 value of greater than about 60, greater than about 80, greater than about 100, greater than about 120, greater than about 150, or greater than about 200.

In some embodiments, the peptide consists of or comprises a peptide having the amino acid sequence of SEQ ID NO: 1, SEQ ID NO: 2, or SEQ ID NO: 14 comprising one or more conservative substitutions wherein the peptide effectively inhibits CMG helicase or otherwise affects the viability of cancer cells as determined by utilization of the methodology of Examples 2-43 wherein the IC50 value is about 20 or less, such as less than about 15, less than about 12, less than about 9, less than about 6, less than about 3, between about 20 and about 0, between about 20 and about 5, between about 20 and about 10, between about 20 and about 15, between about 15 and about 0.1, between about 15 and about 5, between about 15 and about 10, between about 10 and about 0.1, between about 10 and about 5, or between about 5 and about 0.1. In some embodiments, the peptide including one or more conservative substitutions disproportionately affects the viability of cancer cells according to the above identified IC50 values compared to corresponding non-cancer cells, wherein viability of the noncancer cells is associated with an IC50 value of greater than about 60, greater than about 80, greater than about 100, greater than about 120, greater than about 150, or greater than about 200.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a peptide" is intended to include "at least one peptide" or "one or more peptides."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is, therefore, intended that such changes and modifications be covered by the appended claims.

What is claimed is:

1. A peptide consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44 or retro-inversion peptides thereof, wherein the C-terminus, N-terminus, or both of the selected amino acid sequence is optionally flanked by one or more additional amino acids, and wherein the one or more additional amino acids are selected from random amino acids or other amino acids that promote cell internalization or nuclear localization and are not native C-terminus or N-terminus flanking sequences of the selected amino acid sequence as registered with amino acid sequence of human retinoblastoma tumor suppressor protein.

2. The peptide of claim 1, wherein the amino acid sequence is SEQ ID NO: 22, SEQ ID NO: 23, SEQ ID NO: 24, SEQ ID NO: 25, SEQ ID NO: 26, SEQ ID NO: 27, or SEQ ID NO: 28.

3. The peptide of claim 1, wherein the peptide consists of the amino acid sequence of SEQ ID NO: 22, SEQ ID NO: 23, SEQ ID NO: 24, SEQ ID NO: 25, SEQ ID NO: 26, SEQ ID NO: 27, or SEQ ID NO: 28.

4. The peptide of claim 1, wherein the amino acid sequence is SEQ ID NO: 29, SEQ ID NO: 30, SEQ ID NO: 31, SEQ ID NO: 32, or SEQ ID NO: 33.

5. The peptide of claim 1, wherein the peptide consists of the amino acid sequence of SEQ ID NO: 29, SEQ ID NO: 30, SEQ ID NO: 31, SEQ ID NO: 32, or SEQ ID NO: 33.

6. The peptide of claim 1, wherein the amino acid sequence is SEQ ID NO: 34 or SEQ ID NO: 35.

7. The peptide of claim 1, wherein the amino acid sequence is SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

8. The peptide of claim 1, wherein the peptide consists of the amino acid sequence of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

9. The peptide of claim 1, wherein the amino acid sequence further comprises a sulfhydryl group at a N or C terminus of the amino acid sequence.

10. The peptide of claim 1, wherein the peptide is labeled with a detectable label, contained in a composition including a pharmaceutically acceptable carrier, or conjugated to a cytotoxic molecule, a radioactive molecule, a hydrophilic group, or a hydrophobic group.

11. A method of inhibiting CMG helicase function comprising contacting a cell with a helicase-inhibiting amount of a peptide consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44 or retro-inversion peptides thereof, wherein the C-terminus, N-terminus, or both of the selected amino acid sequence is optionally flanked by one or more additional amino acids, and wherein the one or more additional amino acids are selected from random amino acids or other amino acids that promote cell internalization or nuclear localization and are not native C-terminus or N-terminus flanking sequences of the selected amino acid sequence as registered with amino acid sequence of human retinoblastoma tumor suppressor protein.

12. A method of treating cancer comprising administering to a subject having cancer with a therapeutically effective amount of a peptide consisting of an amino acid sequence selected from SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44 or retro-inversion peptides thereof, wherein the C-terminus, N-terminus, or both of the selected amino acid sequence is optionally flanked by one or more additional amino acids, and wherein the one or more additional amino acids are selected from random amino acids or other amino acids that promote cell internalization or nuclear localization and are not native C-terminus or N-terminus flanking sequences of the selected amino acid sequence as registered with amino acid sequence of human retinoblastoma tumor suppressor protein, and wherein the cancer is a carcinoma or sarcoma.

13. The method of claim 12, wherein the amino acid sequence is SEQ ID NO: 29, SEQ ID NO: 30, SEQ ID NO: 31, SEQ ID NO: 32, SEQ ID NO: 33, SEQ ID NO: 34, or SEQ ID NO: 35.

14. The method of claim 12, wherein the peptide consists of the amino acid sequence of SEQ ID NO: 29, SEQ ID NO:

30, SEQ ID NO: 31, SEQ ID NO: 32, SEQ ID NO: 33, SEQ ID NO: 34, or SEQ ID NO: 35.

15. The method of claim 12, wherein the amino acid sequence is SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

16. The method of claim 12, wherein the peptide consists of the amino acid sequence of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44.

17. The method of claim 12, wherein the carcinoma is selected from liver cancer, lung cancer, breast cancer, pancreatic cancer, prostate cancer, or colorectal cancer, and wherein the sarcoma selected from an osteosarcoma, fibrosarcoma, or glioma.

18. The method of claim 12 wherein the peptide is administered via a route selected from the group consisting of oral administration, nasal administration, administration by inhalation, rectal administration, intraperitoneal injection, intravascular injection, subcutaneous injection, transcutaneous administration, and intramuscular injection.

19. The method of claim 12, further comprising administering a chemotherapeutic agent.

* * * * *

SEQUENCE LISTING

```
<160> NUMBER OF SEQ ID NOS: 45

<210> SEQ ID NO 1
<211> LENGTH: 13
<212> TYPE: PRT
<213> ORGANISM: Homo sapiens

<400> SEQUENCE: 1

Ile Ser Phe Gln Leu Met Leu Cys Val Leu Asp Tyr Phe
1               5                   10

<210> SEQ ID NO 2
<211> LENGTH: 7
<212> TYPE: PRT
<213> ORGANISM: Homo sapiens

<400> SEQUENCE: 2

Gln Leu Met Leu Cys Val Leu
1               5

<210> SEQ ID NO 3
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Gly, Ala, Leu, Ile, or Val
<220> FEATURE:
<221> NAME/KEY: MISC_FEATURE
<222> LOCATION: (2)..(2)
<223> OTHER INFORMATION: Xaa is absent, Ala, or Ser
<220> FEATURE:
```

```
<221> NAME/KEY: MISC_FEATURE
<222> LOCATION: (3)..(3)
<223> OTHER INFORMATION: Xaa is absent, Phe, or Tyr
<220> FEATURE:
<221> NAME/KEY: MISC_FEATURE
<222> LOCATION: (11)..(11)
<223> OTHER INFORMATION: Xaa is absent, Asp, or Asn
<220> FEATURE:
<221> NAME/KEY: MISC_FEATURE
<222> LOCATION: (12)..(12)
<223> OTHER INFORMATION: Xaa is absent, Phe, or Tyr
<220> FEATURE:
<221> NAME/KEY: MISC_FEATURE
<222> LOCATION: (13)..(13)
<223> OTHER INFORMATION: Xaa is absent, Phe, or Tyr

<400> SEQUENCE: 3

Xaa Xaa Xaa Gln Leu Met Leu Cys Val Leu Xaa Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent Gly, Ala, Leu, Ile, or Val
<220> FEATURE:
<221> NAME/KEY: MISC_FEATURE
<222> LOCATION: (2)..(2)
<223> OTHER INFORMATION: Xaa is absent, Ala, or Ser
<220> FEATURE:
<221> NAME/KEY: MISC_FEATURE
<222> LOCATION: (3)..(3)
<223> OTHER INFORMATION: Xaa is absent, Phe, or Tyr
<220> FEATURE:
<221> NAME/KEY: MISC_FEATURE
<222> LOCATION: (5)..(5)
<223> OTHER INFORMATION: Xaa is Gly, Ala, Leu, Ile, or Val
<220> FEATURE:
<221> NAME/KEY: MISC_FEATURE
<222> LOCATION: (7)..(7)
<223> OTHER INFORMATION: Xaa is Gly, Ala, Leu, Ile, or Val
<220> FEATURE:
<221> NAME/KEY: MISC_FEATURE
<222> LOCATION: (10)..(10)
<223> OTHER INFORMATION: Xaa is absent, Gly, Ala, Leu, Ile, or Val
<220> FEATURE:
<221> NAME/KEY: MISC_FEATURE
<222> LOCATION: (11)..(11)
<223> OTHER INFORMATION: Xaa is absent, Asp, or Asn
<220> FEATURE:
<221> NAME/KEY: MISC_FEATURE
<222> LOCATION: (12)..(12)
<223> OTHER INFORMATION: Xaa is absent, Phe, or Tyr
<220> FEATURE:
<221> NAME/KEY: MISC_FEATURE
<222> LOCATION: (13)..(13)
<223> OTHER INFORMATION: Xaa is absent, Phe, or Tyr

<400> SEQUENCE: 4

Xaa Xaa Xaa Gln Xaa Met Xaa Cys Val Xaa Xaa Xaa Xaa
1               5                   10

<210> SEQ ID NO 5
<211> LENGTH: 7
<212> TYPE: PRT
<213> ORGANISM: Homo sapiens

<400> SEQUENCE: 5

Ile Ser Phe Gln Leu Met Leu
1               5
```

```
<210> SEQ ID NO 6
<211> LENGTH: 7
<212> TYPE: PRT
<213> ORGANISM: Homo sapiens

<400> SEQUENCE: 6

Leu Cys Val Leu Asp Tyr Phe
1               5

<210> SEQ ID NO 7
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Gly, Ala, Leu, Ile, or Val
<220> FEATURE:
<221> NAME/KEY: MISC_FEATURE
<222> LOCATION: (2)..(2)
<223> OTHER INFORMATION: Xaa is absent, Ala, or Ser
<220> FEATURE:
<221> NAME/KEY: MISC_FEATURE
<222> LOCATION: (3)..(3)
<223> OTHER INFORMATION: Xaa is absent, Phe, or Tyr
<220> FEATURE:
<221> NAME/KEY: MISC_FEATURE
<222> LOCATION: (6)..(6)
<223> OTHER INFORMATION: Xaa is Met, Nle, or Ile
<220> FEATURE:
<221> NAME/KEY: MISC_FEATURE
<222> LOCATION: (8)..(8)
<223> OTHER INFORMATION: Xaa is Cys, Ala, or Val
<220> FEATURE:
<221> NAME/KEY: MISC_FEATURE
<222> LOCATION: (11)..(11)
<223> OTHER INFORMATION: Xaa is absent, Asp, or Asn
<220> FEATURE:
<221> NAME/KEY: MISC_FEATURE
<222> LOCATION: (12)..(12)
<223> OTHER INFORMATION: Xaa is absent, Phe, or Tyr
<220> FEATURE:
<221> NAME/KEY: MISC_FEATURE
<222> LOCATION: (13)..(13)
<223> OTHER INFORMATION: Xaa is absent, Phe, or Tyr

<400> SEQUENCE: 7

Xaa Xaa Xaa Gln Leu Xaa Leu Xaa Val Leu Xaa Xaa Xaa
1               5                   10

<210> SEQ ID NO 8
<211> LENGTH: 40
<212> TYPE: PRT
<213> ORGANISM: Homo sapiens

<400> SEQUENCE: 8

Lys Gly Glu Val Leu Gln Met Glu Asp Asp Leu Val Ile Ser Phe Gln
1               5                   10                  15

Leu Met Leu Cys Val Leu Asp Tyr Phe Ile Lys Leu Ser Pro Pro Met
                20                  25                  30

Leu Leu Lys Glu Pro Tyr Lys Thr
            35                  40

<210> SEQ ID NO 9
<211> LENGTH: 12
<212> TYPE: PRT
```

```
<213> ORGANISM: Homo sapiens

<400> SEQUENCE: 9

Lys Gly Glu Val Leu Gln Met Glu Asp Asp Leu Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Gly, Ala, Leu, Ile, or Val
<220> FEATURE:
<221> NAME/KEY: MISC_FEATURE
<222> LOCATION: (2)..(2)
<223> OTHER INFORMATION: Xaa is absent, Ala, or Ser
<220> FEATURE:
<221> NAME/KEY: MISC_FEATURE
<222> LOCATION: (3)..(3)
<223> OTHER INFORMATION: Xaa is absent, Phe, or Tyr
<220> FEATURE:
<221> NAME/KEY: MISC_FEATURE
<222> LOCATION: (4)..(4)
<223> OTHER INFORMATION: Xaa is absent, Gln, or Glu
<220> FEATURE:
<221> NAME/KEY: MISC_FEATURE
<222> LOCATION: (9)..(9)
<223> OTHER INFORMATION: Xaa is absent, Gly, Ala, Leu, Ile, or Val
<220> FEATURE:
<221> NAME/KEY: MISC_FEATURE
<222> LOCATION: (11)..(11)
<223> OTHER INFORMATION: Xaa is absent, Asp, or Asn
<220> FEATURE:
<221> NAME/KEY: MISC_FEATURE
<222> LOCATION: (12)..(12)
<223> OTHER INFORMATION: Xaa is absent, Phe, or Tyr
<220> FEATURE:
<221> NAME/KEY: MISC_FEATURE
<222> LOCATION: (13)..(13)
<223> OTHER INFORMATION: Xaa is absent, Phe, or Tyr

<400> SEQUENCE: 10

Xaa Xaa Xaa Xaa Leu Met Leu Cys Xaa Leu Xaa Xaa Xaa
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa is Gly, Ala, Leu, Ile, or Val
<220> FEATURE:
<221> NAME/KEY: MISC_FEATURE
<222> LOCATION: (4)..(4)
<223> OTHER INFORMATION: Xaa is Gly, Ala, Leu, Ile, or Val
<220> FEATURE:
<221> NAME/KEY: MISC_FEATURE
<222> LOCATION: (7)..(7)
<223> OTHER INFORMATION: Xaa is absent, Gly, Ala, Leu, Ile, or Val

<400> SEQUENCE: 11

Gln Xaa Met Xaa Cys Val Xaa
1               5

<210> SEQ ID NO 12
```

```
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: Xaa is Met, Nle, or Ile
<220> FEATURE:
<221> NAME/KEY: MISC_FEATURE
<222> LOCATION: (5)..(5)
<223> OTHER INFORMATION: Xaa is Cys, Ala, or Val

<400> SEQUENCE: 12

Gln Leu Xaa Leu Xaa Val Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Gln, or Glu
<220> FEATURE:
<221> NAME/KEY: MISC_FEATURE
<222> LOCATION: (6)..(6)
<223> OTHER INFORMATION: Xaa is absent, Gly, Ala, Leu, Ile, or Val

<400> SEQUENCE: 13

Xaa Leu Met Leu Cys Xaa Leu
1               5

<210> SEQ ID NO 14
<211> LENGTH: 18
<212> TYPE: PRT
<213> ORGANISM: Homo sapiens

<400> SEQUENCE: 14

Asp Leu Val Ile Ser Phe Gln Leu Met Leu Cys Val Leu Asp Tyr Phe
1               5                   10                  15

Ile Lys

<210> SEQ ID NO 15
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Asp, or Asn
<220> FEATURE:
<221> NAME/KEY: MISC_FEATURE
<222> LOCATION: (2)..(2)
<223> OTHER INFORMATION: Xaa is absent, Gly, Ala, Leu, Ile, or Val
<220> FEATURE:
<221> NAME/KEY: MISC_FEATURE
<222> LOCATION: (3)..(3)
<223> OTHER INFORMATION: Xaa is absent, Gly, Ala, Leu, Ile, or Val
<220> FEATURE:
<221> NAME/KEY: MISC_FEATURE
<222> LOCATION: (17)..(17)
<223> OTHER INFORMATION: Xaa is absent, Gly, Ala, Leu, Ile, or Val
<220> FEATURE:
<221> NAME/KEY: MISC_FEATURE
<222> LOCATION: (18)..(18)
```

<223> OTHER INFORMATION: Xaa is absent, Lys or Arg

<400> SEQUENCE: 15

Xaa Xaa Xaa Ile Ser Phe Gln Leu Met Leu Cys Val Leu Asp Tyr Phe
1               5                   10                  15

Xaa Xaa

<210> SEQ ID NO 16
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Asp, or Asn
<220> FEATURE:
<221> NAME/KEY: MISC_FEATURE
<222> LOCATION: (2)..(2)
<223> OTHER INFORMATION: Xaa is absent, Gly, Ala, Leu, Ile, or Val
<220> FEATURE:
<221> NAME/KEY: MISC_FEATURE
<222> LOCATION: (3)..(3)
<223> OTHER INFORMATION: Xaa is absent, Gly, Ala, Leu, Ile, or Val
<220> FEATURE:
<221> NAME/KEY: MISC_FEATURE
<222> LOCATION: (4)..(4)
<223> OTHER INFORMATION: Xaa is absent, Gly, Ala, Leu, Ile, or Val
<220> FEATURE:
<221> NAME/KEY: MISC_FEATURE
<222> LOCATION: (5)..(5)
<223> OTHER INFORMATION: Xaa is absent, Ala, or Ser
<220> FEATURE:
<221> NAME/KEY: MISC_FEATURE
<222> LOCATION: (6)..(6)
<223> OTHER INFORMATION: Xaa is absent, Phe, or Tyr
<220> FEATURE:
<221> NAME/KEY: MISC_FEATURE
<222> LOCATION: (14)..(14)
<223> OTHER INFORMATION: Xaa is absent, Asp, or Asn
<220> FEATURE:
<221> NAME/KEY: MISC_FEATURE
<222> LOCATION: (15)..(15)
<223> OTHER INFORMATION: Xaa is absent, Phe, or Tyr
<220> FEATURE:
<221> NAME/KEY: MISC_FEATURE
<222> LOCATION: (16)..(16)
<223> OTHER INFORMATION: Xaa is absent, Phe, or Tyr
<220> FEATURE:
<221> NAME/KEY: MISC_FEATURE
<222> LOCATION: (17)..(17)
<223> OTHER INFORMATION: Xaa is absent, Gly, Ala, Leu, Ile, or Val
<220> FEATURE:
<221> NAME/KEY: MISC_FEATURE
<222> LOCATION: (18)..(18)
<223> OTHER INFORMATION: Xaa is absent, Lys or Arg

<400> SEQUENCE: 16

Xaa Xaa Xaa Xaa Xaa Xaa Gln Leu Met Leu Cys Val Leu Xaa Xaa Xaa
1               5                   10                  15

Xaa Xaa

<210> SEQ ID NO 17
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Asp, or Asn

```
<220> FEATURE:
<221> NAME/KEY: MISC_FEATURE
<222> LOCATION: (2)..(2)
<223> OTHER INFORMATION: Xaa is absent, Gly, Ala, Leu, Ile, or Val
<220> FEATURE:
<221> NAME/KEY: MISC_FEATURE
<222> LOCATION: (3)..(3)
<223> OTHER INFORMATION: Xaa is absent, Gly, Ala, Leu, Ile, or Val
<220> FEATURE:
<221> NAME/KEY: MISC_FEATURE
<222> LOCATION: (4)..(4)
<223> OTHER INFORMATION: Xaa is absent, Gly, Ala, Leu, Ile, or Val
<220> FEATURE:
<221> NAME/KEY: MISC_FEATURE
<222> LOCATION: (5)..(5)
<223> OTHER INFORMATION: Xaa is absent, Ala, or Ser
<220> FEATURE:
<221> NAME/KEY: MISC_FEATURE
<222> LOCATION: (6)..(6)
<223> OTHER INFORMATION: Xaa is absent, Phe, or Tyr
<220> FEATURE:
<221> NAME/KEY: MISC_FEATURE
<222> LOCATION: (8)..(8)
<223> OTHER INFORMATION: Xaa is Gly, Ala, Leu, Ile, or Val
<220> FEATURE:
<221> NAME/KEY: MISC_FEATURE
<222> LOCATION: (10)..(10)
<223> OTHER INFORMATION: Xaa is Gly, Ala, Leu, Ile, or Val
<220> FEATURE:
<221> NAME/KEY: MISC_FEATURE
<222> LOCATION: (13)..(13)
<223> OTHER INFORMATION: Xaa is absent, Gly, Ala, Leu, Ile, or Val
<220> FEATURE:
<221> NAME/KEY: MISC_FEATURE
<222> LOCATION: (14)..(14)
<223> OTHER INFORMATION: Xaa is absent, Asp, or Asn
<220> FEATURE:
<221> NAME/KEY: MISC_FEATURE
<222> LOCATION: (15)..(15)
<223> OTHER INFORMATION: Xaa is absent, Phe, or Tyr
<220> FEATURE:
<221> NAME/KEY: MISC_FEATURE
<222> LOCATION: (16)..(16)
<223> OTHER INFORMATION: Xaa is absent, Phe, or Tyr
<220> FEATURE:
<221> NAME/KEY: MISC_FEATURE
<222> LOCATION: (17)..(17)
<223> OTHER INFORMATION: Xaa is absent, Gly, Ala, Leu, Ile, or Val
<220> FEATURE:
<221> NAME/KEY: MISC_FEATURE
<222> LOCATION: (18)..(18)
<223> OTHER INFORMATION: Xaa is absent, Lys or Arg

<400> SEQUENCE: 17

Xaa Xaa Xaa Xaa Xaa Xaa Gln Xaa Met Xaa Cys Val Xaa Xaa Xaa Xaa
1               5                   10                  15

Xaa Xaa

<210> SEQ ID NO 18
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Asp, or Asn
<220> FEATURE:
<221> NAME/KEY: MISC_FEATURE
<222> LOCATION: (2)..(2)
<223> OTHER INFORMATION: Xaa is absent, Gly, Ala, Leu, Ile, or Val
<220> FEATURE:
<221> NAME/KEY: MISC_FEATURE
<222> LOCATION: (3)..(3)
<223> OTHER INFORMATION: Xaa is absent, Gly, Ala, Leu, Ile, or Val
```

```
<220> FEATURE:
<221> NAME/KEY: MISC_FEATURE
<222> LOCATION: (4)..(4)
<223> OTHER INFORMATION: Xaa is absent, Gly, Ala, Leu, Ile, or Val
<220> FEATURE:
<221> NAME/KEY: MISC_FEATURE
<222> LOCATION: (5)..(5)
<223> OTHER INFORMATION: Xaa is absent, Ala, or Ser
<220> FEATURE:
<221> NAME/KEY: MISC_FEATURE
<222> LOCATION: (6)..(6)
<223> OTHER INFORMATION: Xaa is absent, Phe, or Tyr
<220> FEATURE:
<221> NAME/KEY: MISC_FEATURE
<222> LOCATION: (9)..(9)
<223> OTHER INFORMATION: Xaa is Met, Nle, or Ile
<220> FEATURE:
<221> NAME/KEY: MISC_FEATURE
<222> LOCATION: (11)..(11)
<223> OTHER INFORMATION: Xaa is Cys, Ala, or Val
<220> FEATURE:
<221> NAME/KEY: MISC_FEATURE
<222> LOCATION: (14)..(14)
<223> OTHER INFORMATION: Xaa is absent, Asp, or Asn
<220> FEATURE:
<221> NAME/KEY: MISC_FEATURE
<222> LOCATION: (15)..(15)
<223> OTHER INFORMATION: Xaa is absent, Phe, or Tyr
<220> FEATURE:
<221> NAME/KEY: MISC_FEATURE
<222> LOCATION: (16)..(16)
<223> OTHER INFORMATION: Xaa is absent, Phe, or Tyr
<220> FEATURE:
<221> NAME/KEY: MISC_FEATURE
<222> LOCATION: (17)..(17)
<223> OTHER INFORMATION: Xaa is absent, Gly, Ala, Leu, Ile, or Val
<220> FEATURE:
<221> NAME/KEY: MISC_FEATURE
<222> LOCATION: (18)..(18)
<223> OTHER INFORMATION: Xaa is absent, Lys or Arg

<400> SEQUENCE: 18

Xaa Xaa Xaa Xaa Xaa Xaa Gln Leu Xaa Leu Xaa Val Leu Xaa Xaa Xaa
1               5                   10                  15

Xaa Xaa

<210> SEQ ID NO 19
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Asp, or Asn
<220> FEATURE:
<221> NAME/KEY: MISC_FEATURE
<222> LOCATION: (2)..(2)
<223> OTHER INFORMATION: Xaa is absent, Gly, Ala, Leu, Ile, or Val
<220> FEATURE:
<221> NAME/KEY: MISC_FEATURE
<222> LOCATION: (3)..(3)
<223> OTHER INFORMATION: Xaa is absent, Gly, Ala, Leu, Ile, or Val
<220> FEATURE:
<221> NAME/KEY: MISC_FEATURE
<222> LOCATION: (4)..(4)
<223> OTHER INFORMATION: Xaa is absent, Gly, Ala, Leu, Ile, or Val
<220> FEATURE:
<221> NAME/KEY: MISC_FEATURE
<222> LOCATION: (5)..(5)
<223> OTHER INFORMATION: Xaa is absent, Ala, or Ser
<220> FEATURE:
<221> NAME/KEY: MISC_FEATURE
<222> LOCATION: (6)..(6)
<223> OTHER INFORMATION: Xaa is absent, Phe, or Tyr
```

```
<220> FEATURE:
<221> NAME/KEY: MISC_FEATURE
<222> LOCATION: (7)..(7)
<223> OTHER INFORMATION: Xaa is absent, Gln, or Glu
<220> FEATURE:
<221> NAME/KEY: MISC_FEATURE
<222> LOCATION: (12)..(12)
<223> OTHER INFORMATION: Xaa is absent, Gly, Ala, Leu, Ile, or Val
<220> FEATURE:
<221> NAME/KEY: MISC_FEATURE
<222> LOCATION: (14)..(14)
<223> OTHER INFORMATION: Xaa is absent, Asp, or Asn
<220> FEATURE:
<221> NAME/KEY: MISC_FEATURE
<222> LOCATION: (15)..(15)
<223> OTHER INFORMATION: Xaa is absent, Phe, or Tyr
<220> FEATURE:
<221> NAME/KEY: MISC_FEATURE
<222> LOCATION: (16)..(16)
<223> OTHER INFORMATION: Xaa is absent, Phe, or Tyr
<220> FEATURE:
<221> NAME/KEY: MISC_FEATURE
<222> LOCATION: (17)..(17)
<223> OTHER INFORMATION: Xaa is absent, Gly, Ala, Leu, Ile, or Val
<220> FEATURE:
<221> NAME/KEY: MISC_FEATURE
<222> LOCATION: (18)..(18)
<223> OTHER INFORMATION: Xaa is absent, Lys or Arg

<400> SEQUENCE: 19

Xaa Xaa Xaa Xaa Xaa Xaa Xaa Leu Met Leu Cys Xaa Leu Xaa Xaa Xaa
1               5                   10                  15

Xaa Xaa

<210> SEQ ID NO 20
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Gly, Ala, Leu, Ile, or Val
<220> FEATURE:
<221> NAME/KEY: MISC_FEATURE
<222> LOCATION: (2)..(2)
<223> OTHER INFORMATION: Xaa is absent, Ala, or Ser
<220> FEATURE:
<221> NAME/KEY: MISC_FEATURE
<222> LOCATION: (3)..(3)
<223> OTHER INFORMATION: Xaa is absent, Phe, or Tyr
<220> FEATURE:
<221> NAME/KEY: MISC_FEATURE
<222> LOCATION: (4)..(4)
<223> OTHER INFORMATION: Xaa is absent, Gln, or Glu
<220> FEATURE:
<221> NAME/KEY: MISC_FEATURE
<222> LOCATION: (5)..(5)
<223> OTHER INFORMATION: Xaa is Gly, Ala, Leu, Ile, or Val
<220> FEATURE:
<221> NAME/KEY: MISC_FEATURE
<222> LOCATION: (6)..(6)
<223> OTHER INFORMATION: Xaa is Met, Nle, or Ile
<220> FEATURE:
<221> NAME/KEY: MISC_FEATURE
<222> LOCATION: (7)..(7)
<223> OTHER INFORMATION: Xaa is Gly, Ala, Leu, Ile, or Val
<220> FEATURE:
<221> NAME/KEY: MISC_FEATURE
<222> LOCATION: (8)..(8)
<223> OTHER INFORMATION: Xaa is Cys, Ala, or Val
<220> FEATURE:
<221> NAME/KEY: MISC_FEATURE
<222> LOCATION: (9)..(9)
<223> OTHER INFORMATION: Xaa is absent, Gly, Ala, Leu, Ile, or Val
```

```
<220> FEATURE:
<221> NAME/KEY: MISC_FEATURE
<222> LOCATION: (10)..(10)
<223> OTHER INFORMATION: Xaa is Gly, Ala, Leu, Ile, or Val
<220> FEATURE:
<221> NAME/KEY: MISC_FEATURE
<222> LOCATION: (11)..(11)
<223> OTHER INFORMATION: Xaa is absent, Asp, or Asn
<220> FEATURE:
<221> NAME/KEY: MISC_FEATURE
<222> LOCATION: (12)..(12)
<223> OTHER INFORMATION: Xaa is absent, Phe, or Tyr
<220> FEATURE:
<221> NAME/KEY: MISC_FEATURE
<222> LOCATION: (13)..(13)
<223> OTHER INFORMATION: Xaa is absent, Phe, or Tyr

<400> SEQUENCE: 20

Xaa Xaa Xaa Xaa Xaa Xaa Xaa Xaa Xaa Xaa Xaa Xaa Xaa
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa is absent, Asp, or Asn
<220> FEATURE:
<221> NAME/KEY: MISC_FEATURE
<222> LOCATION: (2)..(2)
<223> OTHER INFORMATION: Xaa is absent, Gly, Ala, Leu, Ile, or Val
<220> FEATURE:
<221> NAME/KEY: MISC_FEATURE
<222> LOCATION: (3)..(3)
<223> OTHER INFORMATION: Xaa is absent, Gly, Ala, Leu, Ile, or Val
<220> FEATURE:
<221> NAME/KEY: MISC_FEATURE
<222> LOCATION: (4)..(4)
<223> OTHER INFORMATION: Xaa is absent, Gly, Ala, Leu, Ile, or Val
<220> FEATURE:
<221> NAME/KEY: MISC_FEATURE
<222> LOCATION: (5)..(5)
<223> OTHER INFORMATION: Xaa is absent, Ala, or Ser
<220> FEATURE:
<221> NAME/KEY: MISC_FEATURE
<222> LOCATION: (6)..(6)
<223> OTHER INFORMATION: Xaa is absent, Phe, or Tyr
<220> FEATURE:
<221> NAME/KEY: MISC_FEATURE
<222> LOCATION: (7)..(7)
<223> OTHER INFORMATION: Xaa is absent, Gln, or Glu
<220> FEATURE:
<221> NAME/KEY: MISC_FEATURE
<222> LOCATION: (8)..(8)
<223> OTHER INFORMATION: Xaa is Gly, Ala, Leu, Ile, or Val
<220> FEATURE:
<221> NAME/KEY: MISC_FEATURE
<222> LOCATION: (9)..(9)
<223> OTHER INFORMATION: Xaa is Met, Nle, or Ile
<220> FEATURE:
<221> NAME/KEY: MISC_FEATURE
<222> LOCATION: (10)..(10)
<223> OTHER INFORMATION: Xaa is Gly, Ala, Leu, Ile, or Val
<220> FEATURE:
<221> NAME/KEY: MISC_FEATURE
<222> LOCATION: (11)..(11)
<223> OTHER INFORMATION: Xaa is Cys, Ala, or Val
<220> FEATURE:
<221> NAME/KEY: MISC_FEATURE
<222> LOCATION: (12)..(12)
<223> OTHER INFORMATION: Xaa is absent, Gly, Ala, Leu, Ile, or Val
<220> FEATURE:
<221> NAME/KEY: MISC_FEATURE
```

```
<222> LOCATION: (13)..(13)
<223> OTHER INFORMATION: Xaa is absent, Gly, Ala, Leu, Ile, or Val
<220> FEATURE:
<221> NAME/KEY: MISC_FEATURE
<222> LOCATION: (14)..(14)
<223> OTHER INFORMATION: Xaa is absent, Asp, or Asn
<220> FEATURE:
<221> NAME/KEY: MISC_FEATURE
<222> LOCATION: (15)..(15)
<223> OTHER INFORMATION: Xaa is absent, Phe, or Tyr
<220> FEATURE:
<221> NAME/KEY: MISC_FEATURE
<222> LOCATION: (16)..(16)
<223> OTHER INFORMATION: Xaa is absent, Phe, or Tyr
<220> FEATURE:
<221> NAME/KEY: MISC_FEATURE
<222> LOCATION: (17)..(17)
<223> OTHER INFORMATION: Xaa is absent, Gly, Ala, Leu, Ile, or Val
<220> FEATURE:
<221> NAME/KEY: MISC_FEATURE
<222> LOCATION: (18)..(18)
<223> OTHER INFORMATION: Xaa is absent, Lys or Arg

<400> SEQUENCE: 21

Xaa Xaa Xaa Xaa Xaa Xaa Xaa Xaa Xaa Xaa Xaa Xaa Xaa Xaa
1               5                   10                  15

Xaa Xaa

<210> SEQ ID NO 22
<211> LENGTH: 17
<212> TYPE: PRT
<213> ORGANISM: Homo sapiens

<400> SEQUENCE: 22

Leu Val Ile Ser Phe Gln Leu Met Leu Cys Val Leu Asp Tyr Phe Ile
1               5                   10                  15

Lys

<210> SEQ ID NO 23
<211> LENGTH: 16
<212> TYPE: PRT
<213> ORGANISM: Homo sapiens

<400> SEQUENCE: 23

Val Ile Ser Phe Gln Leu Met Leu Cys Val Leu Asp Tyr Phe Ile Lys
1               5                   10                  15

<210> SEQ ID NO 24
<211> LENGTH: 15
<212> TYPE: PRT
<213> ORGANISM: Homo sapiens

<400> SEQUENCE: 24

Ile Ser Phe Gln Leu Met Leu Cys Val Leu Asp Tyr Phe Ile Lys
1               5                   10                  15

<210> SEQ ID NO 25
<211> LENGTH: 14
<212> TYPE: PRT
<213> ORGANISM: Homo sapiens

<400> SEQUENCE: 25

Ser Phe Gln Leu Met Leu Cys Val Leu Asp Tyr Phe Ile Lys
1               5                   10

<210> SEQ ID NO 26
<211> LENGTH: 13
```

```
<212> TYPE: PRT
<213> ORGANISM: Homo sapiens

<400> SEQUENCE: 26

Phe Gln Leu Met Leu Cys Val Leu Asp Tyr Phe Ile Lys
1               5                   10

<210> SEQ ID NO 27
<211> LENGTH: 12
<212> TYPE: PRT
<213> ORGANISM: Homo sapiens

<400> SEQUENCE: 27

Gln Leu Met Leu Cys Val Leu Asp Tyr Phe Ile Lys
1               5                   10

<210> SEQ ID NO 28
<211> LENGTH: 11
<212> TYPE: PRT
<213> ORGANISM: Homo sapiens

<400> SEQUENCE: 28

Leu Met Leu Cys Val Leu Asp Tyr Phe Ile Lys
1               5                   10

<210> SEQ ID NO 29
<211> LENGTH: 16
<212> TYPE: PRT
<213> ORGANISM: Homo sapiens

<400> SEQUENCE: 29

Asp Leu Val Ile Ser Phe Gln Leu Met Leu Cys Val Leu Asp Tyr Phe
1               5                   10                  15

<210> SEQ ID NO 30
<211> LENGTH: 15
<212> TYPE: PRT
<213> ORGANISM: Homo sapiens

<400> SEQUENCE: 30

Asp Leu Val Ile Ser Phe Gln Leu Met Leu Cys Val Leu Asp Tyr
1               5                   10                  15

<210> SEQ ID NO 31
<211> LENGTH: 14
<212> TYPE: PRT
<213> ORGANISM: Homo sapiens

<400> SEQUENCE: 31

Asp Leu Val Ile Ser Phe Gln Leu Met Leu Cys Val Leu Asp
1               5                   10

<210> SEQ ID NO 32
<211> LENGTH: 13
<212> TYPE: PRT
<213> ORGANISM: Homo sapiens

<400> SEQUENCE: 32

Asp Leu Val Ile Ser Phe Gln Leu Met Leu Cys Val Leu
1               5                   10

<210> SEQ ID NO 33
<211> LENGTH: 10
<212> TYPE: PRT
<213> ORGANISM: Homo sapiens
```

<400> SEQUENCE: 33

Asp Leu Val Ile Ser Phe Gln Leu Met Leu
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Synthesized

<400> SEQUENCE: 34

Asp Leu Val Ile Ser Phe Ala Leu Met Leu Cys Val Leu Asp Tyr Phe
1               5                   10                  15

Ile Lys

<210> SEQ ID NO 35
<211> LENGTH: 18
<212> TYPE: PRT
<213> ORGANISM: Artificial Sequence
<220> FEATURE:
<223> OTHER INFORMATION: Synthesized

<400> SEQUENCE: 35

Asp Leu Val Ile Ser Phe Gln Gly Met Leu Cys Val Leu Asp Tyr Phe
1               5                   10                  15

Ile Lys

<210> SEQ ID NO 36
<211> LENGTH: 7
<212> TYPE: PRT
<213> ORGANISM: Artificial Sequence
<220> FEATURE:
<223> OTHER INFORMATION: Synthesized

<400> SEQUENCE: 36

Gln Gly Met Leu Cys Val Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Synthesized

<400> SEQUENCE: 37

Gln Leu Met Gly Cys Val Leu
1               5

<210> SEQ ID NO 38
<211> LENGTH: 8
<212> TYPE: PRT
<213> ORGANISM: Artificial Sequence
<220> FEATURE:
<223> OTHER INFORMATION: Synthesized

<400> SEQUENCE: 38

Gln Leu Met Leu Cys Val Leu Asp
1               5

<210> SEQ ID NO 39
<211> LENGTH: 6
<212> TYPE: PRT

```
<213> ORGANISM: Artificial Sequence
<220> FEATURE:
<223> OTHER INFORMATION: Synthesized

<400> SEQUENCE: 39

Leu Met Leu Cys Val Leu
1               5

<210> SEQ ID NO 40
<211> LENGTH: 6
<212> TYPE: PRT
<213> ORGANISM: Artificial Sequence
<220> FEATURE:
<223> OTHER INFORMATION: Synthesized

<400> SEQUENCE: 40

Gly Met Leu Cys Val Leu
1               5

<210> SEQ ID NO 41
<211> LENGTH: 6
<212> TYPE: PRT
<213> ORGANISM: Artificial Sequence
<220> FEATURE:
<223> OTHER INFORMATION: Synthesized

<400> SEQUENCE: 41

Leu Met Gly Cys Val Leu
1               5

<210> SEQ ID NO 42
<211> LENGTH: 7
<212> TYPE: PRT
<213> ORGANISM: Artificial Sequence
<220> FEATURE:
<223> OTHER INFORMATION: Synthesized

<400> SEQUENCE: 42

Leu Met Leu Cys Val Leu Asp
1               5

<210> SEQ ID NO 43
<211> LENGTH: 7
<212> TYPE: PRT
<213> ORGANISM: Artificial Sequence
<220> FEATURE:
<223> OTHER INFORMATION: Synthesized

<400> SEQUENCE: 43

Gly Met Leu Cys Val Leu Asp
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Leu Met Gly Cys Val Leu Asp
1               5

<210> SEQ ID NO 45
<211> LENGTH: 928
<212> TYPE: PRT
<213> ORGANISM: Homo sapiens
```

-continued

```
<400> SEQUENCE: 45

Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
                35                  40                  45

Phe Glu Glu Thr Glu Glu Pro Asp Phe Thr Ala Leu Cys Gln Lys Leu
        50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Val Asn Val
        355                 360                 365

Ile Pro Pro His Thr Pro Val Arg Thr Val Met Asn Thr Ile Gln Gln
            370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
```

```
                    405                 410                 415
Lys Arg Val Lys Asp Ile Gly Tyr Ile Phe Lys Glu Lys Phe Ala Lys
                420                 425                 430

Ala Val Gly Gln Gly Cys Val Glu Ile Gly Ser Gln Arg Tyr Lys Leu
                435                 440                 445

Gly Val Arg Leu Tyr Tyr Arg Val Met Glu Ser Met Leu Lys Ser Glu
                450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                    485                 490                 495

Thr Tyr Ser Arg Ser Thr Ser Gln Asn Leu Asp Ser Gly Thr Asp Leu
                500                 505                 510

Ser Phe Pro Trp Ile Leu Asn Val Leu Asn Leu Lys Ala Phe Asp Phe
                515                 520                 525

Tyr Lys Val Ile Glu Ser Phe Ile Lys Ala Glu Gly Asn Leu Thr Arg
                530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                    565                 570                 575

Lys Asp Arg Glu Gly Pro Thr Asp His Leu Glu Ser Ala Cys Pro Leu
                580                 585                 590

Asn Leu Pro Leu Gln Asn Asn His Thr Ala Ala Asp Met Tyr Leu Ser
                595                 600                 605

Pro Val Arg Ser Pro Lys Lys Lys Gly Ser Thr Thr Arg Val Asn Ser
                610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                    645                 650                 655

Leu Ala Tyr Leu Arg Leu Asn Thr Leu Cys Glu Arg Leu Leu Ser Glu
                660                 665                 670

His Pro Glu Leu Glu His Ile Ile Trp Thr Leu Phe Gln His Thr Leu
                675                 680                 685

Gln Asn Glu Tyr Glu Leu Met Arg Asp Arg His Leu Asp Gln Ile Met
                690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                    725                 730                 735

Glu Thr Phe Lys Arg Val Leu Ile Lys Glu Glu Tyr Asp Ser Ile
                740                 745                 750

Ile Val Phe Tyr Asn Ser Val Phe Met Gln Arg Leu Lys Thr Asn Ile
                755                 760                 765

Leu Gln Tyr Ala Ser Thr Arg Pro Pro Thr Leu Ser Pro Ile Pro His
770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                    805                 810                 815

Glu Gly Leu Pro Thr Pro Thr Lys Met Thr Pro Arg Ser Arg Ile Leu
                820                 825                 830
```

```
Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865             870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
            915                 920                 925
```